(12) United States Patent
Rossi et al.

(10) Patent No.: US 10,167,474 B2
(45) Date of Patent: *Jan. 1, 2019

(54) CELL-SPECIFIC INTERNALIZING RNA APTAMERS AGAINST HUMAN CCR5 AND USES THEREFORE

(71) Applicants: City of Hope, Duarte, CA (US); The Scripps Research Institute, La Jolla, CA (US)

(72) Inventors: John Rossi, Alta Loma, CA (US); Jiehua Zhou, Monrovia, CA (US); Marc Weinberg, Encinitas, CA (US); Kevin Morris, Sierra Madre, CA (US)

(73) Assignees: City of Hope, Duarte, CA (US); The Scripps Research Institute, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/469,320

(22) Filed: Mar. 24, 2017

(65) Prior Publication Data

US 2018/0080026 A1 Mar. 22, 2018

Related U.S. Application Data

(63) Continuation of application No. 14/801,710, filed on Jul. 16, 2015, now Pat. No. 9,605,266.

(60) Provisional application No. 62/025,368, filed on Jul. 16, 2014.

(51) Int. Cl.
*C12N 15/11* (2006.01)
*C12N 15/115* (2010.01)

(52) U.S. Cl.
CPC ........ *C12N 15/115* (2013.01); *C12N 2310/16* (2013.01)

(58) Field of Classification Search
CPC ................... C12N 15/115; C12N 2310/16
See application file for complete search history.

(56) References Cited

U.S. PATENT DOCUMENTS

| | | | |
|---|---|---|---|
| 6,207,816 B1 | 3/2001 | Gold et al. | |
| 9,605,266 B2 | 3/2017 | Rossi et al. | |
| 2004/0137010 A1 | 7/2004 | Wilson et al. | |
| 2006/0014212 A1 | 1/2006 | Benkovic et al. | |
| 2009/0220514 A1* | 9/2009 | Rubin | C12N 15/1137 424/139.1 |
| 2013/0022538 A1 | 1/2013 | Rossi et al. | |
| 2014/0056959 A1* | 2/2014 | Giangrande | C12N 15/115 424/423 |
| 2016/0003835 A1 | 1/2016 | Halbert et al. | |
| 2016/0289681 A1* | 10/2016 | Rossi | C12N 15/1131 |

* cited by examiner

*Primary Examiner* — Dana H Shin
(74) *Attorney, Agent, or Firm* — Mintz Levin Cohn Ferris Glovsky and Popeo, P.C.

(57) ABSTRACT

Provided herein are fluoropyrimidine-modified RNA aptamers capable of binding CCR5. The compositions and methods provided herein are, inter alia, useful for the delivery of antiviral drugs (e.g., siRNAs) and preventing HIV entry into a target cell.

18 Claims, 32 Drawing Sheets

Specification includes a Sequence Listing.

SEQUENCE LISTING

<160> NUMBER OF SEQ ID NOS: 85

<210> SEQ ID NO 1
<211> LENGTH: 51
<212> TYPE: RNA
<213> ORGANISM: Artificial Sequence

```
<220> FEATURE:
<223> OTHER INFORMATION: Synthetic polynucleotide

<400> SEQUENCE: 1
gggaggacga ugcgggccuu cguuuguuuc guccacagac gacucgcccg a        51

<210> SEQ ID NO 2
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (16)..(35)
<223> OTHER INFORMATION: n is a, c, g, or t

<400> SEQUENCE: 2
gggaggacga tgcggnnnnn nnnnnnnnnn nnnnncagac gactcgcccg a        51

<210> SEQ ID NO 3
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 3
taatacgact cactataggg aggacgatgc gg                             32

<210> SEQ ID NO 4
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 4
tcgggcgagt cgtctg                                               16

<210> SEQ ID NO 5
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(20)
<223> OTHER INFORMATION: Residue is dT
<220> FEATURE:
<221> NAME/KEY: misc_feature
<222> LOCATION: (21)..(21)
<223> OTHER INFORMATION: Residue is dT

<400> SEQUENCE: 5
cucugcuucg gugucgaaat t                                         21

<210> SEQ ID NO 6
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(20)
<223> OTHER INFORMATION: Residue is dT
<220> FEATURE:
```

```
<221> NAME/KEY: misc_feature
<222> LOCATION: (21)..(21)
<223> OTHER INFORMATION: Residue is dT

<400> SEQUENCE: 6
uuucgacacc gaagcagagt t                                              21

<210> SEQ ID NO 7
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(24)
<223> OTHER INFORMATION: Residue is dG
<220> FEATURE:
<221> NAME/KEY: misc_feature
<222> LOCATION: (25)..(25)
<223> OTHER INFORMATION: Residue is dC

<400> SEQUENCE: 7
cgacauugca gcucguguac caggc                                          25

<210> SEQ ID NO 8
<211> LENGTH: 27
<212> TYPE: RNA
<213> ORGANISM: Artificial Sequence
<220> FEATURE:
<223> OTHER INFORMATION: Synthetic polynucleotide

<400> SEQUENCE: 8
gccugguaca cgagcugcaa ugucguu                                        27

<210> SEQ ID NO 9
<211> LENGTH: 51
<212> TYPE: RNA
<213> ORGANISM: Artificial Sequence
<220> FEATURE:
<223> OTHER INFORMATION: Synthetic polynucleotide

<400> SEQUENCE: 9
gggaggacga ugcgggccuu cguuuguuuc guccacagac gacucgcccg a              51

<210> SEQ ID NO 10
<211> LENGTH: 80
<212> TYPE: RNA
<213> ORGANISM: Artificial Sequence
<220> FEATURE:
<223> OTHER INFORMATION: Synthetic polynucleotide

<400> SEQUENCE: 10
gggaggacga ugcgggccuu cguuuguuuc guccacagac gacucgcccg auucaaagcc     60
gacauugcag cucguguacc                                                80

<210> SEQ ID NO 11
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 11
uacacgagcu gcaaugucgg cuuug                                          25
```

```
<210> SEQ ID NO 12
<211> LENGTH: 84
<212> TYPE: RNA
<213> ORGANISM: Artificial Sequence
<220> FEATURE:
<223> OTHER INFORMATION: Synthetic polynucleotide

<400> SEQUENCE: 12
gggaggacga ugcgggccuu cguuuguuuc guccacagac gacucgcccg auuuuuuuc      60 gacauugcag cucguguacc aggc                                           84

<210> SEQ ID NO 13
<211> LENGTH: 27
<212> TYPE: RNA
<213> ORGANISM: Artificial Sequence
<220> FEATURE:
<223> OTHER INFORMATION: Synthetic polynucleotide

<400> SEQUENCE: 13
gccugguaca cgagcugcaa ugucggc                                        27

<210> SEQ ID NO 14
<211> LENGTH: 74
<212> TYPE: RNA
<213> ORGANISM: Artificial Sequence
<220> FEATURE:
<223> OTHER INFORMATION: Synthetic polynucleotide

<400> SEQUENCE: 14
gggaggacga ugcgggccuu cguuuguuuc guccacagac gacucgcccg auuacgugag      60
acguucggug aauu                                                      74

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(20)
<223> OTHER INFORMATION: Residue is dT
<220> FEATURE:
<221> NAME/KEY: misc_feature
<222> LOCATION: (21)..(21)
<223> OTHER INFORMATION: Residue is dT

<400> SEQUENCE: 15
uucaccgaac gucucacgut t                                              21

<210> SEQ ID NO 16
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 16
taatacgact cactataggg aggacgatgc gg                                  32

<210> SEQ ID NO 17
<211> LENGTH: 16
<212> TYPE: DNA
<213> ORGANISM: Artificial Sequence
<220> FEATURE:
<223> OTHER INFORMATION: Synthetic polynucleotide
```

```
<400> SEQUENCE: 17
tcgggcgagt cgtctg                                                      16

<210> SEQ ID NO 18
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 18
cattgacctc aactacatg                                                   19

<210> SEQ ID NO 19
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 19
tctccatggt ggtgaagac                                                   19

<210> SEQ ID NO 20
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 20
cagattgatg gtgcctacag tcgggcgugt cgtctg                                36

<210> SEQ ID NO 21
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 21
aatgatacgg cgaccaccga caggttcaga gttcgatcgg gaggacgatg cgg             53

<210> SEQ ID NO 22
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 22
cagattgatg gtgcctacag tcgggcgugt cgtctg                                36

<210> SEQ ID NO 23
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(30)
<223> OTHER INFORMATION: n is a, c, g, or t

<400> SEQUENCE: 23
caagcagaag acggcatacg agatnnnnnn cagattgatg gtgcctacag                 50
```

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24
aatgatacgg cgaccaccga                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
caagcagaag acggcatacg                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
aatgatacgg cgaccaccga                                               20

<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(20)
<223> OTHER INFORMATION: Residue is dT
<220> FEATURE:
<221> NAME/KEY: misc_feature
<222> LOCATION: (21)..(21)
<223> OTHER INFORMATION: Residue is dT

<400> SEQUENCE: 27
cucugcuucg gugucgaaat t                                             21

<210> SEQ ID NO 28
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(20)
<223> OTHER INFORMATION: Residue is dT
<220> FEATURE:
<221> NAME/KEY: misc_feature
<222> LOCATION: (21)..(21)
<223> OTHER INFORMATION: Residue is dT

<400> SEQUENCE: 28
uuucgacacc gaagcagagt t                                             21

<210> SEQ ID NO 29

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
aacatgctgg tcatcctcat                                                  20

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
aatagagccc tgtcaagagt                                                  20

<210> SEQ ID NO 31
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 31
cctggaaggg atgtgtgc                                                    18

<210> SEQ ID NO 32
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 32
aaaaaggcaa agaagtcaca tca                                              23

<210> SEQ ID NO 33
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 33
cgacuggagc acgaggacac ugacauggac ugaaggagua gaaa                       44

<210> SEQ ID NO 34
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 34
caggtaacac tgtaaggatc tccagc                                           26

<210> SEQ ID NO 35
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 35
```

-continued

```
ggacactgac atggactgaa ggagta                                              26

<210> SEQ ID NO 36
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 36
taaagaggca tgagagtctg tgggga                                              26

<210> SEQ ID NO 37
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 37
ccggatctgt aacaactggt ctgaga                                              26

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
tcaagtatgg caaggctgtg                                                     20

<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 39
gaggctctgc ttctgcatct                                                     20

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
accgtcttgg aactggtcac                                                     20

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
atgttccttg ttgggtcagc                                                     20

<210> SEQ ID NO 42
<211> LENGTH: 10
<212> TYPE: RNA
```

```
<213> ORGANISM: Artificial Sequence
<220> FEATURE:
<223> OTHER INFORMATION: Synthetic polynucleotide

<400> SEQUENCE: 42 uucgucugkg                                                                  10

<210> SEQ ID NO 43
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 43
aucgucuauu agucgcuggc                                                       20

<210> SEQ ID NO 44
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 44
uccuuggcuu uucgucugug                                                       20

<210> SEQ ID NO 45
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 45
gccuucguuu guuucgucca                                                       20

<210> SEQ ID NO 46
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 46
ucccggcucg uucgucugug                                                       20

<210> SEQ ID NO 47
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 47
uucgucauuu uucgucuggg                                                       20

<210> SEQ ID NO 48
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 48
ccuuucgucu guuucugcgc                                                       20
```

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
ttcttttttt tttttcgcgc            20

<210> SEQ ID NO 50
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 50
aaaggagggg gccgggtgcg            20

<210> SEQ ID NO 51
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 51
ccaccaaacc cggcctcttt            20

<210> SEQ ID NO 52
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 52
gggaacccaa aaaaaaaaaa            20

<210> SEQ ID NO 53
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 53
tccttcgttt tttgtctggc            20

<210> SEQ ID NO 54
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 54
atttggtccg ggcgcggctg            20

<210> SEQ ID NO 55
<211> LENGTH: 20
<212> TYPE: DNA
<213> ORGANISM: Artificial Sequence
<220> FEATURE:

<223> OTHER INFORMATION: Synthetic polynucleotide

<400> SEQUENCE: 55
gaaccgaagc acgcgtctca                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 56
cggaaacgaa caaaaaaaat                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic polynucleotidfe

<400> SEQUENCE: 57
tccttcgttt ttcgtctggg                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 58
attggggccg agtgtctggg                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 59
gaaccttagc gcgcctcctc                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 60
cggaaacgaa caaaaaaaat                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 61
tccttcgttt ttcgtctgtg                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 62
gttggggccg ggttcgtgtg     20

<210> SEQ ID NO 63
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 63
aaacctcagc acgtcggcga     20

<210> SEQ ID NO 64
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 64
cggaaaagaa caaaaaaaat     20

<210> SEQ ID NO 65
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 65
atcgtctatt agtcgctggc     20

<210> SEQ ID NO 66
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 66
tcttgggtcg tttcgctggc     20

<210> SEQ ID NO 67
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 67
gaacctcccg gcgttggcta     20

<210> SEQ ID NO 68
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 68
cggaaaagaa caaaaaaaat                                              20

<210> SEQ ID NO 69
<211> LENGTH: 35
<212> TYPE: RNA
<213> ORGANISM: Artificial Sequence
<220> FEATURE:
<223> OTHER INFORMATION: Synthetic polynucleotide

<400> SEQUENCE: 69
ggagcaaagc cgacauugca gcucguguac caggc                             35

<210> SEQ ID NO 70
<211> LENGTH: 29
<212> TYPE: RNA
<213> ORGANISM: Artificial Sequence
<220> FEATURE:
<223> OTHER INFORMATION: Synthetic polynucleotide

<400> SEQUENCE: 70
uucaaagccg acauugcagc ucguguacc                                    29

<210> SEQ ID NO 71
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 71
uacacgagcu gcaaugucgg cuuug                                        25

<210> SEQ ID NO 72
<211> LENGTH: 33
<212> TYPE: RNA
<213> ORGANISM: Artificial Sequence
<220> FEATURE:
<223> OTHER INFORMATION: Synthetic polynucleotide

<400> SEQUENCE: 72
uuuuuuuucg acauugcagc ucguguacca ggc                               33

<210> SEQ ID NO 73
<211> LENGTH: 27
<212> TYPE: RNA
<213> ORGANISM: Artificial Sequence
<220> FEATURE:
<223> OTHER INFORMATION: Synthetic polynucleotide

<400> SEQUENCE: 73
gccugguaca cgagcugcaa ugucggc                                      27

<210> SEQ ID NO 74
<211> LENGTH: 33
<212> TYPE: RNA
<213> ORGANISM: Artificial Sequence
<220> FEATURE:
<223> OTHER INFORMATION: Synthetic polynucleotide

<400> SEQUENCE: 74
uuuuuuuucg acauugcagc ucguguacca ggc                               33

<210> SEQ ID NO 75
<211> LENGTH: 27

-continued

```
<212> TYPE: RNA
<213> ORGANISM: Artificial Sequence
<220> FEATURE:
<223> OTHER INFORMATION: Synthetic polynucleotide

<400> SEQUENCE: 75
gccugguaca cgagcugcaa ugucggc                                          27

<210> SEQ ID NO 76
<211> LENGTH: 33
<212> TYPE: RNA
<213> ORGANISM: Artificial Sequence
<220> FEATURE:
<223> OTHER INFORMATION: Synthetic polynucleotide

<400> SEQUENCE: 76
uuuuuuuucg acauugcagc ucguguacca ggc                                   33

<210> SEQ ID NO 77
<211> LENGTH: 27
<212> TYPE: RNA
<213> ORGANISM: Artificial Sequence
<220> FEATURE:
<223> OTHER INFORMATION: Synthetic polynucleotide

<400> SEQUENCE: 77
gccugguaca cgagcugcaa ugucggc                                          27

<210> SEQ ID NO 78
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 78
cgacauugca gcucguguau u                                                21

<210> SEQ ID NO 79
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 79
uacacgagcu gcaaugucgg c                                                21

<210> SEQ ID NO 80
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 80
auugcagcuc guguaccagg c                                                21

<210> SEQ ID NO 81
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 81
```

```
gccugguaca cgagcugcaa u                                              21

<210> SEQ ID NO 82
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 82
ugcagcucgu guaccaggc                                                 19

<210> SEQ ID NO 83
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 83
cugguacacg agcugcaau                                                 19

<210> SEQ ID NO 84
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 84
cgacauugca gcucguguac c                                              21

<210> SEQ ID NO 85
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 85
uacacgagcu gcaaugucgg c                                              21
```

CELL-SPECIFIC INTERNALIZING RNA APTAMERS AGAINST HUMAN CCR5 AND USES THEREFORE

CROSS-REFERENCE TO RELATED APPLICATIONS

This application is a continuation of U.S. application Ser. No. 14/801,710 filed Jul. 16, 2015, which claims the benefit of U.S. Provisional Application No. 62/025,368 filed Jul. 16, 2014, the content of which is hereby incorporated in its entirety and for all purposes.

STATEMENT AS TO RIGHTS TO INVENTIONS MADE UNDER FEDERALLY SPONSORED RESEARCH OR DEVELOPMENT

This invention was made with government support under P01 AI099783 awarded by the National Institutes of Health. The government has certain rights in this invention.

REFERENCE TO A "SEQUENCE LISTING," A TABLE, OR A COMPUTER PROGRAM LISTING APPENDIX SUBMITTED AS AN ASCII FILE

The Sequence Listing written in file 48440-544001US_ST25.TXT, created Jun. 1, 2016, 18394 bytes, machine format IBM-PC, MS-Windows operating system, is hereby incorporated by reference.

FIELD OF THE INVENTION

The present invention relates to novel aptamers. In one aspect, the invention relates to aptamers which target human CCR5. In another aspect, the invention relates to methods employing the aptamers described herein. In yet another aspect, the invention relates to compositions containing the aptamers described herein. In still another aspect, the invention relates to methods employing the aptamer-containing compositions described herein. In a further aspect, the invention relates to complexes comprising the aptamers described herein.

BACKGROUND OF THE INVENTION

Nucleic acid-based therapeutics are quickly emerging and have been considered as an alternative or adjuvant to the chemical antiviral agents currently used to treat HIV-1/AIDS. The combinatorial use of various antiviral nucleic acids could be more efficacious in blocking viral replication and preventing the emergence of resistant HIV-1 variants (1,2). Additionally, owing to their favorable characteristics, such as small size, high stability (dehydrated form), lack of immunogenicity, facile chemical synthesis, adaptable modification and cell-free evolution, highly specific nucleic acid-based aptamers and aptamer-functionalized agents have been used extensively for targeted disease therapy (3-7}.

To date, many nucleic acid aptamers specific to various parts of the HIV-1 genome and HIV-1 dependent proteins, including HIV-1 reverse transcriptase (RT), integrase (IN), nucleocapsid (NC), Gag, TAR, Rev, Tat, envelope gp120 and CD4 protein, have been raised through the purified protein-based SELEX method and shown to effectively suppress viral replication (3,8,9). Importantly, a number of cell-specific aptamers targeting cell surface proteins have been adapted as promising delivery vehicles for the targeted delivery of small interfering RNA (siRNA) in a cell-type-specific manner (10,11). The potential combined use of siRNAs and aptamers is intriguing as it could effectively block viral replication and prevent the emergence of resistant variants (12).

In previous studies, anti-HIV gp120 aptamers were combined with anti-HIV siRNAs to achieve a dual-inhibitory drug capable of delivering siRNAs selectively to HIV-infected cells as well as inhibiting viral entry via blocking of the envelope interaction with the CD4 (13-15).

SUMMARY OF THE INVENTION

In accordance with the present invention, there are provided combinatorial uses of various antiviral nucleic acids (such as small interfering RNAs (siRNAs) and aptamers), which are shown to be more efficacious in blocking viral replication and preventing the emergence of resistant variants. By combining the "Live Cell-based SELEX" strategy with high throughput sequencing (HTS) technology and bioinformatics analysis, several 2'-Fluoropyrimidine modified RNA aptamers targeted to the human CCR5 have been successfully identified.

One of the best candidates (G-3 aptamer) efficiently bound and was internalized into human CCR5 expressing cells. This G-3 aptamer specifically neutralized R5 virus infection in primary PBMCs with a nanomolar $IC_{50}$ value and was capable of shuttling functional siRNAs to CCR5 expressing cells. The data presented here suggest that CCR5 RNA aptamers can not only identify HIV-1 susceptible cells, but also selectively regulate both the inhibition of the CCR5 required for HIV-1 to enter cells and targeted anti-HIV siRNA delivery. Collectively, the cell-specific, internalizing CCR5 aptamers and aptamers-siRNA conjugates described herein offer great promise for cell-type- or tissue-specific delivery of various therapeutic drugs for targeted therapy.

Human CCR5 (C-C chemokine receptor type 5), a 7 pass transmembrane receptor expressed by T-cells and macrophages, serves as a co-receptor for macrophage-tropic HIV-1. A loss of CCR5 is associated with resistance to HIV-1. Thus, CCR5 is an important co-receptor for macrophage-tropic virus, including HIV-1 R5 isolates (16,17). Variations in CCR5 are associated with resistance or susceptibility to HIV-1. As an essential factor for viral entry, CCR5 has represented an attractive cellular target for the treatment of HIV-1 (18,19). Accordingly, the development of anti-CCR5 RNA aptamers to target HIV-1 susceptible cells, and specifically regulate both gene silencing of HIV-1 and block of the CCR5 required for HIV-1 to enter cells would be highly desirable.

Live Cell-based SELEX (Systematic Evolution of Ligand EXponential enrichment) is a promising approach for identifying aptamers that can selectively bind to a cell-surface antigen or a particular target cell population (11,20,21). By combining the "Live Cell-based SELEX" strategy (see FIG. 1A) with high throughput sequencing (HTS) and bioinformatics analysis, several 2'-Fluoropyrimidine modified RNA aptamers targeting the human CCR5 have successfully been identified. One of the best candidates (G-3 aptamer) efficiently bound and was internalized into human CCR5 expressing Magi-U373-CCR5E cells, CEM-NKr-CCR5 cells and primary PBMCs that were isolated from different donors. Moreover, G-3 aptamer specifically neutralized R5 virus infection in primary PBMCs with a nanomolar $IC_{50}$ value and was capable of delivering functional siRNAs to cells in a receptor-targeted manner. Collectively, the derivation and mechanistic characterization of new CCR5 targeted aptamers, which may prove useful in several applications as well as therapeutically, is described herein.

After 5~10 selection cycles, individual aptamer sequences are identified through barcode-based high throughput, Illumina Deep Sequencing (HTS) and bioinformatics analysis.

Figure 1A:
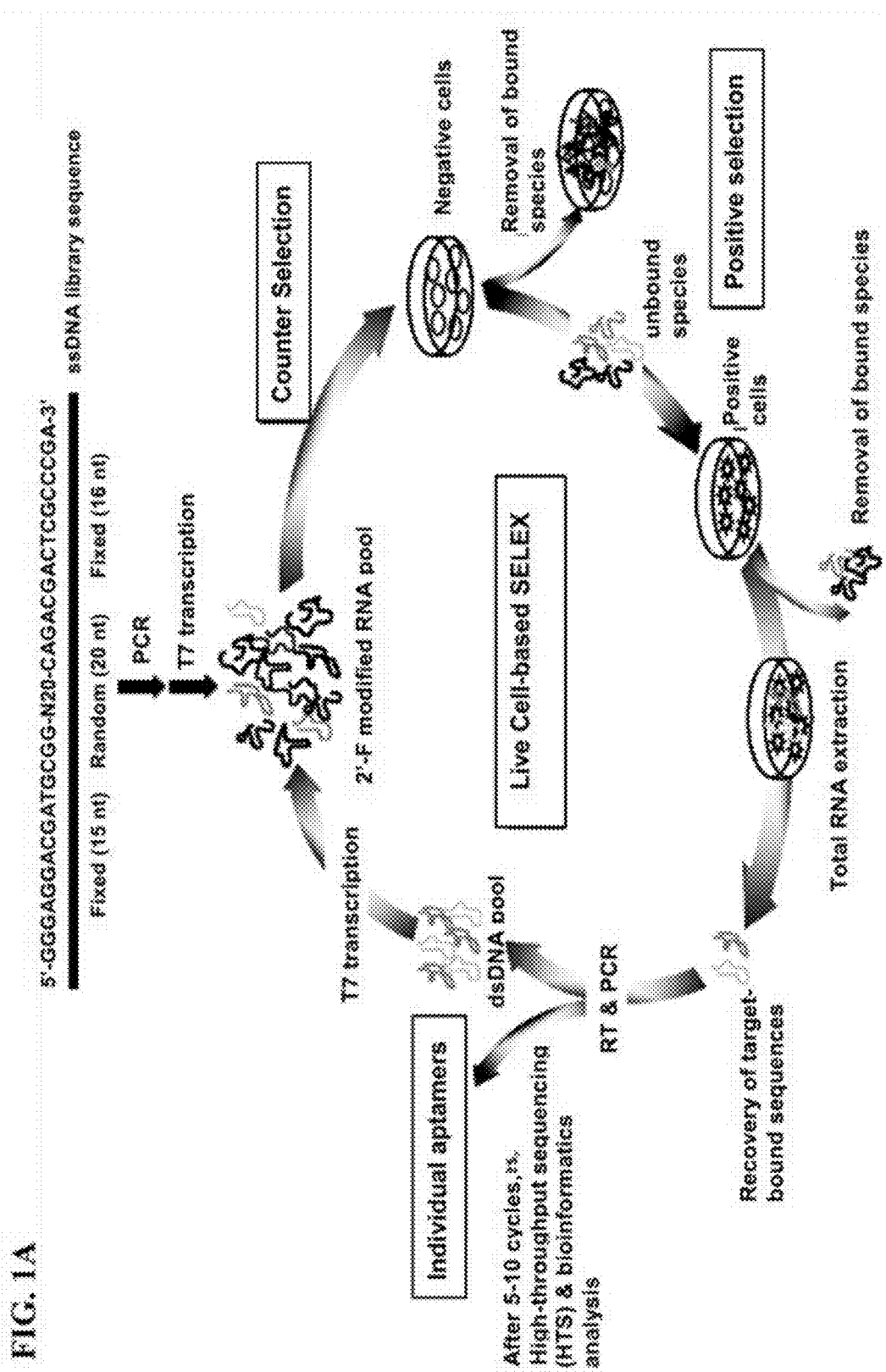
FIG. 1A is a schematic of live cell-based SELEX procedure for evolution of RNA aptamers. It consists of four main steps:
1) counter selection by incubating library with negative cells that do not express the target protein;
2) positive selection by incubating recovered unbound sequences with positive cells expressing the target protein;
3) recovery of target-bound sequences; and finally
4) re-amplification of recovered species and make new RNA pool for next selection round.
Figure 1B:
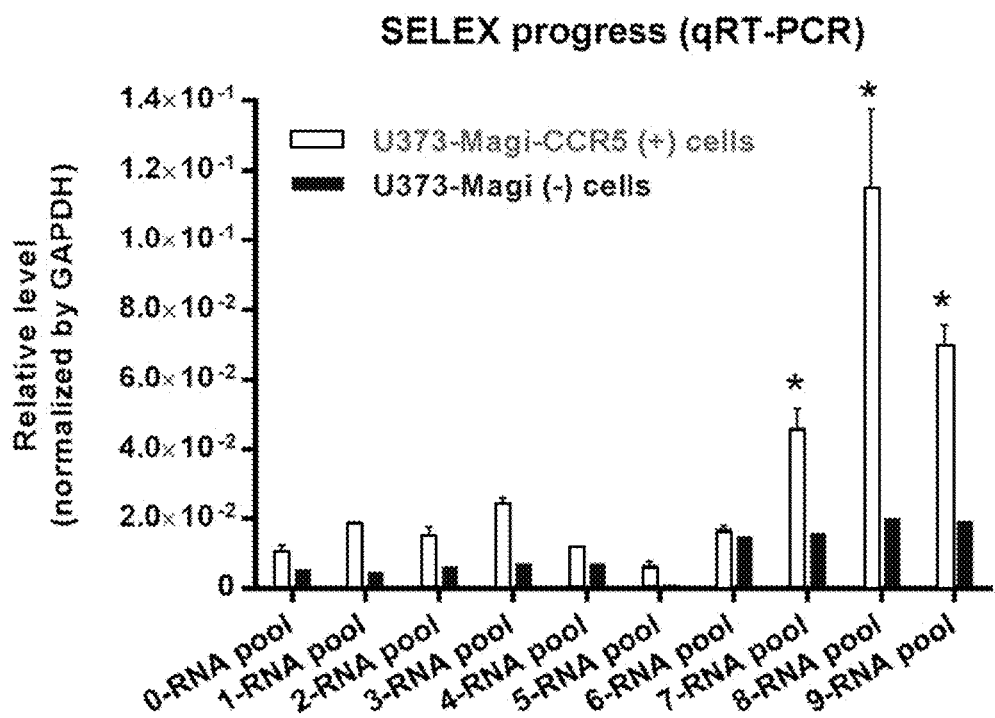

FIG. 1B illustrates the progress of SELEX. Progression of the selection was monitored using quantitative RT-PCR (qRT-PCR) and normalizing to GAPDH gene. Nine rounds of live cell-based SELEX were performed to enrich for RNA aptamers that bind and internalize into U373-MAGI-CCR5E (CCR5) cells. Non-specific aptamers were removed by pre-clearing against U373-MAGI (CCR5) cells. From the seventh selection round, selective binding/internalization of RNA pools was observed in U373-MAGI-CCR5E (CCR5) cells.

Figure 2A:
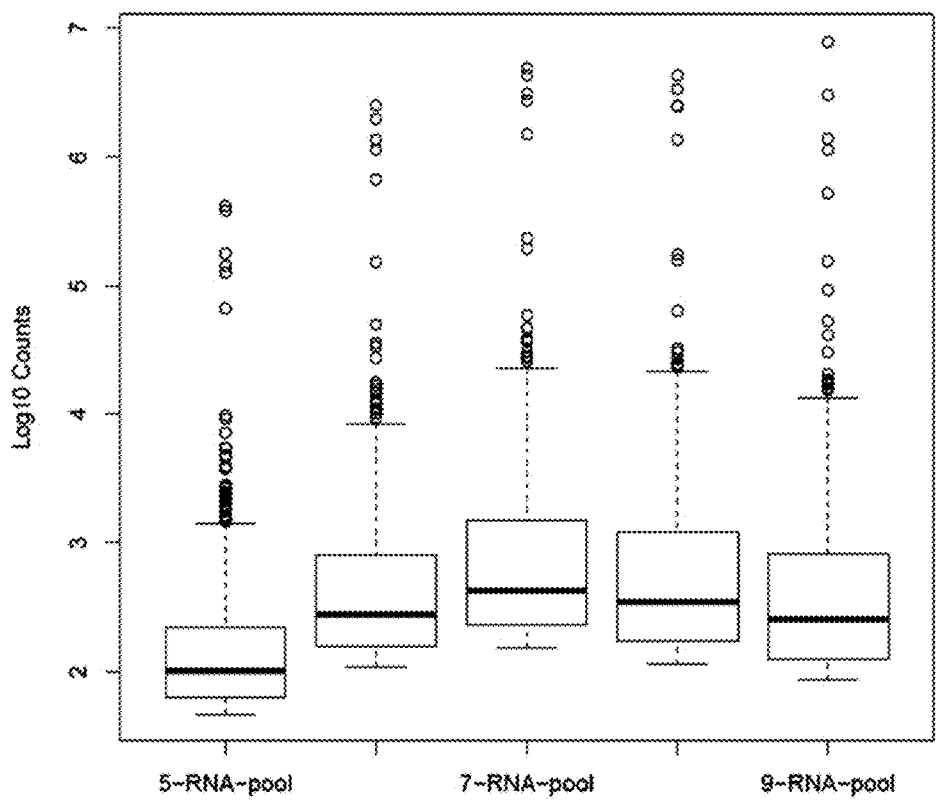

FIG. 2A-2H collectively summarizes the bioinformatics analysis of high throughput sequence data from selection rounds. FIG. 2A presents the distribution of frequencies of the top 1000 unique sequences at each round. The most frequent 1,000 unique sequences were identified at each selection round. From Round 7, enrichment saturation was observed.

Figure 2B:
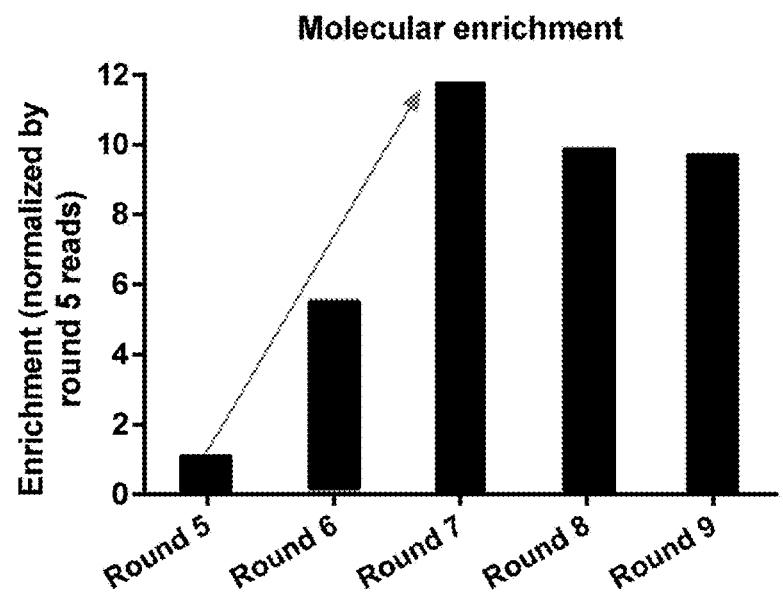

FIG. 2B illustrates the molecular enrichment at each round, which was calculated by the formula:

total reads of top 1000 sequences in round X/round 5.

From round 5 to Round 9, the molecular diversity was significantly converged, suggesting that some specific sequences have been enriched.

Figure 2C:
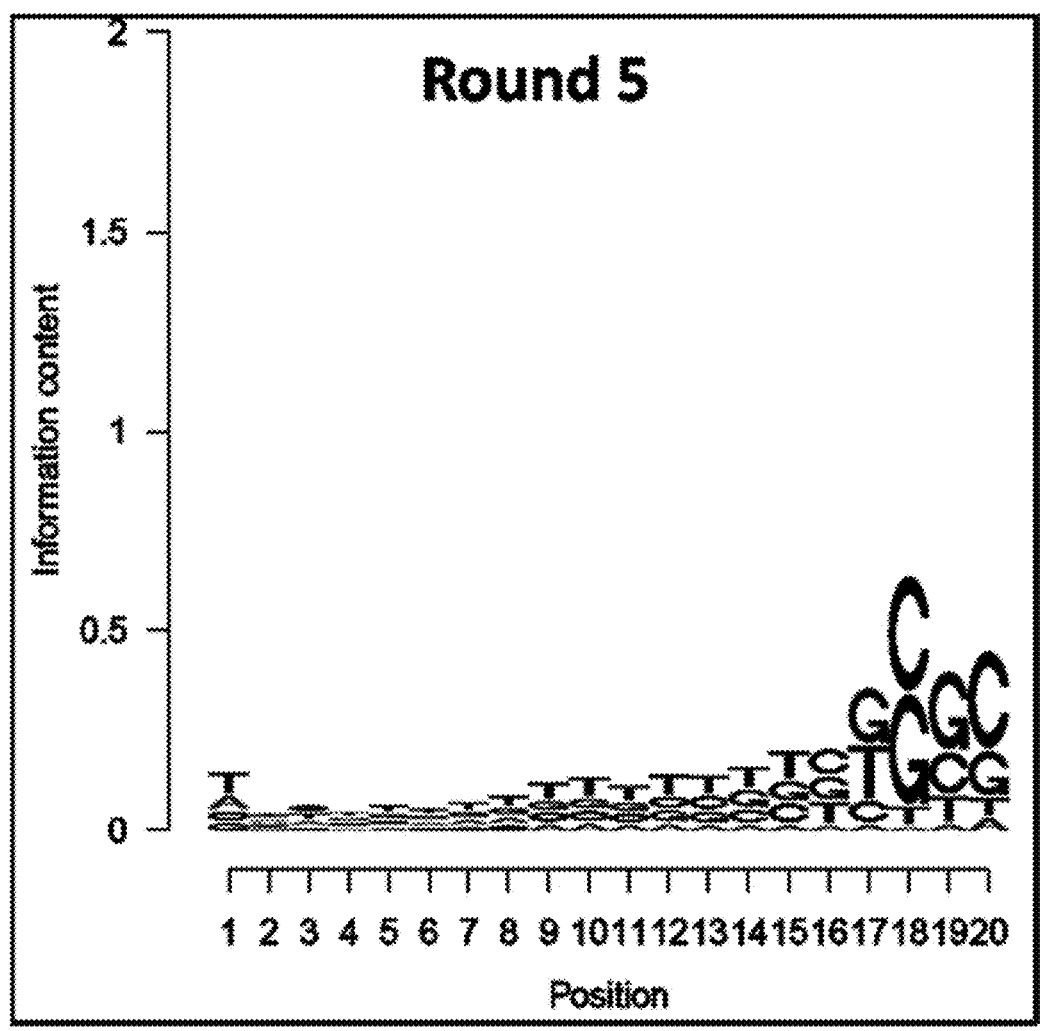
Figure 2D:
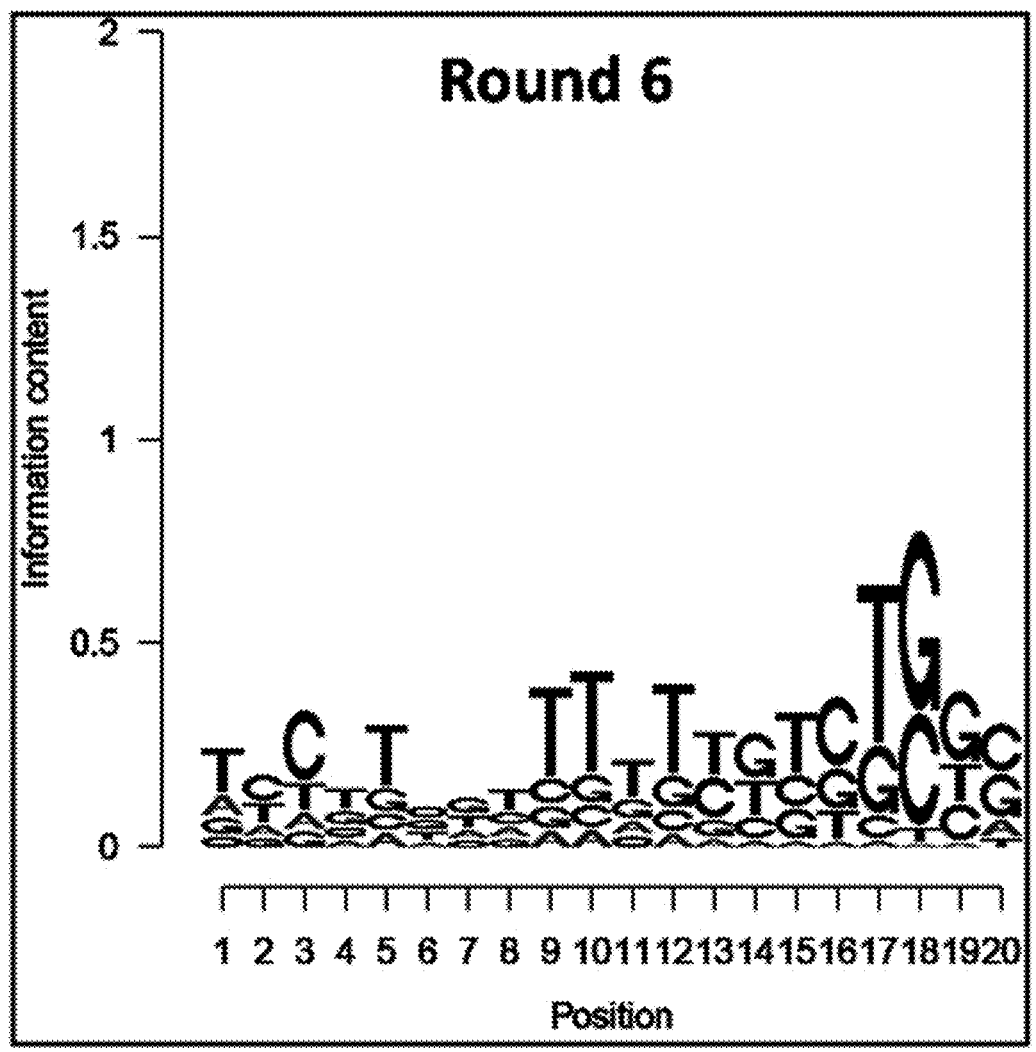
Figure 2E:
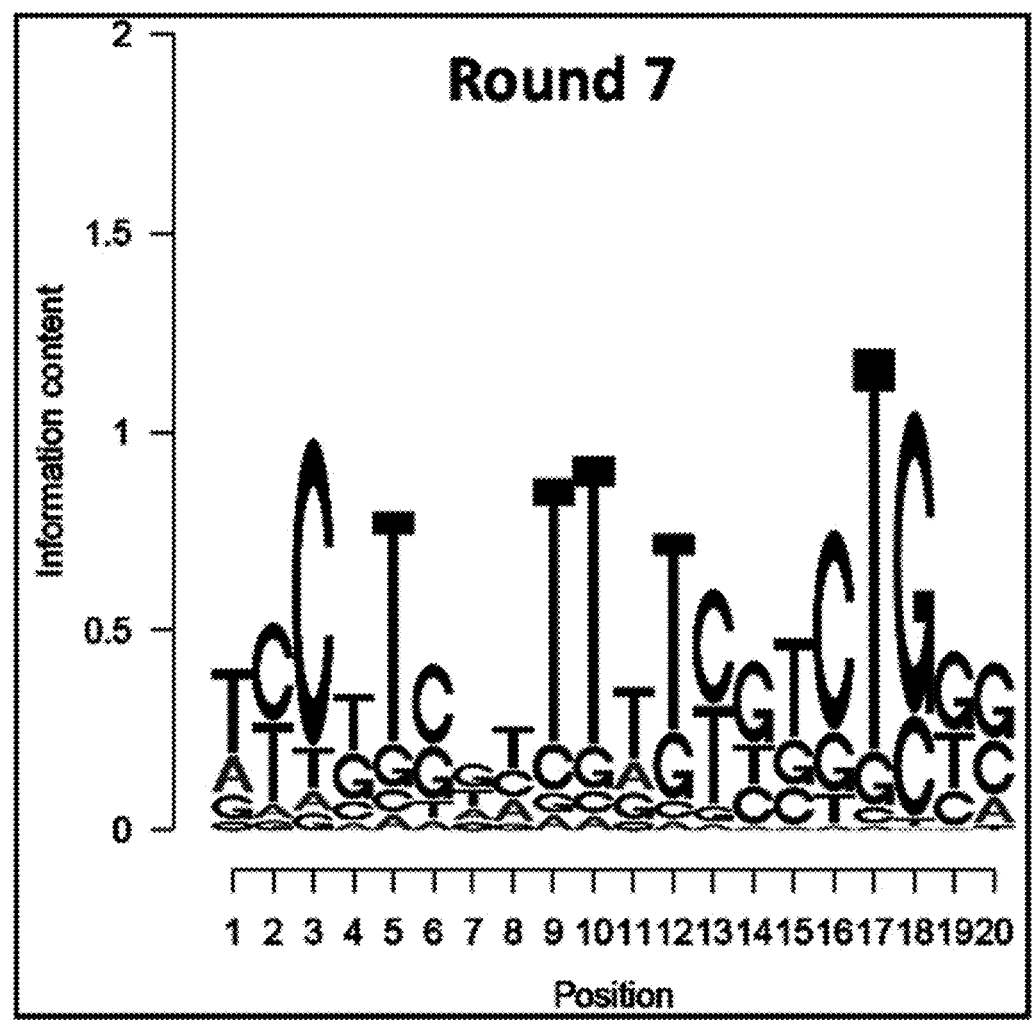
Figure 2F:
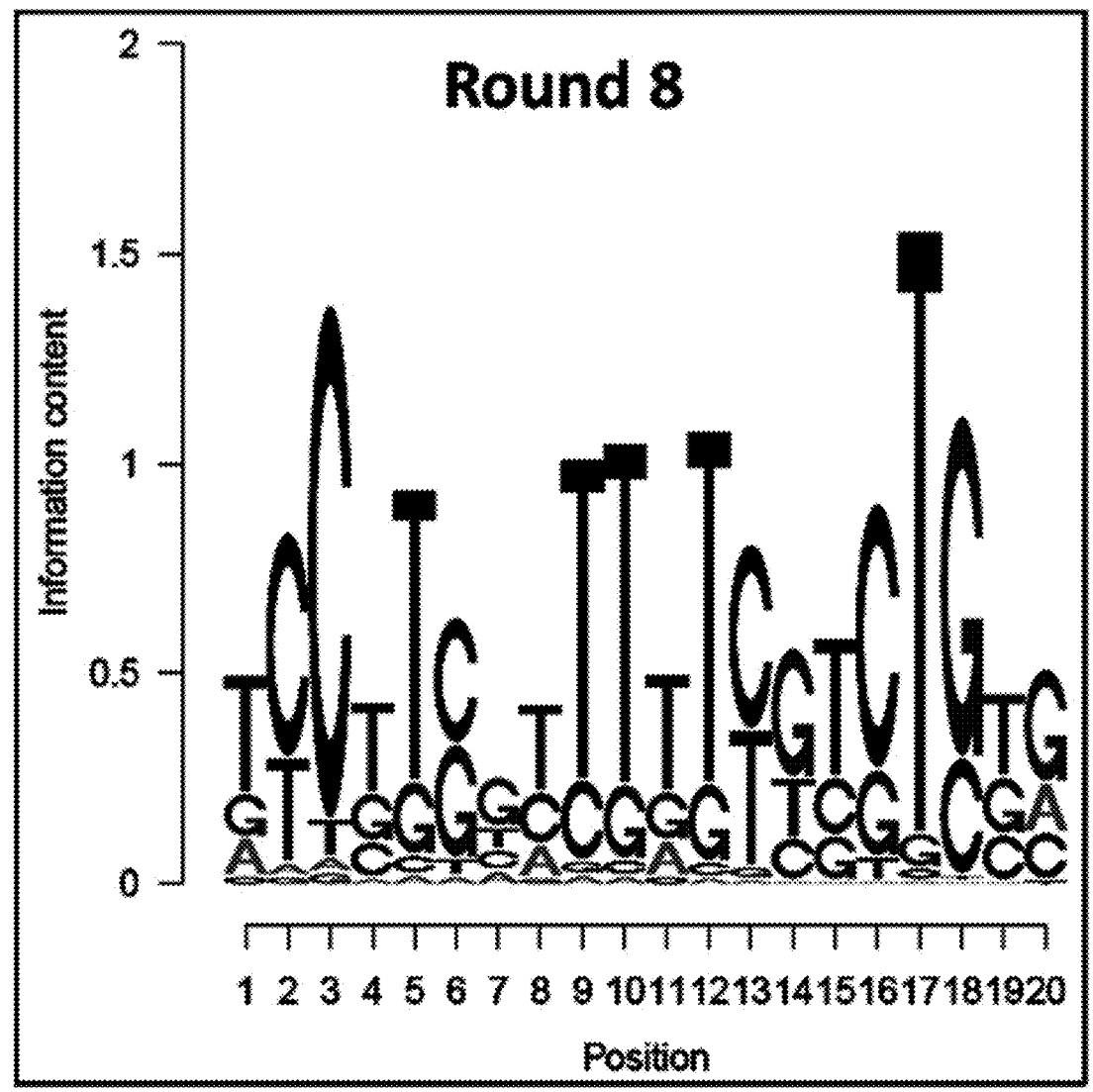
Figure 2G:
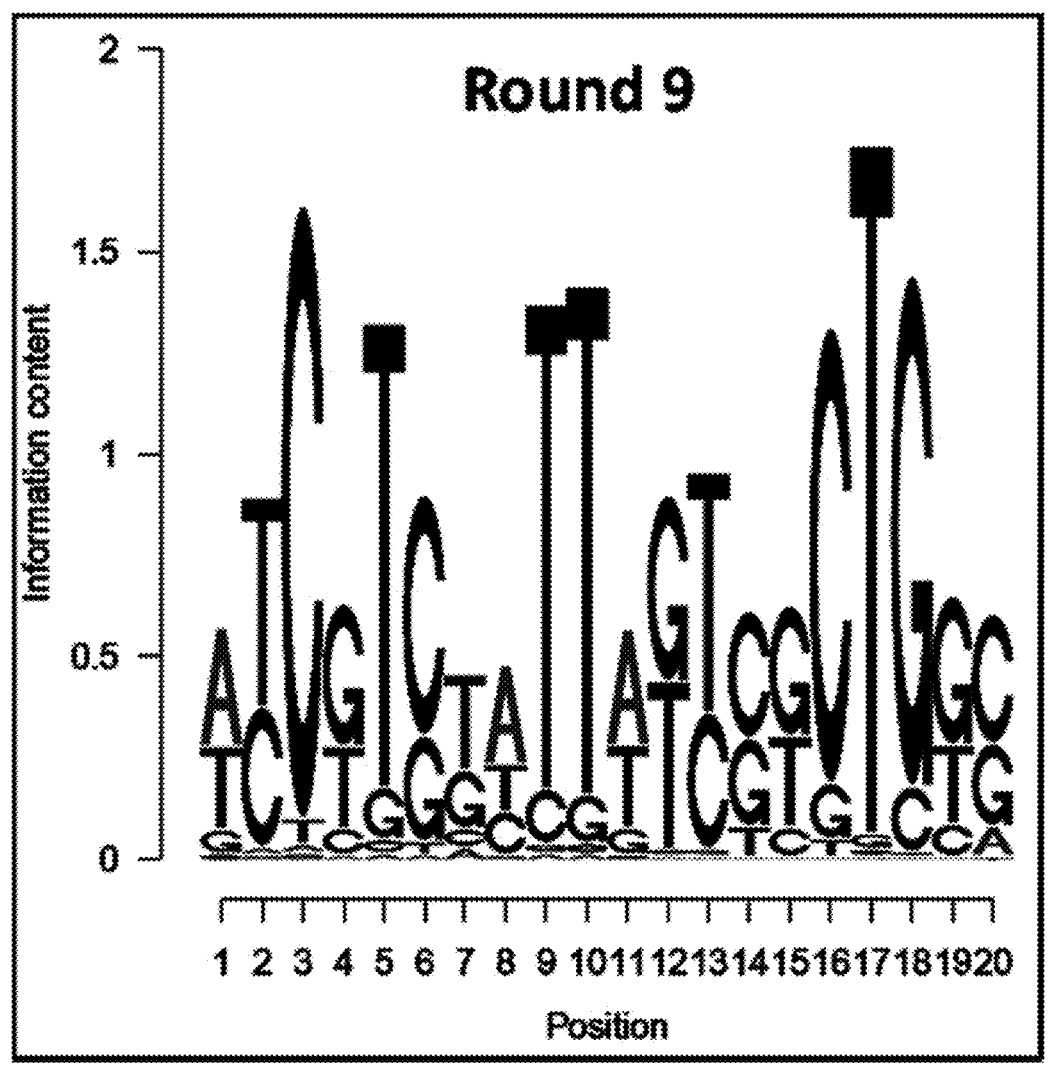

FIG. 2C-2G present sequence logos for each select round. Bioinformatics analysis of RNA aptamers was used to identify related sequence and structure families. Through the alignment of primary sequences, the distributions within each round were identified at the 20-nt random domain. From Round 7, highly represented sequences were observed. Legend: FIG. 2C: Round 5; FIG. 2D: Round 6; FIG. 2E: Round 7; FIG. 2F: Round 8; FIG. 2G: Round 9. Sequence legend: FIG. 2C (top to bottom): SEQ ID NOS:49-52; FIG. 2D (top to bottom): SEQ ID NOS:53-56; FIG. 2E (top to bottom): SEQ ID NOS:57-60; FIG. 2F (top to bottom):SEQ ID NOS:61-64; FIG. 2G (top to bottom): SEQ ID NOS: 65-68.

Figure 2H:
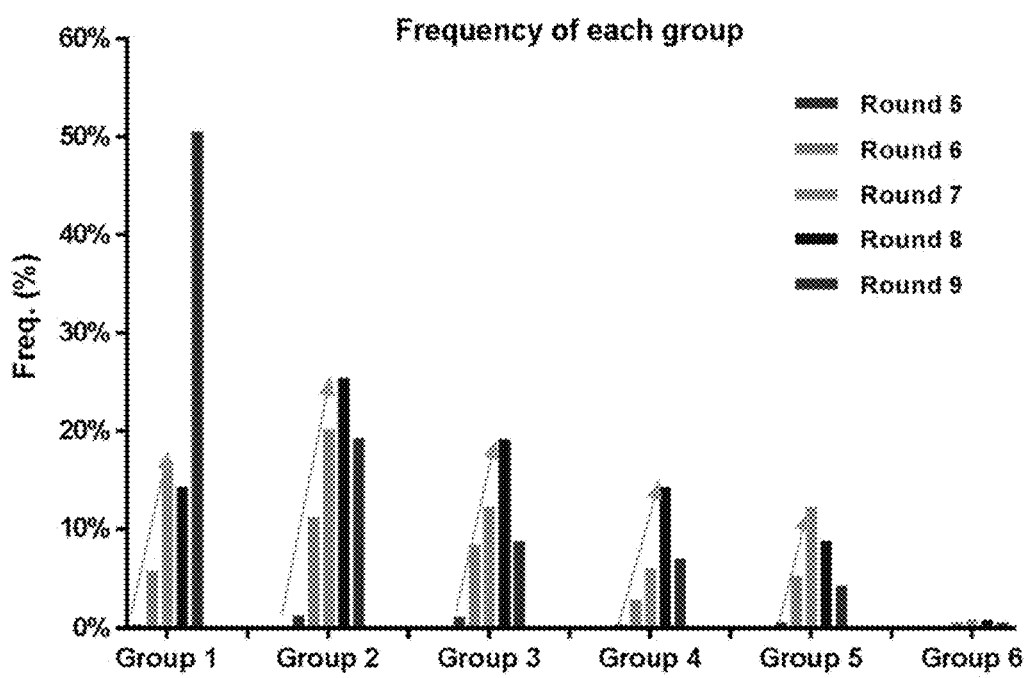

FIG. 2H summarizes the frequency of each group at each selection round. After alignment of the top 40 sequences, six groups of RNA aptamers were identified. The percent frequency of each group at each selection round was calculated by the formula:

the reads of each group the useful reads at each round.

FIG. 3A-3H collectively summarizes cell-type specific binding and internalization studies of individual RNA aptamers.

Figure 3A:
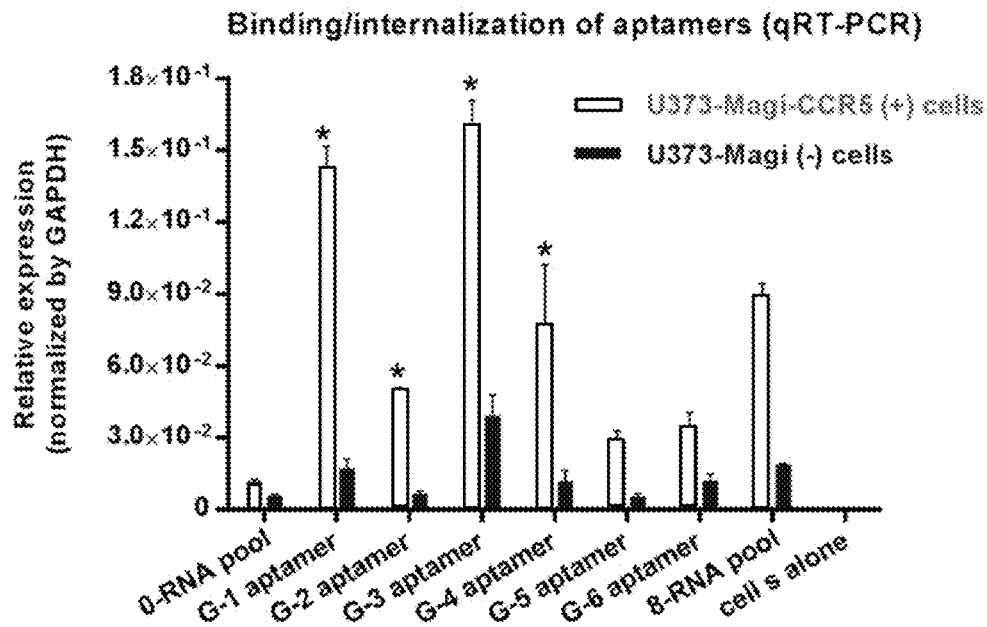

FIG. 3A summarizes the evaluation of cell-type specific binding/internalization by qRT-PCR. Six representative RNA aptamers from each group were incubated with U373-Magi-CCR5E (CCR5 positive) cells or U373-Magi negative cells. The total RNA was isolated for cDNA synthesis, followed by qPCR amplification. The RNA aptamers showed selective binding/internalization to CCR5 expressing cells. The 0-RNA pool was used as negative control. Data represent the average of three replicates. Cell surface binding of Cy3-labeled RNAs was assessed by flow cytometry.

Figure 3B:
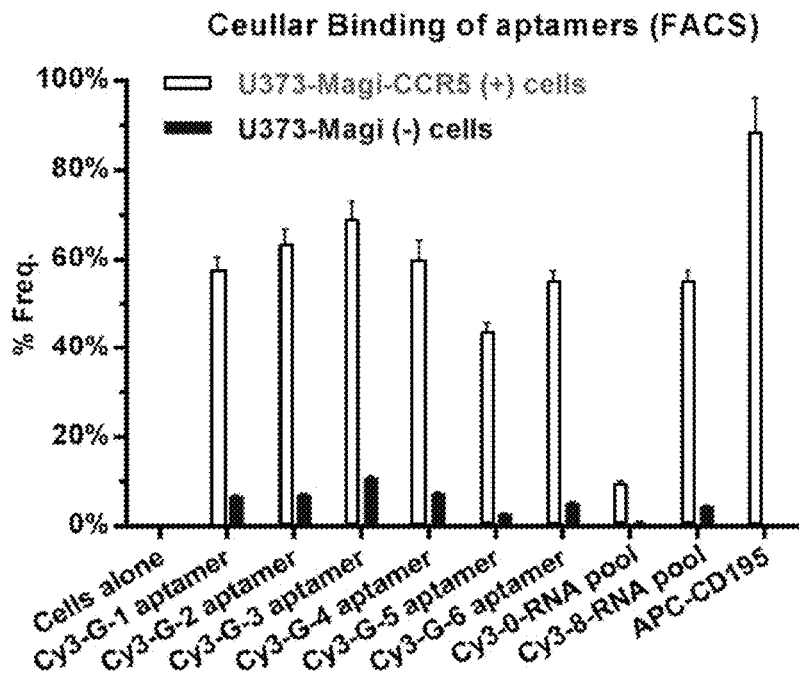

FIG. 3B Cy3-labeled RNAs were tested for binding to U373-Magi-CCR5E (CCR5 positive) cells and U373-Magi (CCR5 negative) cells. The selected aptamers showed cell-type specific binding affinity. APC-CD195 antibody was used to stain cellular surface CCR5.

Figure 3C:
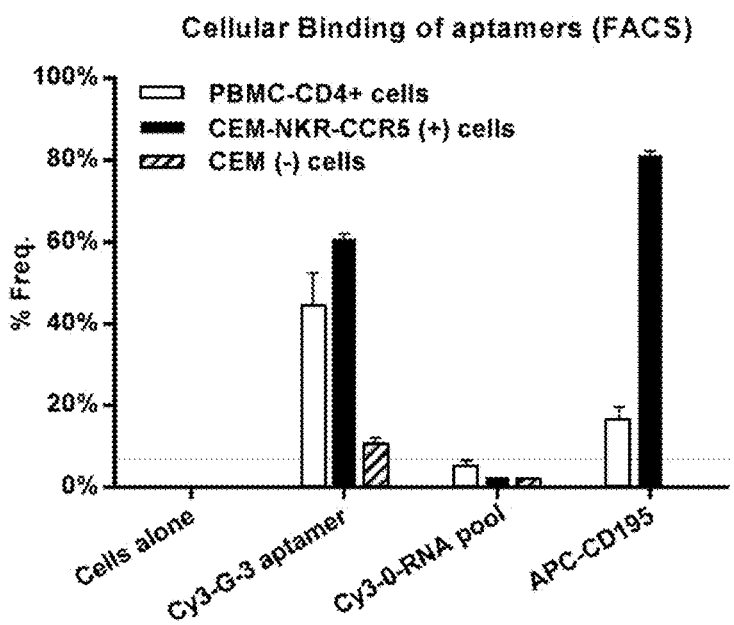

FIG. 3C One of the best RNA aptamers, G-3, was selected for further binding affinity tests with PBMC-CD4+ cells, CEM-NKr-CCR5 positive cells, CEM negative cells.

Figure 3D:
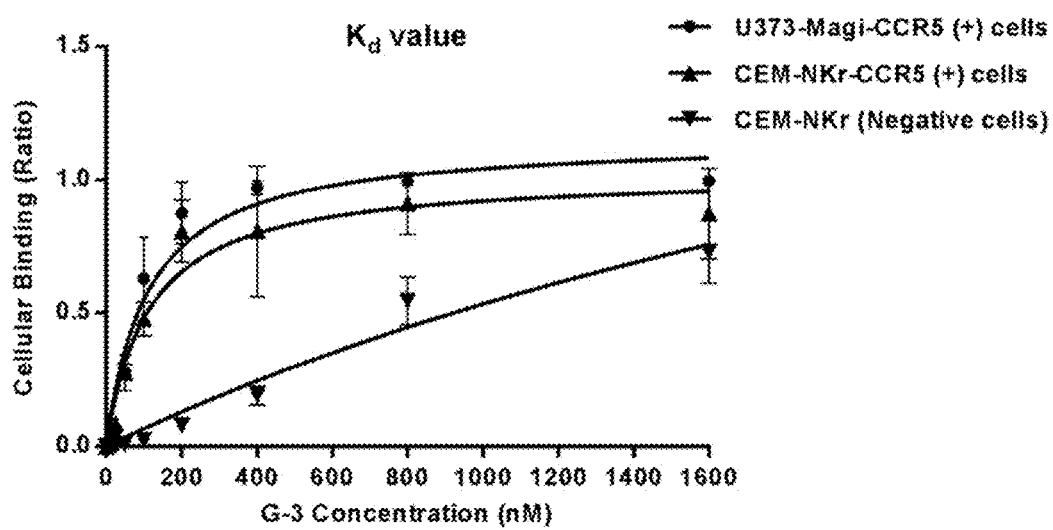

FIG. 3D C illustrates the evaluation of cell surface binding constant ($K_d$) of G-3 aptamer. The U373-Magi-CCR5E (CCR5 positive) cells, CEM-NKr-CCR5 positive cells and CEM negative cells were incubated with increasing amounts of Cy3-labeled G-3 aptamer. The binding affinity was analyzed by flow cytometry assay. The calculated $K_d$ determinations are summarized in the following table:

| Cells | Binding affinity ($K_d$ nM) | One site binding ($R^2$) |
| --- | --- | --- |
| U373-Magi-CCR5 (+) | 110.7 ± 22.7 nM | 0.95 |
| CEM-NKr-CCR5 (+) | 113.1 ± 28.2 nM | 0.92 |
| CEM-NKr negative | >3000 nM | 0.95 |

Figure 3E:
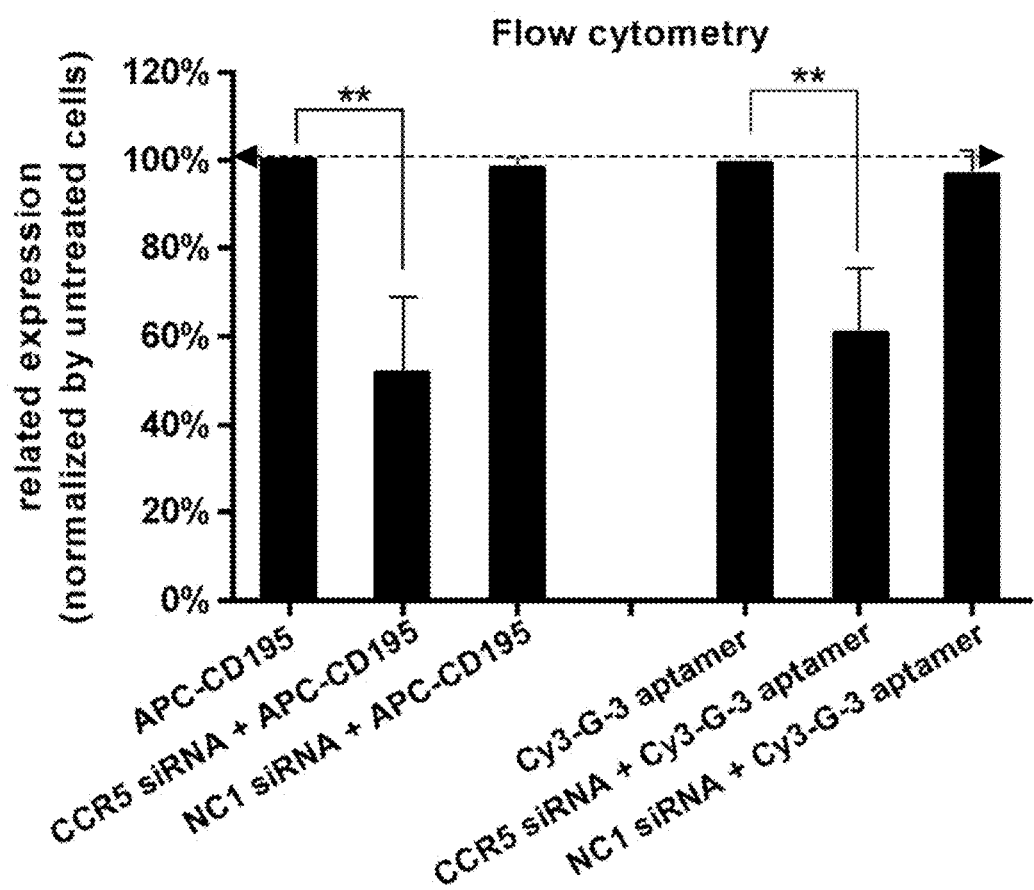

FIG. 3E demonstrates that knockdown of CCR5 reduced the binding affinity of aptamers. CCR5 siRNA was transfected into U373-Magi-CCR5E cells. After 48 hours post-transfection, cell surface binding of Cy3-labeled G-3 aptamer was assessed by flow cytometry. A scrambled siRNA (NC1) was used as negative control. Data represent the average of three replicates.

Figure 3F:
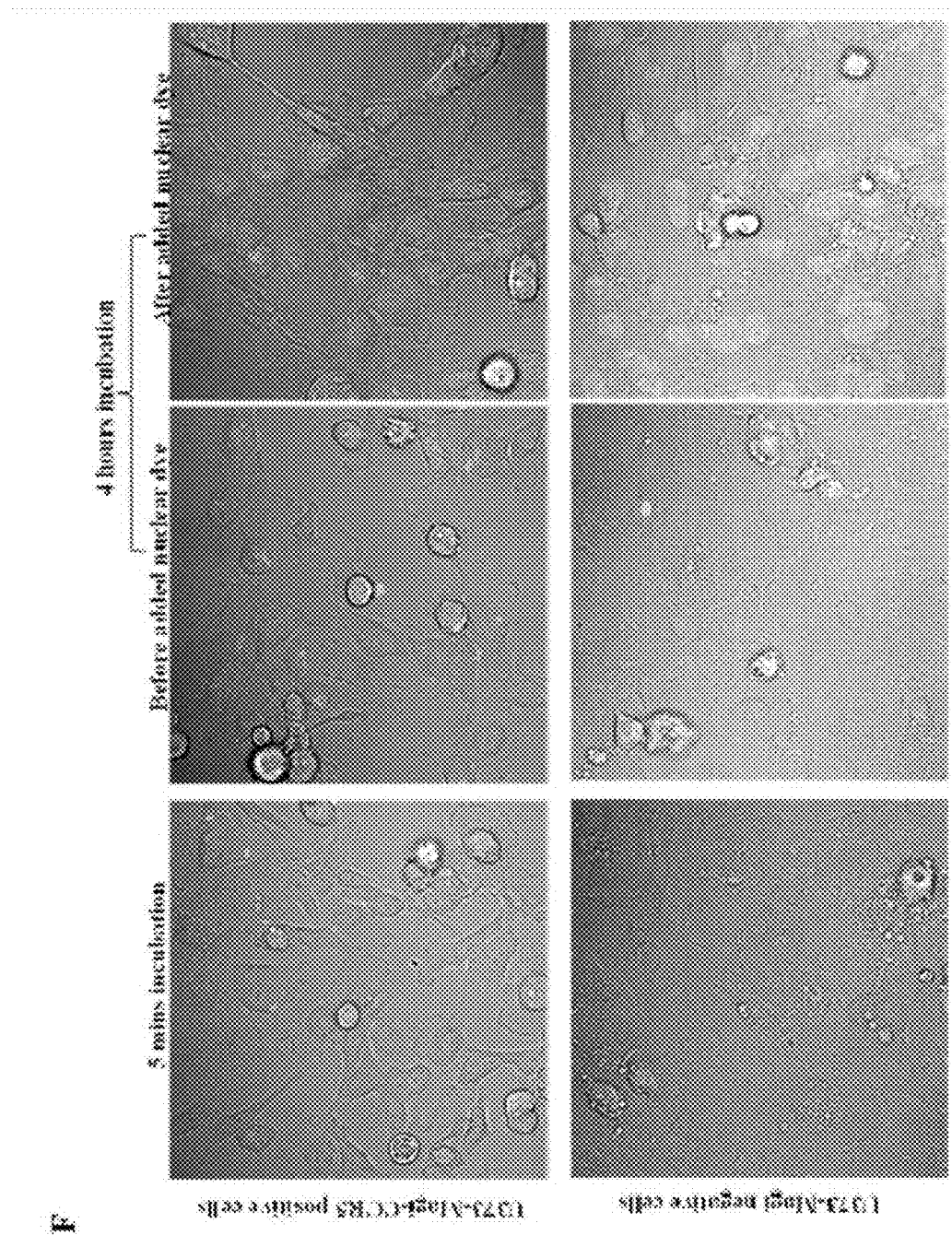
Figure 3F:
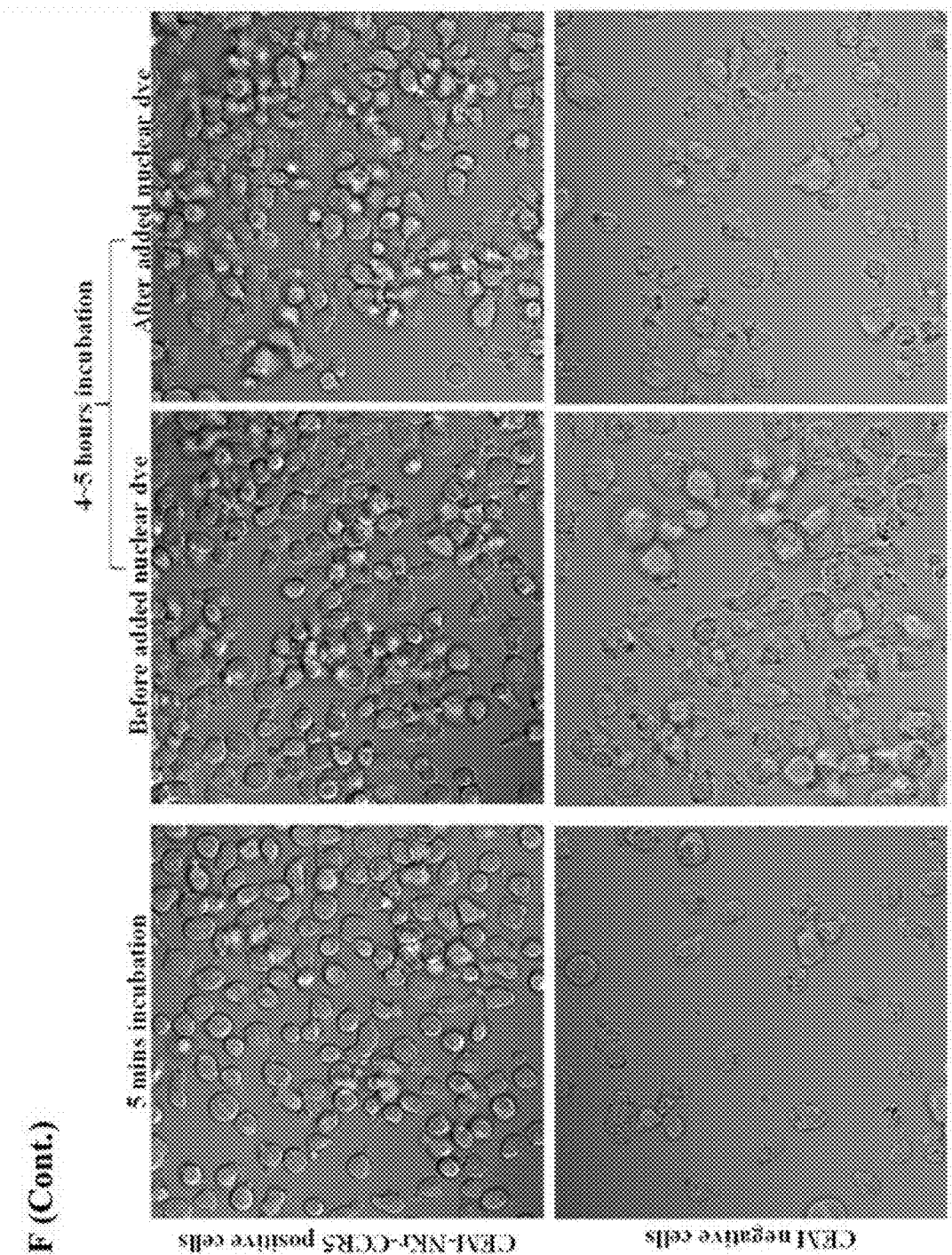

FIGS. 3F and 3F (cont'd) presents the results of internalization analysis with U373-Magi-CCR5E cells, U373-Magi negative cells, CEM-NKr-CCR5 positive cells, and CEM negative cells.

Figure 3G:
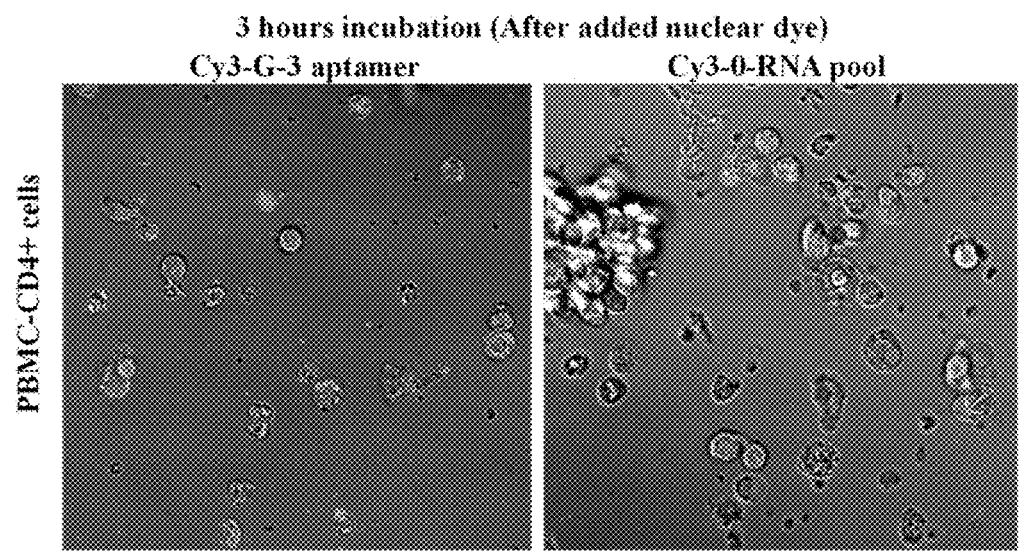

FIG. 3G presents the results of internalization analysis with PBMC-CD4+ cells, which were grown in 35 mm plates treated with polylysine and incubated with a 67 nM concentration of Cy3-labeled G-3 aptamer in complete culture media for real-time live-cell confocal microscopy analysis. The images were collected using 40×magnification.

Figure 3H:
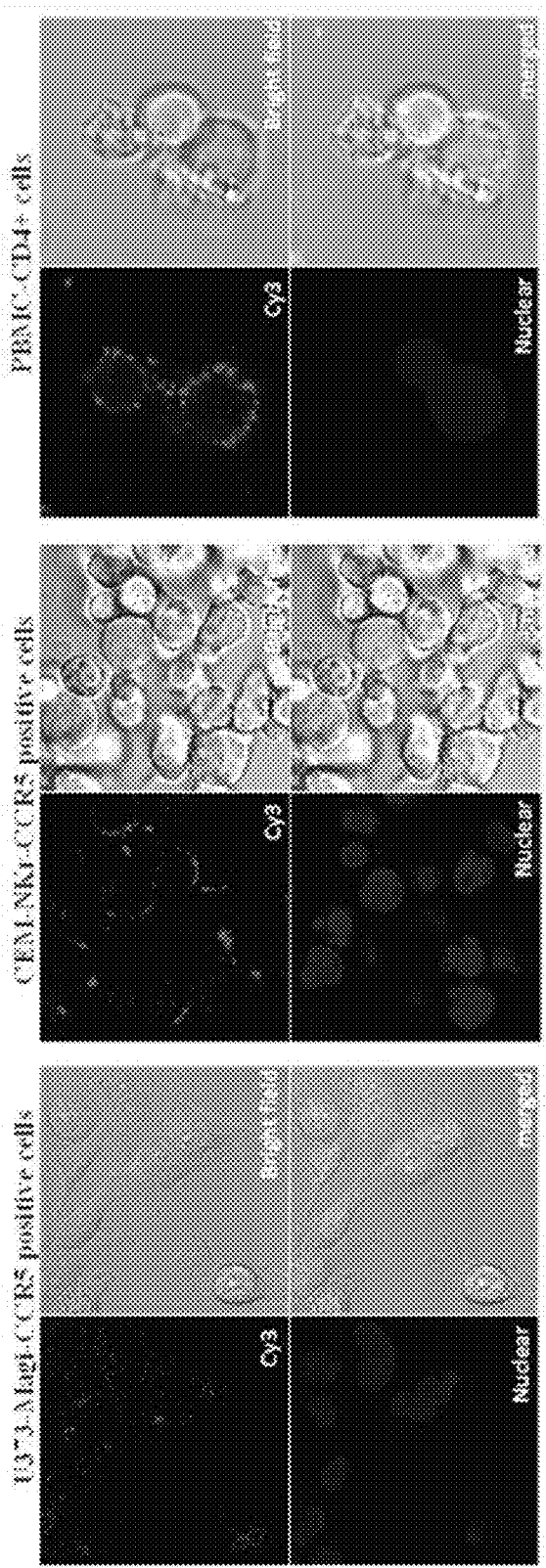

FIG. 3H presents a localization analysis.

Figure 4A:
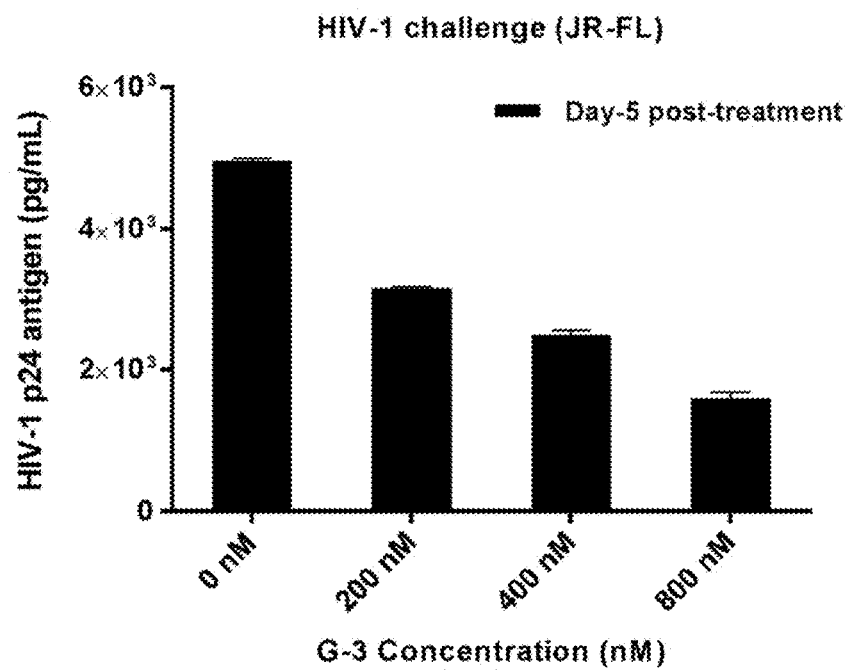
Figure 4B:
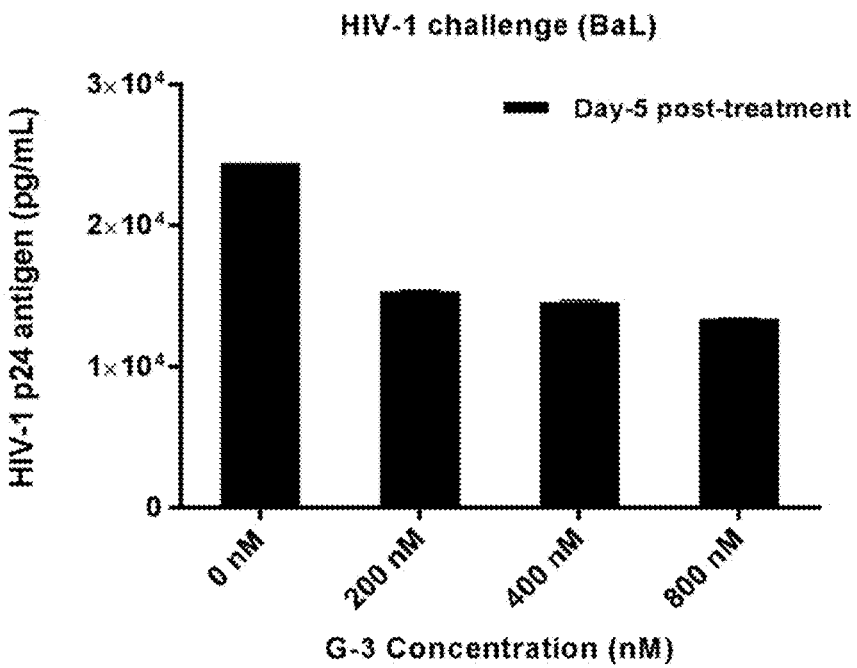
Figure 4C:
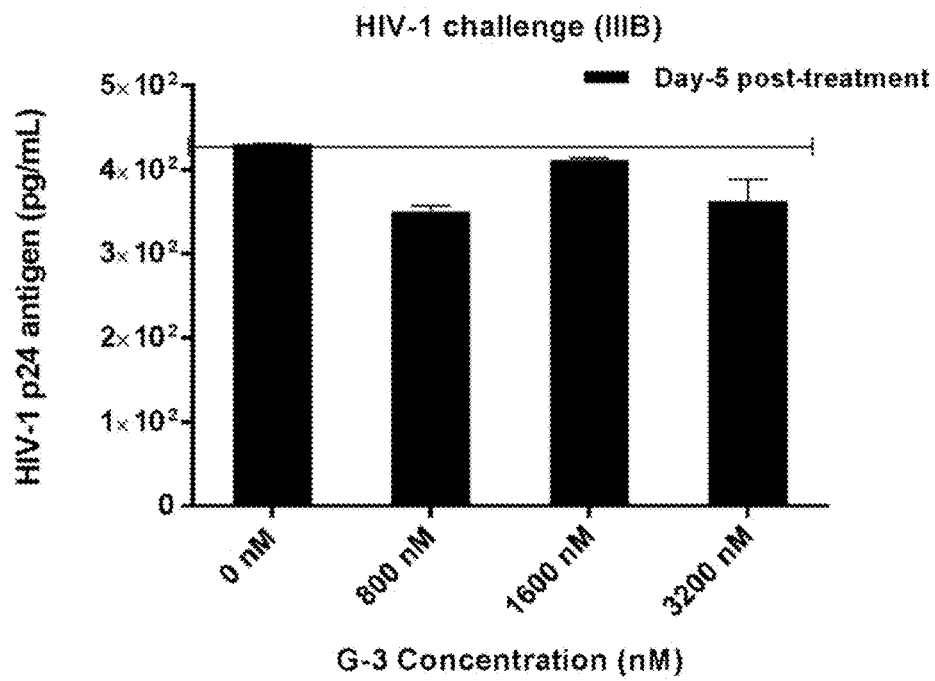
Figure 4D:
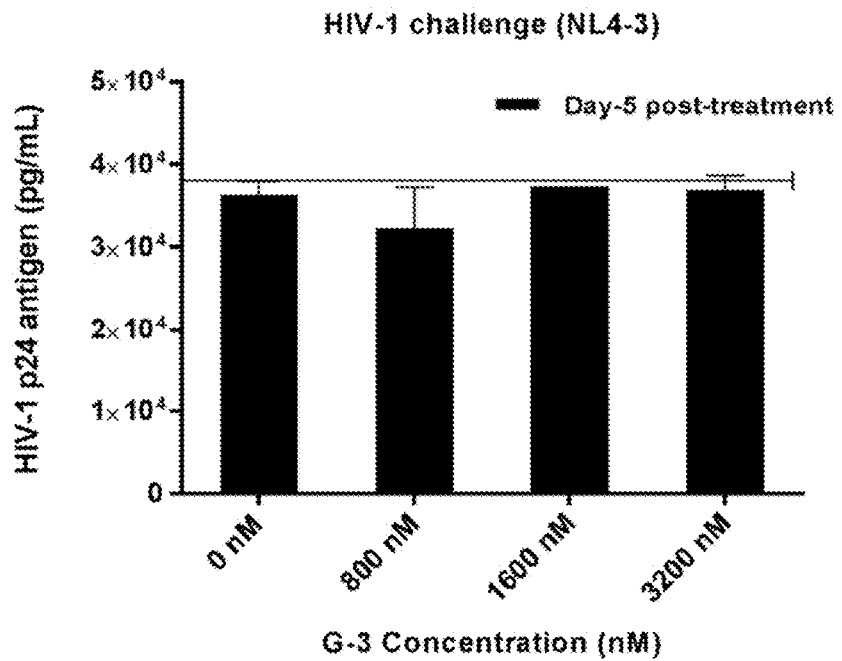

FIG. 4A-4D collectively illustrates the results of an HIV-1 challenge assay. G-3 aptamers with different concentrations were incubated with primary PBMCs. After 4-6 hours incubation, various viruses (R5 strains): FIG. 4A: JR-FL, FIG. 4B: Bal; or X4 strains: FIG. 4C: IIIB, FIG. 4D: NL4-3 were added into each well. The culture supernatants were collected at five days after treatment for HIV-1 p24 antigen ELISA assay.

FIG. 5A-5F collectively illustrates the design and binding affinity of aptamer-siRNA chimeras.

Figure 5A:
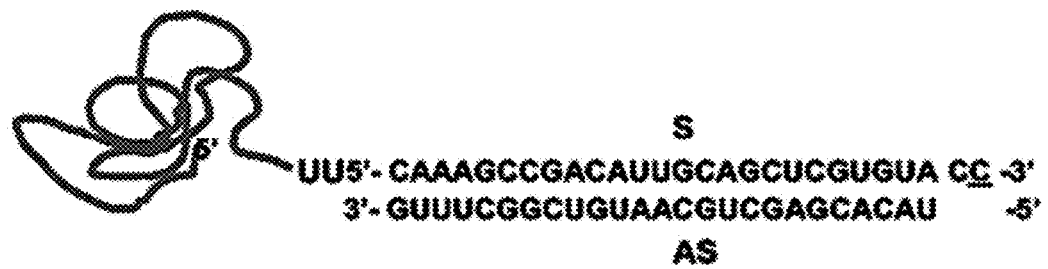
Figure 5B:
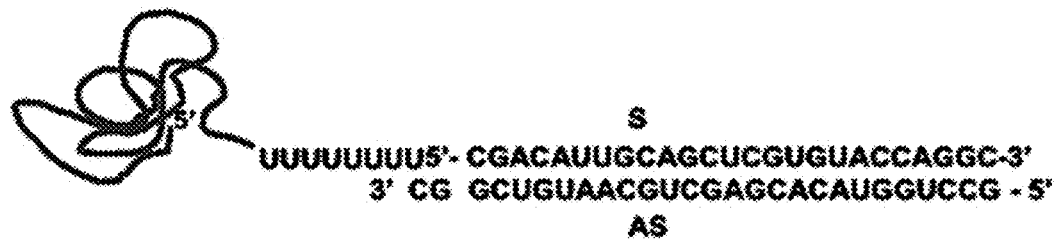

FIGS. 5A and 5B present a schematic of CCR5 aptamer (G-3)—siRNA chimeras. The region of the anti-CCR5 aptamer is responsible for binding to CCR5, and the siRNA targets the TNPO3 gene. A linker (2 or 8 Us) between the aptamer and siRNA is indicated in green. Two versions, G-3-27-mer-TNPO3 OVH chimera (SEQ ID NO:10 corresponds to sense strand SEQ ID NO:11 corresponds to antisense strand) (see FIG. 5A) and G-3-TNPO3 27-mer Blunt chimera (SEQ ID NO:12 corresponds to sense strand SEQ ID NO:13 corresponds to antisense strand) (see FIG. 5B), were designed, in which the DsiRNA portion is different.

Figure 5C:
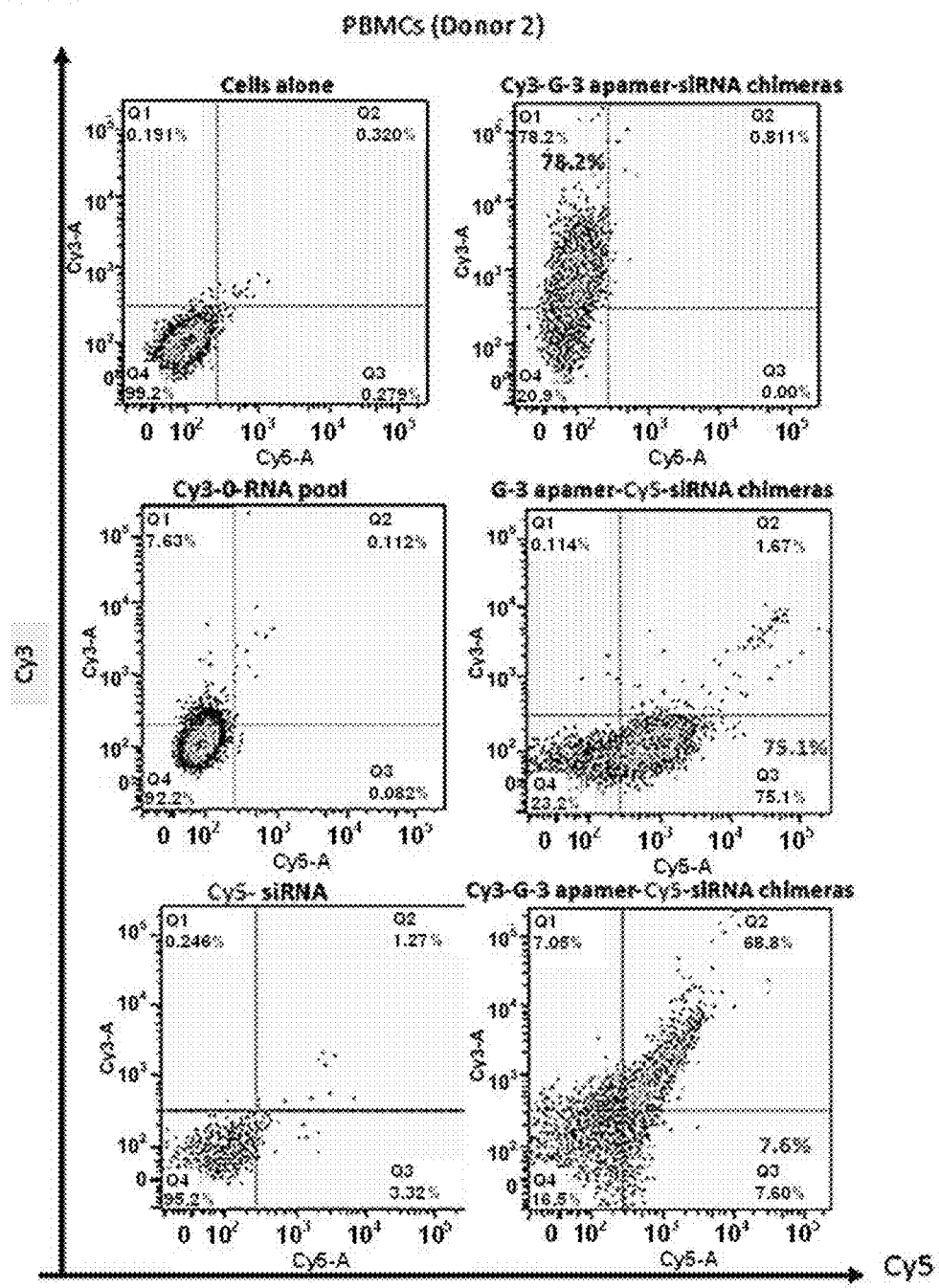
Figure 5D:
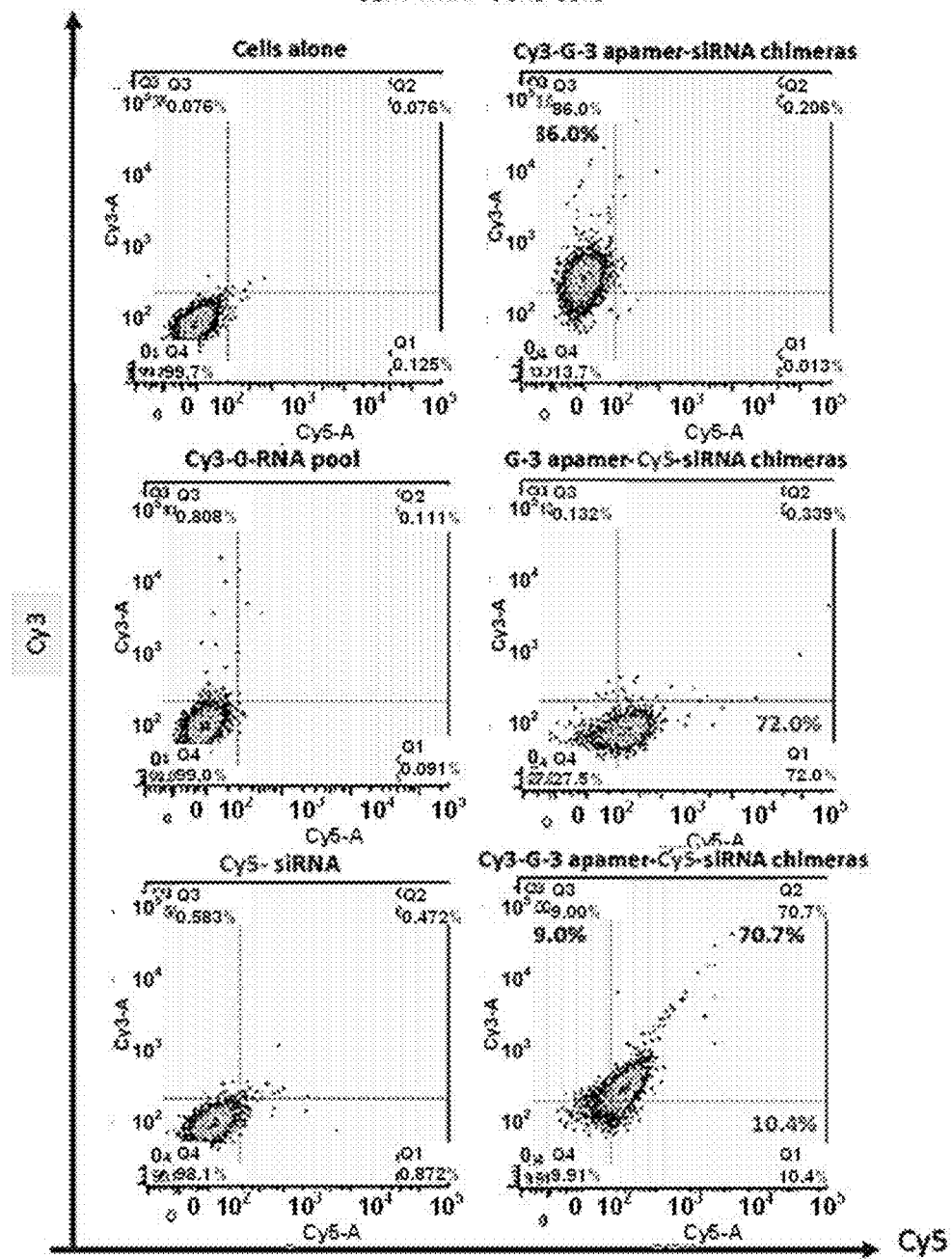
Figure 5E:
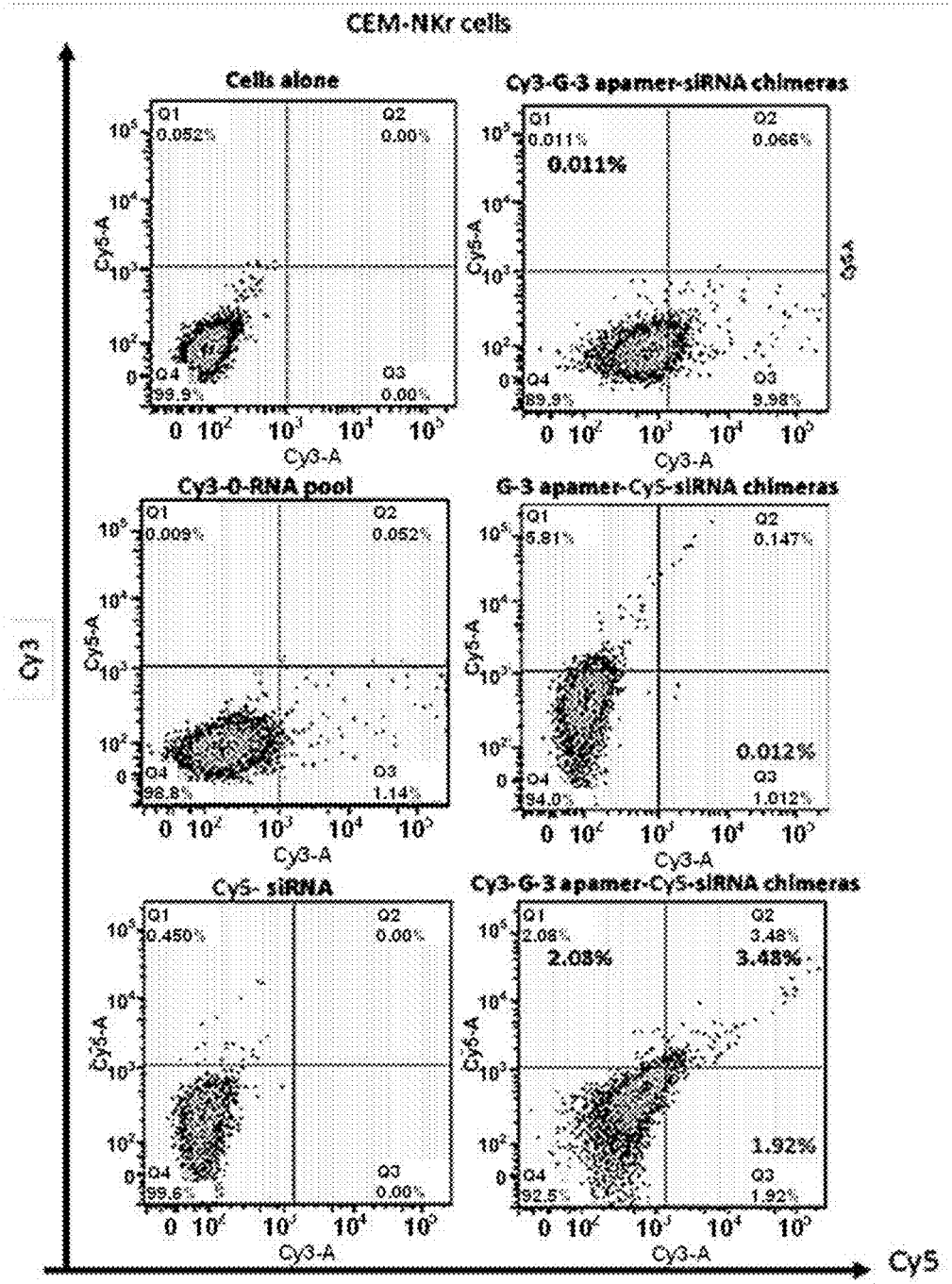

FIGS. 5C, 5D, and 5E illustrate cell surface binding of fluorescent dye—labeled RNAs was assessed by flow cytometry. The Cy3-labeled 0-RNA pool and Cy5-labeled siRNA were used as negative controls. G-3-27-mer-TNPO3 OVH chimera was chosen for the binding affinity test with PBMC-CD4+ cells (see FIG. 5C), CEM-NKr-CCR5 positive cells (see FIG. 5D), and CEM negative cells (see FIG. 5E). The aptamer-sense strand and antisense strand of the chimera were labeled by Cy3 and Cy5 dye, respectively. And then they were annealed to form aptamer-siRNA chimera. Experimental conditions for FIGS. 5C-5E are set forth in the table following:

FIG. 5C

| PBMCs (donor 2) | Cy3 positive (His %) | Cy5 positive (His %) | Both positive |
|---|---|---|---|
| Control | 0.191 | 0.279 | 0.320 |
| Cy3-G-3-siRNA chimeras | 78.2 | 0.00 | 0.811 |
| G-3-Cy5-siRNA chimeras | 0.114 | 75.1 | 1.67 |
| Cy3-G-3-Cy5-siRNA chimeras | 75.85 | 76.4 | 68.8 |
| Cy3-0-RNA pool | 7.63 | 0.082 | 0.121 |
| Cy5-siRNA | 0.246 | 3.32 | 1.27 |

FIG. 5D

| CEM-NKr-CCR5 cells | Cy3 positive (His %) | Cy5 positive (His %) | Both positive |
|---|---|---|---|
| Control | 0.076 | 0.125 | 0.076 |
| Cy3-G-3-siRNA chimeras | 86.0 | 0.013 | 0.206 |
| G-3-Cy5-siRNA chimeras | 0.132 | 72.0 | 0.339 |
| Cy3-G-3-Cy5-siRNA chimeras | 79.7 | 81.1 | 70.7 |
| Cy3-0-RNA pool | 0.808 | 0.091 | 0.111 |
| Cy5-siRNA | 0.583 | 0.872 | 0.472 |

FIG. 5E: CEM-NKr cells

| CEM negative cells | Cy3 positive (His %) | Cy5 positive (His %) | Both positive |
|---|---|---|---|
| Control | 0 | 0.052 | 0 |
| Cy3-G-3-siRNA chimeras | 9.98 | 0.011 | 0.066 |
| G-3-Cy5-siRNA chimeras | 0.012 | 5.81 | 0.147 |
| Cy3-G-3-Cy5-siRNA chimeras | 5.4 | 5.56 | 3.48 |
| Cy3-0-RNA pool | 1.14 | 0.009 | 0.052 |
| Cy5-siRNA | 0 | 0.450 | 0 |

Figure 5F:
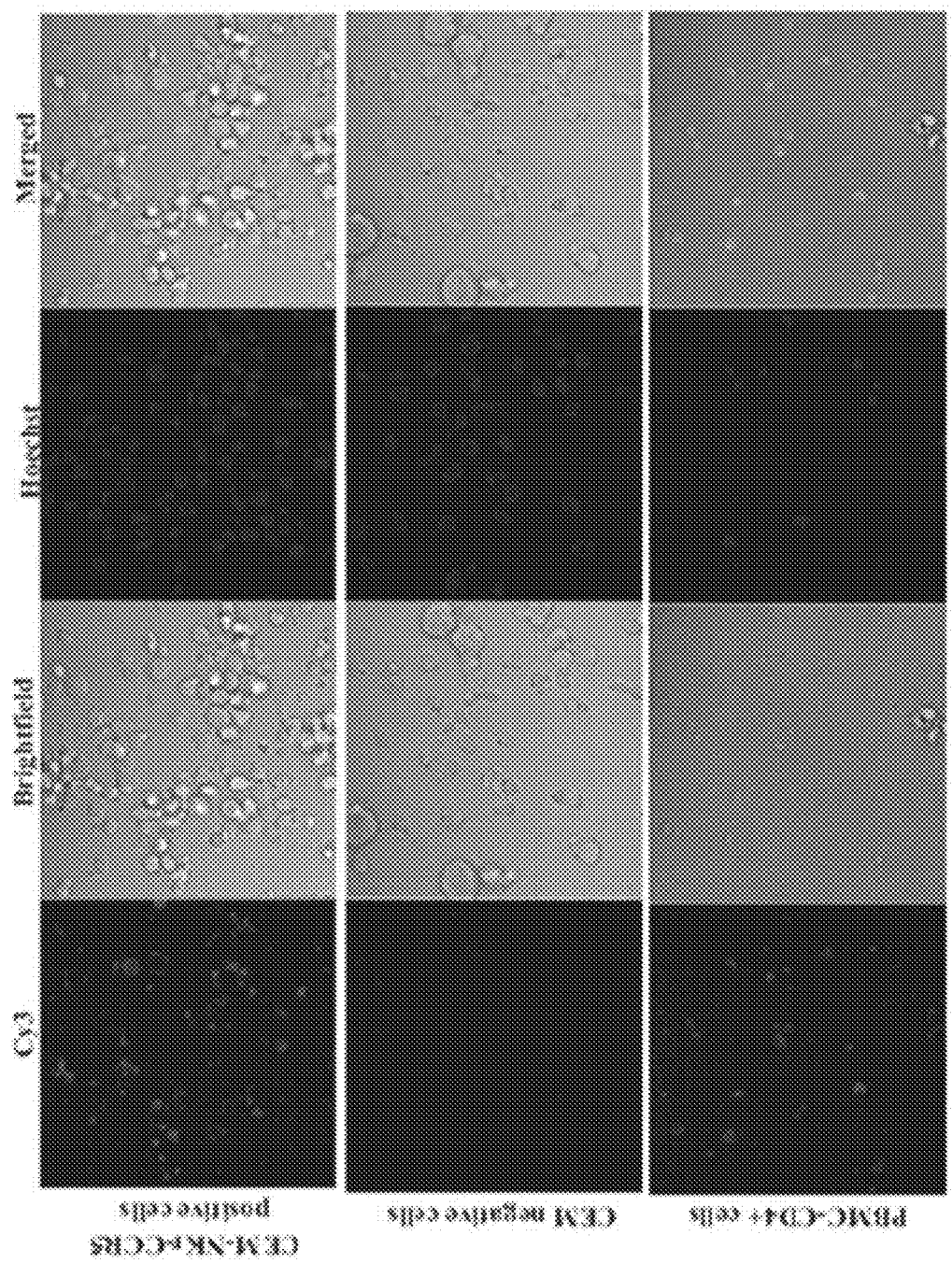

FIG. 5F summarizes the results of an internalization analysis. CEM-NKr-CCR5 positive cells, CEM negative cells, or PBMC-CD4+ cells were grown in 35 mm plates treated with polylysine and incubated with a 67 nM concentration of Cy3-labeled G-3-siRNA chimeras in complete culture media for real-time live-cell confocal microscopy analysis. The images were collected using 40×magnification.

Figure 5G:
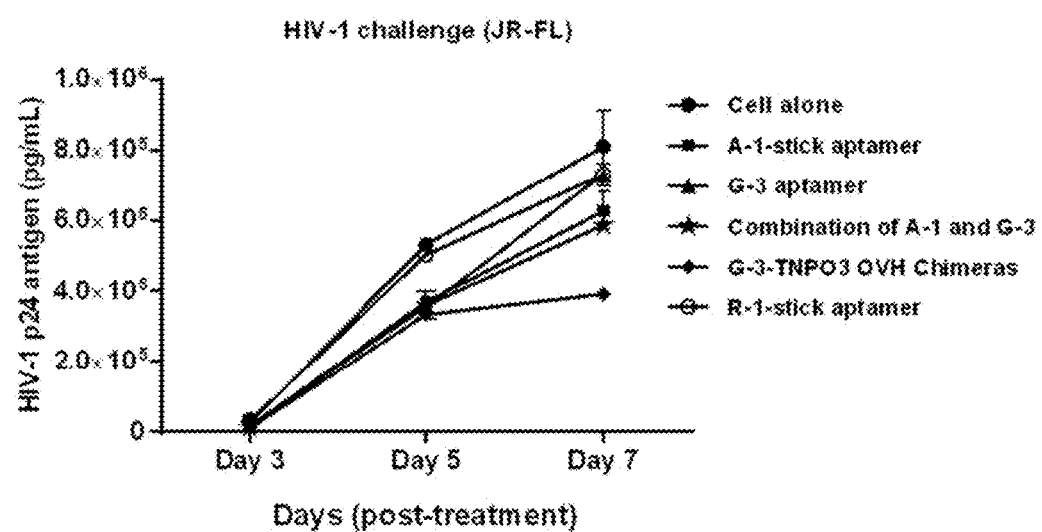

FIG. 5G Dual inhibition on HIV-1 infection mediated by aptamer-based siRNA delivery system. C) HIV-1 challenge assay. Human PBMC-CD4+ cells were infected with JR-FL and then incubated with experimental RNAs. A gp120 aptamer (A-1-stick) and an unrelated aptamer (R-1-stick) were used as positive and negative controls, respectively. Data represent the average of triplicate measurements of p24.

FIG. 6A-6E collectively illustrates CCR5 aptamer delivery of siRNAs with specific knockdown of TNPO3 expression via RNAi pathway. Relative TNPO3 mRNA expression was detected by real-time PCR.

Figure 6A:
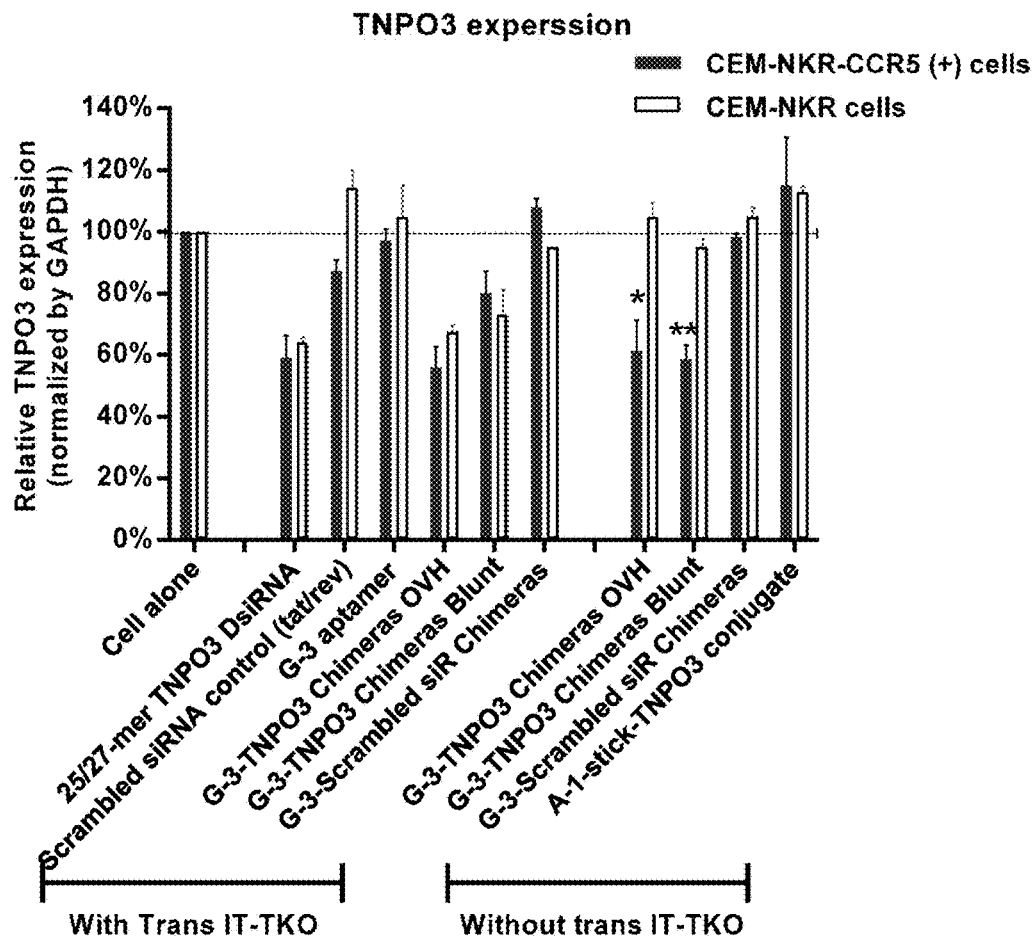

FIG. 6A illustrates detection of relative TNPO3 mRNA expression by real-time PCR in CEM-NKr-CCR5 and CEM-Nkr negative cells.

Figure 6B:
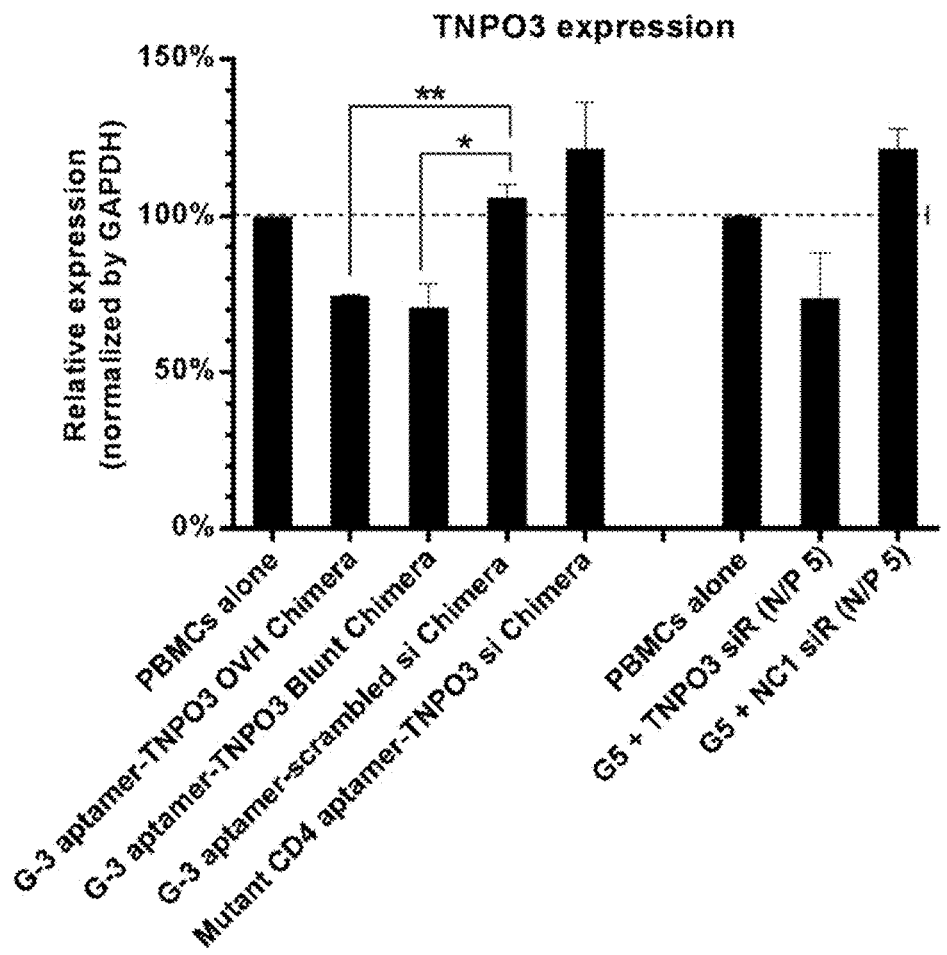

FIG. 6B illustrates detection of relative TNPO3 mRNA expression by real-time PCR in human PBMC-CD4+ cells. Cells were incubated with G-3 aptamer and chimeras in the presence or the absence of transfection agents. As positive control, transfection agents (Trans IT-TKO or G5 dendrimer) were used to transfect TNPO3 siRNA to CEM cells or PBMCs, respectively. As negative control, unrelated aptamer-siRNA chimera (anti-gp120 A-1 aptamer or mutant CD4 aptamer) and G-3 aptamer-scrambled siRNA chimera were used. Experiments were performed in triplicate. Asterisk indicates a significant difference compared with control (P<0.01, student's t-test).

Figure 6C:
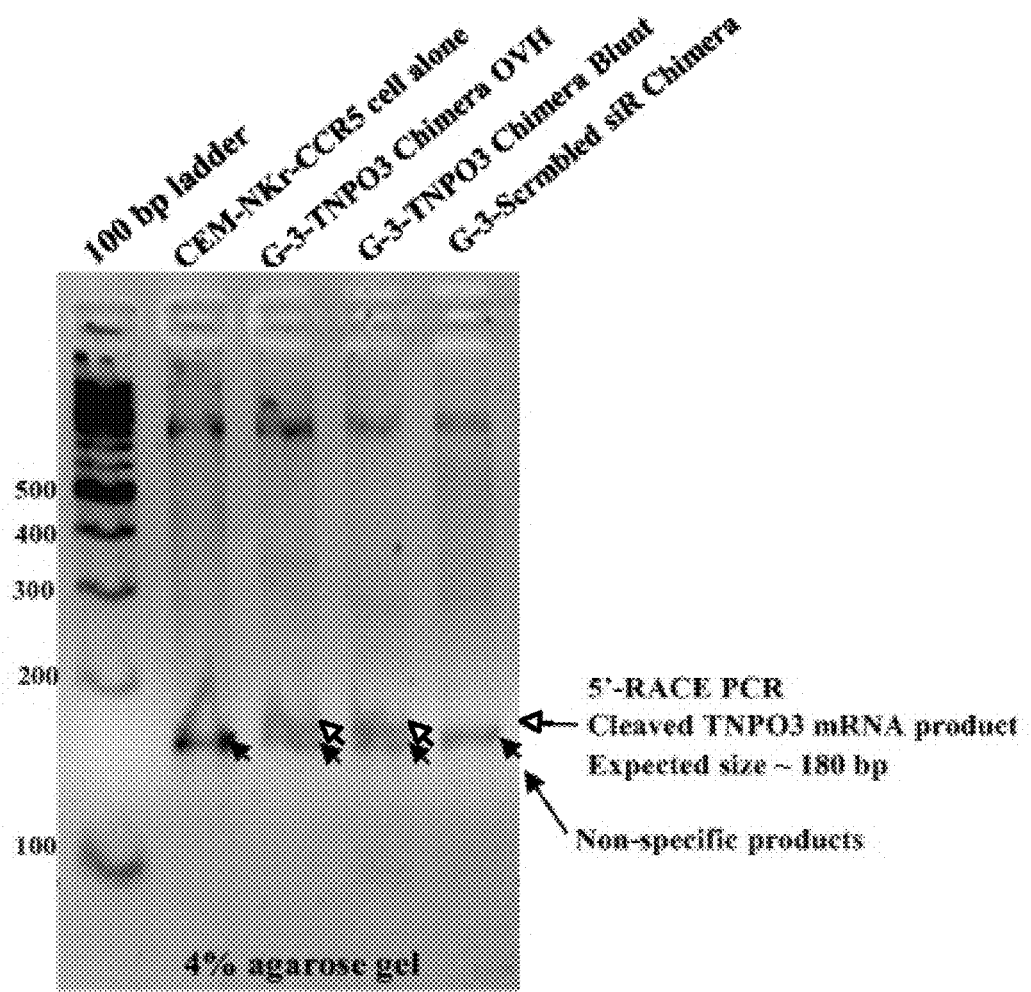

FIG. 6C presents a 5'-RACE PCR analysis of TNPO3 DsiRNA delivered by CCR5 aptamer—siRNA chimeras. Nested PCR products were resolved in an agarose gel; specific siRNA-mediated RACE PCR cleavage mRNA products are marked by an open (black outline with white interior) arrow.

Figure 6D:
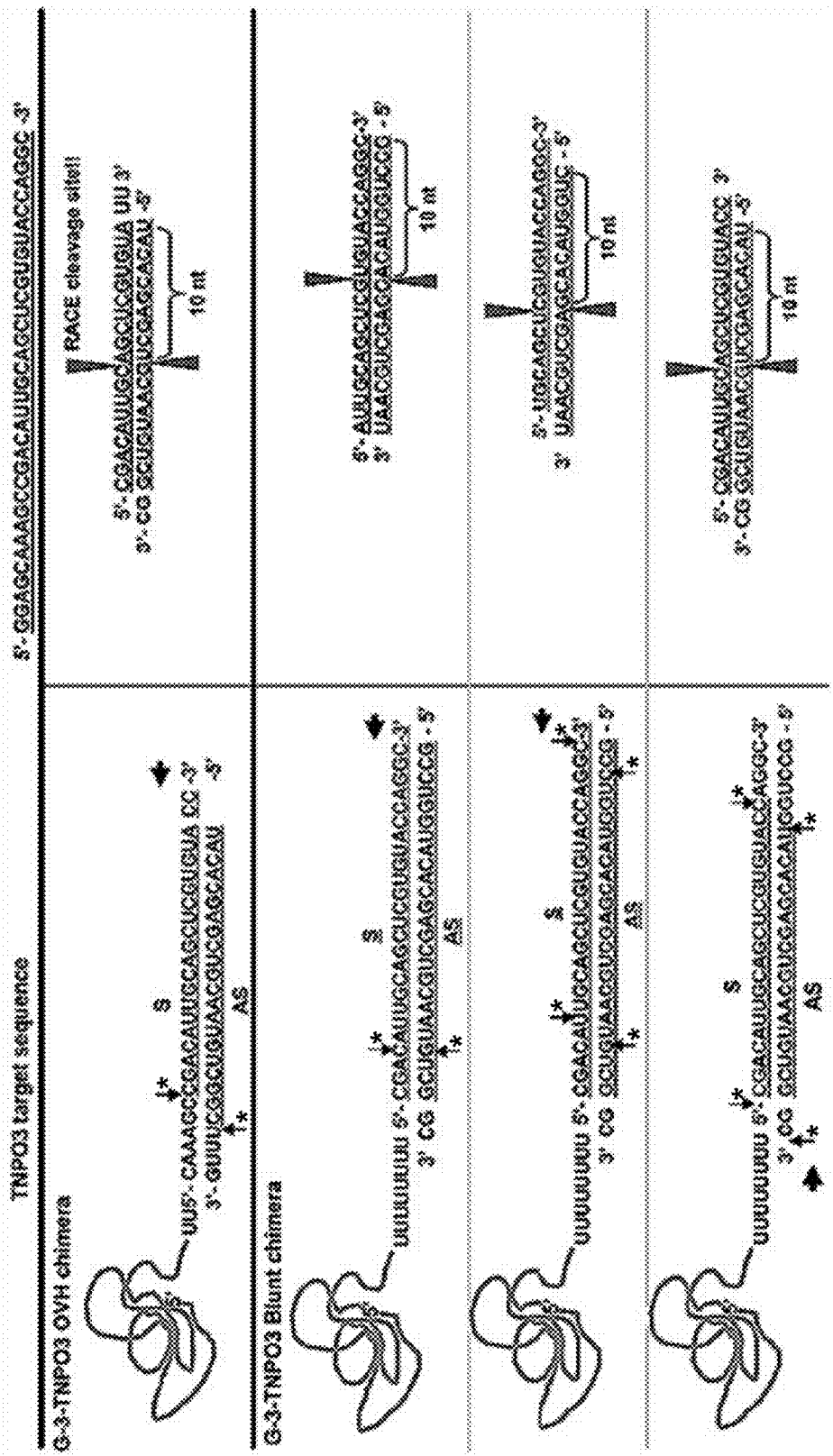

FIG. 6D presents DNA sequence analyses of cloned 5'-RACE PCR products, and a schematic of Dicer processing of aptamer-siRNA chimeras (OVH and Blunt designs), resulting in siRNA products. The positions of the siRNA directed cleavage sites in the TNPO3 target RNA are indicated with a pair of grey triangles. According to mRNA cleavage, these predicted siRNA species also are shown with arrows indicated with a star ("*"). The proposed directions of Dicer entry are indicated by a bold black arrow. Sequence legend: FIG. 6D: TNPO3 target sequence (SEQ ID NO:69); left column (top to bottom: SEQ ID NOS:70-77; right column (top to bottom): SEQ ID NOS:78-85.

Figure 6E:
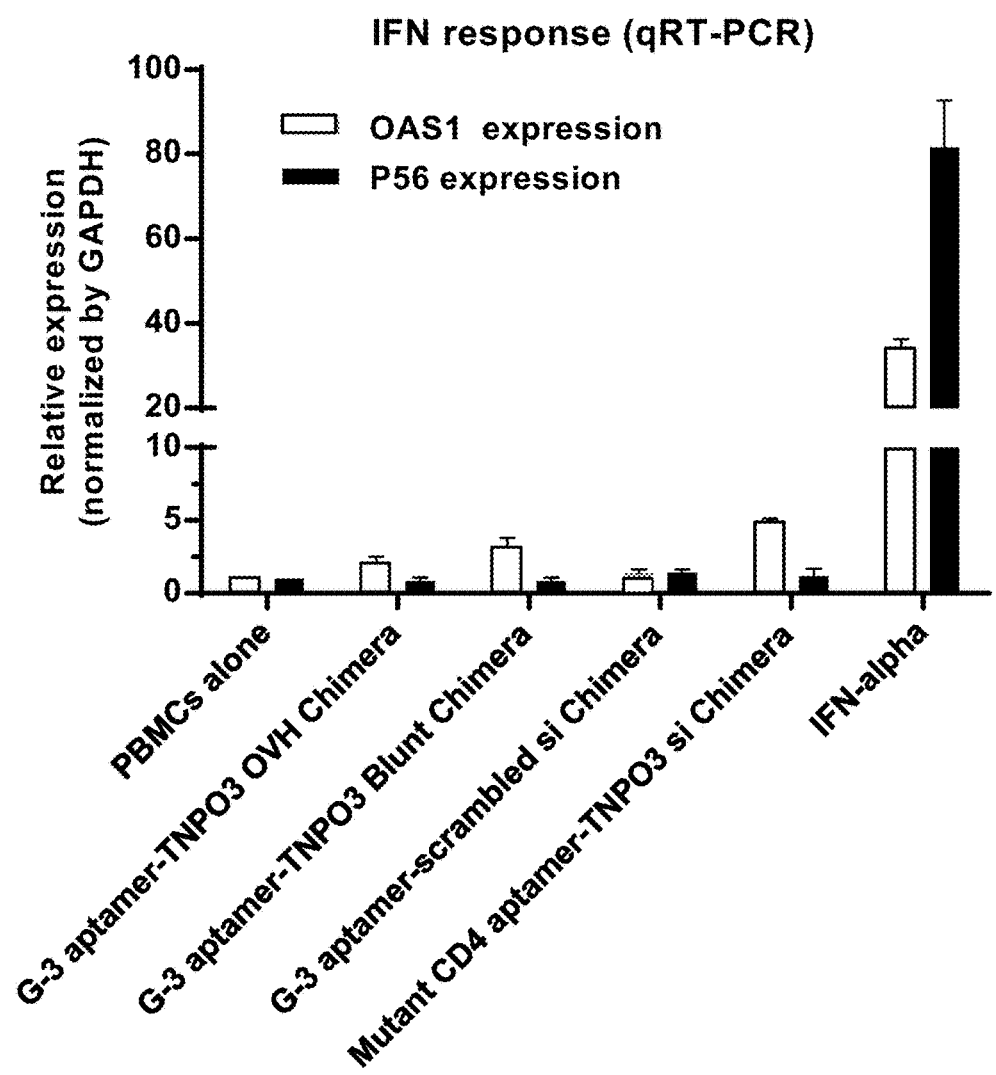

FIG. 6E presents IFN gene activation assays in human PBMCs. The interferon response genes encoding P56 (CDKL2) and OAS1, were measured by quantitative RT-PCR. No induction of type I interferon gene expression was observed in cells treated with the aptamers or chimeras whereas IFN-alpha itself as positive control induced potent response gene expression. Gene expression for the interferon induced genes was normalized to GAPDH mRNA levels. These data represent the average of three replicate measurements.

Figure 7A:
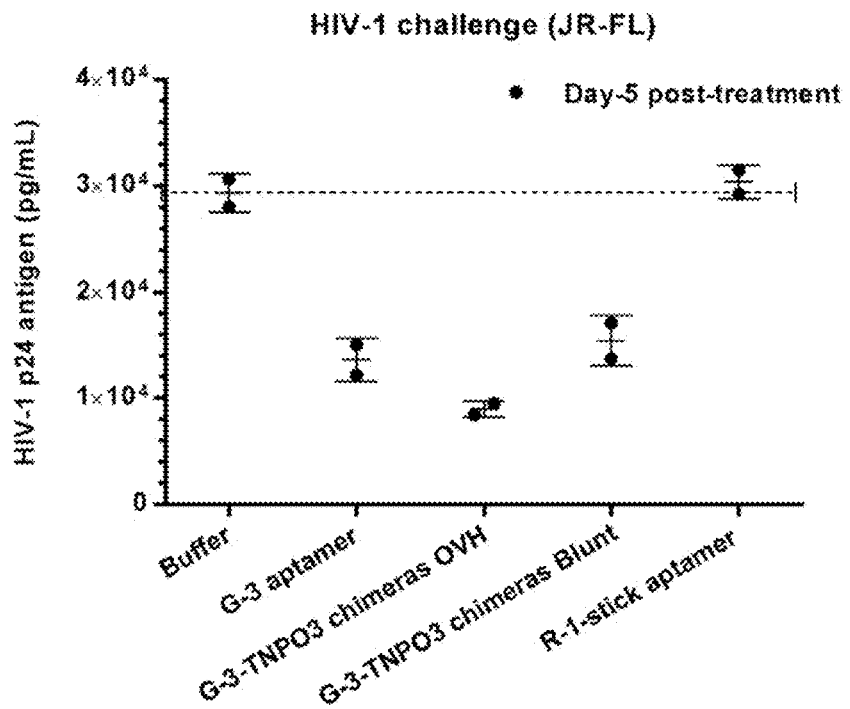
Figure 7B:
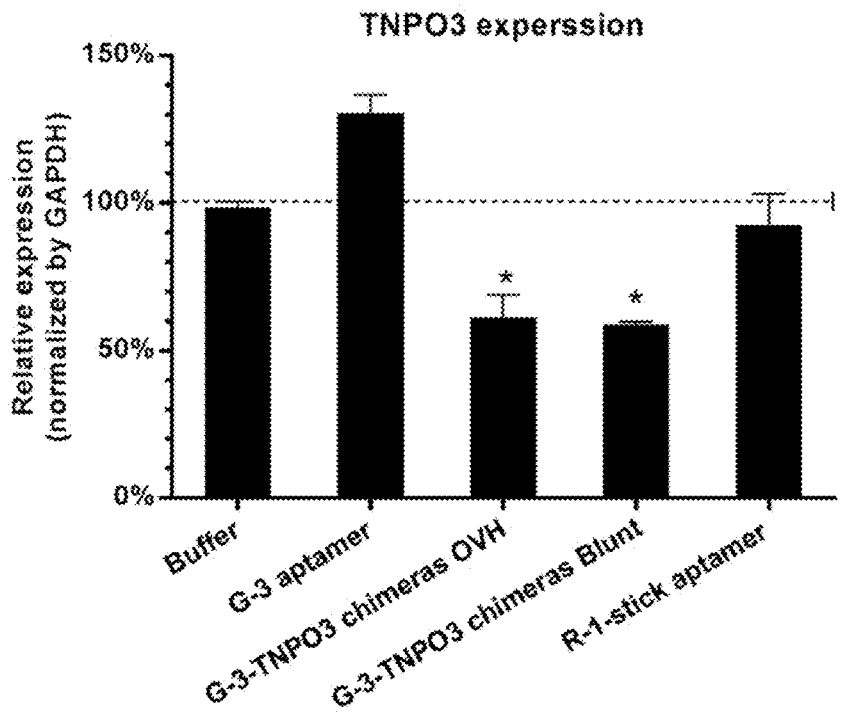

FIG. 7A-7B collectively illustrates the dual inhibition of HIV-1 infection mediated by aptamer-based siRNA delivery system. FIG. 7A illustrates an HIV-1 challenge assay. G-3 aptamers or aptamer-siRNA chimeras were incubated with primary PBMCs. After 4-6 hours incubation, the R5 strain virus (JR-FL) was added into each well. The culture supernatants were collected at five days after treatment for HIV-1 p24 antigen ELISA assay. As negative control, irrelative aptamer (R-1 aptamer against BAFF-R protein) was used. Data represent the average of triplicate measurements of p24.

FIG. 7B demonstrates that the siRNA delivered by aptamers knocked down TNPO3 gene expression in human PBMCs. Relative TNPO3 mRNA expression was detected by real-time PCR, with GAPDH as internal control. Data represent the average of three triplicates.

Figure 8:
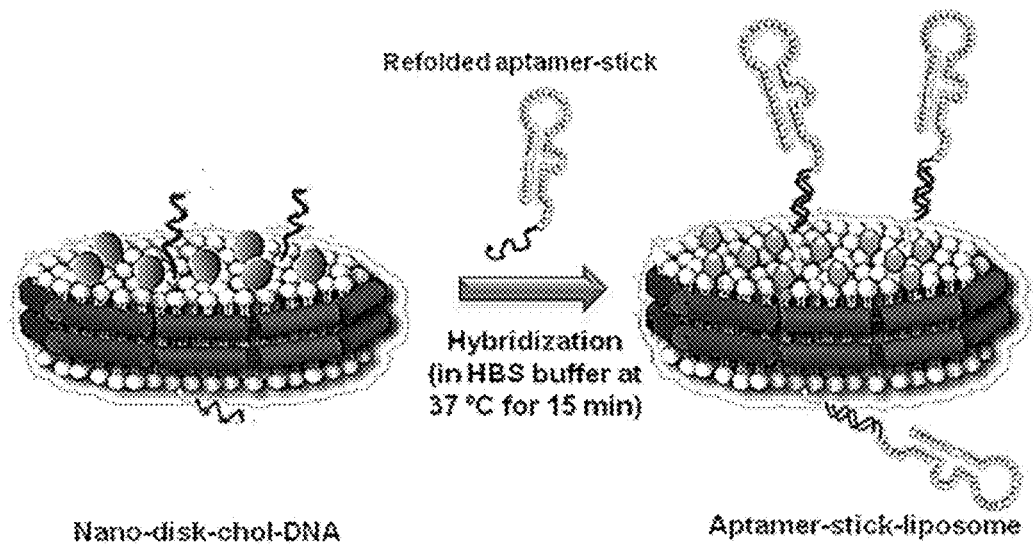

FIG. 8 illustrates the conversion of "Nano-disk-chol-DNA" (containing liposome, Lipid-AF488, and 5-10 DNA stick oligos per nanoparticle) to an "Aptamer-stick-liposome" (comprising a 2'-F modified RNA sequence plus a "GC" rich RNA stick sequence).

Figure 9:
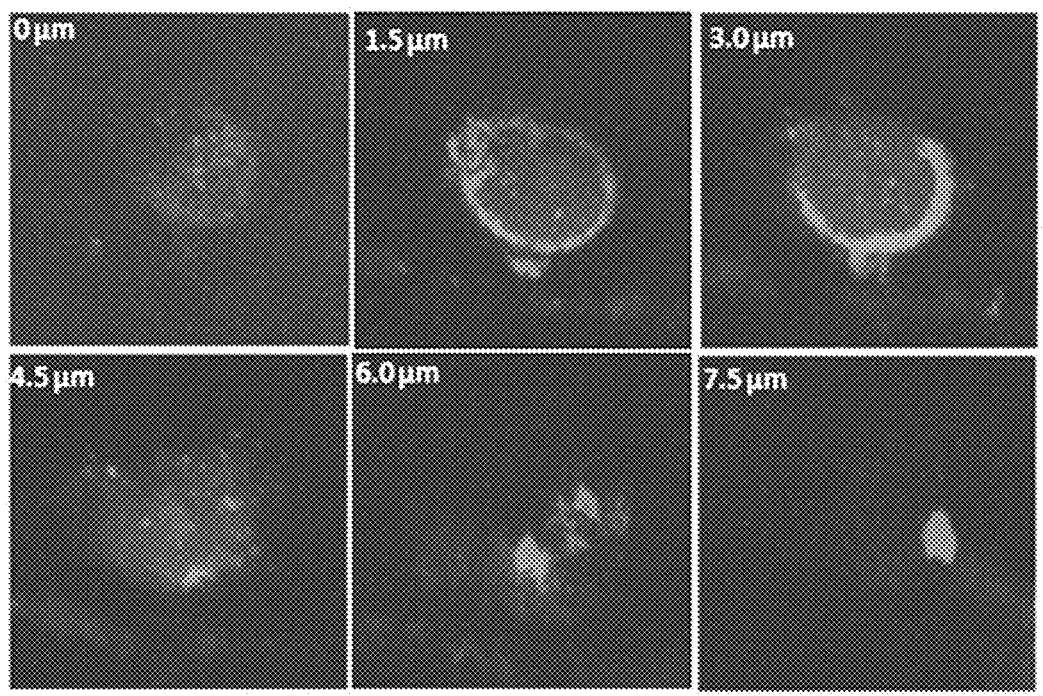

FIG. 9 Cell surface binding of Cy3-labeled RNAs was assessed by flow cytometry. Internalization analysis and localization analysis. PBMC-CD4+ cells were grown in 35 mm plates treated with polylysine and incubated with a 67 nM concentration of Cy3-labeled G-3 aptamer in complete culture media for real-time live-cell confocal microscopy analysis. The images were collected using 40×magnification. Z-stack images (from bottom to top of the cells) were shown here.

Figure 10:
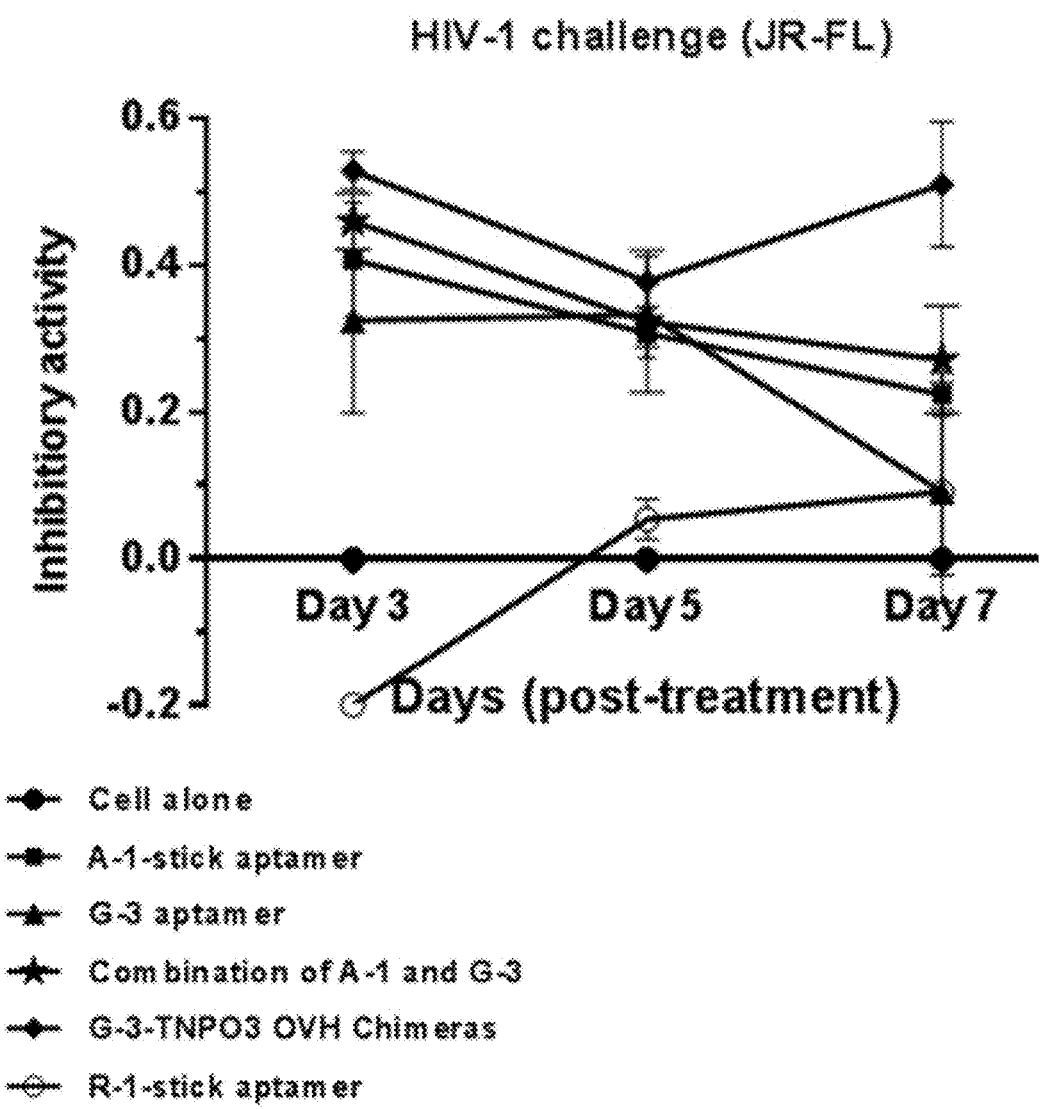

FIG. 10 HIV-1 challenge assay. Primary PBMCs were infected with HIV-1 JR-FL virus (MOI 0.01). After 5 days post-infection, aptamers or aptamer-siRNA chimeras were incubated with HIV-1 infected cells. The culture supernatants were collected at different days after treatment for HIV-1 p24 antigen ELISA assay. The inhibitory activity was calculated by the formula [(p24 value of the cell alone−p24 value of the sample)/p24 value of the cell alone)]. 1 of the inhibitory activity means completed inhibition. A gp120 aptamer (A-1-stick) and an unrelated aptamer (R-1-stick) were used as positive and negative controls, respectively. Data represent the average of triplicate measurements.

DETAILED DESCRIPTION OF THE INVENTION

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid, linker as provided herein or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice (e.g., conjugate chemistry).

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The term "promoter" or "regulatory element" refers to a region or sequence determinants located upstream or downstream from the start of transcription and which are involved in recognition and binding of RNA polymerase and other proteins to initiate transcription. Promoters need not be of viral origin, for example, mammalian cellular promoters, such as the polymerase II promoter U1 and polymerase III promoter tRNA$^{Ser}$ may be used in the present invention.

The term "aptamer" as provided herein refers to oligonucleotides (e.g. short oligonucleotides or deoxyribonucleotides), that bind (e.g. with high affinity and specificity) to proteins, peptides, and small molecules. Aptamers may have secondary or tertiary structure and, thus, may be able to fold into diverse and intricate molecular structures. Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino acid side chains to expand the aptamer's chemical diversity. As a result high affinity aptamers for almost any protein target are enriched and identified. Aptamers exhibit many desirable properties for targeted drug delivery, such as ease of selection and synthesis, high binding affinity and specificity, low immunogenicity, and versatile synthetic accessibility.

An "antisense nucleic acid" as referred to herein is a nucleic acid (e.g. DNA or RNA molecule) that is complementary to at least a portion of a specific target nucleic acid (e.g. an mRNA translatable into a protein) and is capable of reducing transcription of the target nucleic acid (e.g. mRNA from DNA) or reducing the translation of the target nucleic acid (e.g. mRNA) or altering transcript splicing (e.g. single stranded morpholino oligo). See, e.g., Weintraub, *Scientific American,* 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbone modified nucleotides.

In the cell, the antisense nucleic acids hybridize to the corresponding mRNA, forming a double-stranded molecule. The antisense nucleic acids interfere with the translation of the mRNA, since the cell will not translate an mRNA that is double-stranded. The use of antisense methods to inhibit the in vitro translation of genes is well known in the art (Marcus-Sakura, *Anal. Biochem.,* 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

A "siRNA," "small interfering RNA," "small RNA," or "RNAi" as provided herein refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a siRNA or RNAi is a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The term "antiviral RNA" as provided herein refers to an RNA that is capable of inhibiting the activity (e.g., transcription, translation, replication, infectivity) of a virus (e.g., HIV). In embodiments, the antiviral RNA binds to a target viral nucleic and reduces transcription of the target viral nucleic acid or reduces the translation of the target viral nucleic acid (e.g. mRNA) or alters transcript splicing. In embodiments, the antiviral RNA is a nucleic acid that is capable of binding (e.g. hybridizing) to a target viral nucleic acid (e.g. an Rev RNA) and reducing translation of the target viral nucleic acid. The target viral nucleic acid is or includes one or more target nucleic acid sequences to which the antiviral RNA binds (e.g. hybridizes). In embodiments, the antiviral RNA is or includes a sequence that is capable of hybridizing to at least a portion of a target viral nucleic acid at a target viral nucleic acid sequence. Non-limiting examples of an antiviral RNA include siRNAs, ribozymes, RNA decoys, snoRNAs and shRNAs.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between an aptamer as provided herein or an siRNA and a suitable linker can be direct, e.g., by covalent bond, or indirect, e.g., by non-covalent bond. Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. Thus, the aptamer or siRNA can be attached to a linker through its backbone. Optionally, the aptamer or siRNA includes one or more reactive moieties, e.g., an amino acid reactive moiety, that facilitates the interaction of the aptamer or siRNA with the linker. In embodiments, the aptamer and siRNA form a conjugate in the absence of a linker, wherein the conjugate may be direct, e.g., by covalent bond, or indirect, e.g., by non-covalent bond.

Useful reactive moieties or functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

The reactive functional groups can be chosen such that they do not participate in, or interfere with, the chemical stability of the nucleic acids (siRNA), aptamers or suitable linkers described herein. By way of example, the aptamer can include a vinyl sulfone or other reactive moiety. Optionally, the nucleic acids (siRNA), aptamers or suitable linkers can include a reactive moiety having the formula S—S-R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as described below, the preferred algorithms can account for gaps and the like. Preferably, identity exists over a region that is at least about 25 amino acids or nucleotides in length, or more preferably over a region that is 50-100 amino acids or nucleotides in length.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

For specific proteins described herein (e.g., CCR5), the named protein includes any of the protein's naturally occurring forms, variants or homologs that maintain the proteins activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "CCR5" as provided herein includes any of the C-C chemokine receptor type 5 (CCR5) protein naturally occurring forms, homologs or variants that maintain the activity of CCR5 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CCR5 protein is the protein as identified by the UniProt sequence reference P51681. In embodiments, the CCR5 protein is the protein as identified by the NCBI sequence reference GI:4502639, homolog or functional fragment thereof. In embodiments, the CCR5 protein is encoded by a nucleic acid sequence corresponding to Gene ID: GI:154091329.

"TNPO3" or "TNPO3 gene" as referred to herein includes any of the recombinant or naturally-occurring forms of the gene encoding the transportin-3 protein or variants or homologs thereof that maintain TNPO3 protein activity (e.g. within at least 50%, 80%, 90%, 95%, 96%, 97%, 98%, 99% or 100% activity compared to TNPO3). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TNPO3 polypeptide. In embodiments, the TNPO3 gene is substantially identical to the nucleic acid identified by the NCBI reference number GI: 300934784 or a variant or homolog having substantial identity thereto.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

"Contacting" is used in accordance with its plain ordinary meaning and refers to the process of allowing at least two distinct species (e.g. aptamers, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a RNA aptamer as described herein and a cell (e.g., HIV-infected cell).

As used herein, the term "infectious disease" refers to a disease or condition related to the presence of an organism (the agent or infectious agent) within or contacting the subject or patient. Examples include a bacterium, fungus, virus, or other microorganism. A "bacterial infectious disease" is an infectious disease wherein the organism is a bacterium. A "viral infectious disease" is an infectious disease wherein the organism is a virus (e.g., HIV).

The term "associated" or "associated with" as used herein to describe a disease (e.g. an infectious disease) means that the disease (e.g. HIV infection) is caused by, or a symptom of the disease is caused by, or a symptom of the disease is caused by a virus (e.g., HIV).

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The terms "prevent," "preventing" or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease (e.g. infectious disease), or to a patient reporting one or more of the physiological symptoms of a disease, even though a diagnosis of this disease may not have been made.

Where combination treatments are contemplated, it is not intended that the agents (i.e. aptamers) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein (e.g. Tat, Rev) relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

As defined herein, the term "inhibition", "inhibit", "inhibiting" and the like in reference to an siRNA or protein-inhibitor interaction means negatively affecting (e.g., decreasing) the activity or function of the protein (e.g. decreasing gene transcription or translation) relative to the activity or function of the protein in the absence of the inhibitor. In embodiments, inhibition refers to reduction of a disease or symptoms of disease (e.g., HIV infection). In embodiments, inhibition refers to a reduction in the activity of a signal transduction pathway or signaling pathway (e.g. reduction of viral replication). Thus, inhibition includes, at least in part, partially or totally blocking stimulation, decreasing, preventing, or delaying activation, or inactivating, desensitizing, or down-regulating transcription, translation, signal transduction or enzymatic activity or the amount of a protein (e.g. a viral protein or a cellular protein). In embodiments, inhibition refers to inhibition of CCR5.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a siRNA, (e.g., shRNA, miRNA, snoRNA, RNA decoy, ribozyme), compound or small molecule that inhibits viral infection (e.g., replication) e.g., by binding, partially or totally blocking stimulation, decrease, prevent, or delay activation, or inactivate, desensitize, or down-regulate signal transduction, gene expression or enzymatic activity necessary for protein activity. Inhibition as provided herein may also include decreasing or blocking a protein activity (e.g., activation of viral transcription) by expressing a mutant form of said protein thereby decreasing or blocking its activity.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

In accordance with certain aspects and embodiments of the present invention, there are provided 2'-fluoropyrimidine modified RNA aptamers which selectively bind to human CCR5. A 2'-fluoropyrimidine modified RNA aptamer as provided herein is an RNA aptamer including a fluoro substituent attached to a pyrimidine base (e.g., uracil or cytosine). In embodiments, the fluoro substituent is attached at the 2' position of the ribose of a pyrimidine base.

Nucleic acid aptamers are single-stranded DNA or RNA molecules, which can be selected from a combinatorial DNA or RNA library through SELEX technology. Similar to the antibody—antigen interaction, the unique three-dimensional recognition between aptamers and their target is exquisitely specific, and has low nanomolar dissociation constant. By functionalizing the cell-specific, internalizing aptamers with a drug or delivery vehicle, the specific recognition and internalization of the therapeutic agents by the target cell population or tissue can be improved. 2'-fluoro-modified RNA aptamers described herein specifically bind and are internalized to the target proteins expressing cells (HIV-1 gp120 protein, B-cell-activating factor receptor (BAFF-R) protein, human CCR5 protein). These aptamers can be covalently or physically conjugated to siRNA for targeted RNAi therapy.

In accordance with certain aspects and embodiments of the present invention, a GC-rich "sticky sequence" has been designed as a connector to noncovalently connect anti-HIV gp120 RNA aptamers with various siRNAs for targeted HIV-1 therapy.

Lipid-based nanodisc systems that have a membrane scaffold protein have many advantages. They possess a relatively large surface area, thereby providing a platform for conjugating multiple ligands (aptamers) and various drugs (siRNAs, chemotherapeutic agents, or peptides). Because of their specific structures, lipid-based nanodiscs can both encapsulate hydrophilic therapeutic agents inside their aqueous core and load hydrophobic drugs within their lipid bilayer membrane. In order to selectively deliver drugs to the sites of action, lipid-based nanodiscs may optionally be decorated with various targeting ligands.

Therefore, in accordance with certain aspects and embodiments of the present invention, one can take advantage of the above-described "sticky bridge" and cell-type specific aptamers to develop a cell-type specific aptamer-stick-nanodisc delivery system for targeted drug delivery. In this design, the RNA aptamer and a lipid molecule which was attached to complementary 17-base GC-rich bridge sequences were chemically synthesized, thereby allowing the aptamer and lipid tail to be annealed through Watson-Crick based pairing by simple mixing (see FIG. 8). The lipid tail and a model fluorescent molecule are incorporated into a nanodisc. The bridge facilitates the non-covalent binding of the nanodisc system with the cell-type specific RNA aptamers. The resulting BAFF-R RNA aptamer-stick-nanodisc system specifically increases the cellular internalization of the fluorescent molecule in the BAFF-R expressing B-cell line (Jeko-1 cells).

In accordance with certain aspects and embodiments of the present invention, the above-described aptamer selectively binds and internalizes into human CCR5-expressing cells.

Exemplary aptamers have at least 80% sequence identity with G-3:

```
                                        (SEQ ID NO: 1)
5'-GGG AGG ACG AUG CGG GCC UUC GUU UGU UUC GUC
CAC AGA CGA CUC GCC CGA-3'.
```

In accordance with certain aspects and embodiments of the present invention, the above-described aptamer has at least 85% sequence identity with G-3; in accordance with certain aspects and embodiments of the present invention, the above-described aptamer has at least 90% sequence identity with G-3; in accordance with certain aspects and embodiments of the present invention, the above-described aptamer has at least 95% sequence identity with G-3; in accordance with certain aspects and embodiments of the present invention, the above-described aptamer has at least 98% sequence identity with G-3; in accordance with certain aspects and embodiments of the present invention, the above-described aptamer has substantially the same sequence as G-3 (SEQ ID NO: 1). In embodiments, the RNA aptamer has the sequence of SEQ ID NO:1.

In accordance with certain aspects and embodiments of the present invention, there are provided chimeric constructs comprising:

an aptamer as described herein, and antiviral siRNA, optionally linked by a suitable linker.

In accordance with certain aspects and embodiments of the present invention, there are provided dual inhibitory drugs for the selective delivery of antiviral siRNA to HIV-infected cells, said drug comprising an aptamer as described herein and an antiviral siRNA, optionally linked by a suitable linker.

The dual drug inhibitor provided herein (including embodiments thereof) may include an aptamer as described herein and a compound moiety. Where the dual drug inhibitor includes a compound moiety, the compound moiety may be covalently (e.g. directly or through a covalently bonded intermediary) attached to the aptamer (see, e.g., useful reactive moieties or functional groups used for conjugate chemistries set forth above). Thus, in embodiments, the dual drug inhibitor includes a compound moiety covalently attached to the aptamer. In embodiments, the compound moiety and the aptamer form a conjugate. In embodiments, the compound moiety is non-covalently (e.g. through ionic bond(s), van der Waal's bond(s)/interactions, hydrogen bond(s), polar bond(s), or combinations or mixtures thereof) attached to the aptamer.

In embodiments, the compound moiety is a therapeutic moiety or an imaging moiety covalently attached to the RNA sequence. The term "therapeutic moiety" as provided herein is used in accordance with its plain ordinary meaning and refers to a monovalent compound having a therapeutic benefit (prevention, eradication, amelioration of the underlying disorder being treated) when given to a subject in need thereof. Therapeutic moieties as provided herein may include, without limitation, peptides, proteins, nucleic acids, nucleic acid analogs, small molecules, antibodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, and glucocorticoid. In embodiments, the therapeutic moiety is an antiviral agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is a peptide moiety. In embodiments, the therapeutic moiety is a small molecule drug moiety.

In accordance with certain aspects and embodiments of the present invention, there are provided methods of neutralizing R5 virus infection in primary PBMCs, said method comprising contacting said PBMCs with an aptamer as described herein.

In accordance with certain aspects and embodiments of the present invention, there are provided methods of neutralizing R5 virus infection in primary PBMCs, said method comprising contacting said PBMCs with a dual inhibitory drug as described herein.

In accordance with certain aspects and embodiments of the present invention, there are provided methods of inhibiting the ability of CCR5 to facilitate entry of HIV into target cells, said method comprising contacting said target cell with an aptamer as described herein.

In accordance with certain aspects and embodiments of the present invention, there are provided methods of inhibiting the ability of CCR5 to facilitate entry of HIV into target cells, said method comprising contacting said target cell with a dual inhibitory drug as described herein.

In accordance with certain aspects and embodiments of the present invention, there are provided methods of treating a subject infected with HIV, said method comprising administering to said subject an effective amount of a dual inhibitory drug as described herein.

The term "subject" includes living organisms which are infected with HIV or are susceptible to infection with HIV. The term "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as chickens, ducks, peking ducks, geese, and transgenic species thereof. The term "subject," includes to a subject, e.g., a human, specifically chosen to receive an aptamer according to the present invention, or a composition containing same. Accordingly, in some embodiments, subjects include subjects who are at risk of becoming infected with HIV, or have been diagnosed as being infected with HIV. Subjects at risk of becoming infected with HIV include those with an underlying disease, such as a metabolic disorder, an inflammatory disease, infection, hereditary fever or neoplasm which may pre-dispose one to such infection. In some embodiments, a preferred subject is a human.

The terms "treatment" or "treating" of a subject includes the application or administration of an aptamer according to the present invention, or a composition containing same to a subject (or application or administration of an aptamer according to the present invention, or a composition containing same to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; stabilization, diminishing of symptoms or making the injury, pathology or condition more tolerable to the subject; slowing in the rate of degeneration or decline; making the final point of degeneration less debilitating; or improving a subject's physical or mental well-being. In an embodiment, the term "treating" can include increasing a subject's life expectancy.

The term "therapeutically effective amount" refers to the amount of a compound which is effective to treat a subject, e.g., treat a subject infected with HIV or a subject having an underlying disease, such as, but not limited to, a metabolic disorder, an inflammatory disorder, a malignant neoplasm, or chronic microbial infection. The therapeutically effective amount may vary based on the particular disorder(s) the subject is suffering from, the age, weight, and lifestyle of a particular subject. In addition, the therapeutically effective amount may depend on the severity of the disease state, organ function, kidney function, or underlying disease (e.g., the subject may be suffering from an inflammatory disease, a malignant neoplasm, a chronic infection, or the like).

The dosage administered in the methods of the present disclosure may be selected such that desired pharmacokinetic parameters and/or biologically favorable parameters are obtained after administration of the compound of the disclosure to the subject.

The term "pharmaceutical formulation" includes pharmaceutical compositions as described below. In a further embodiment, the pharmaceutical formulations are designed to have favorable biological properties which enhance the ability of the compounds of the disclosure to prevent infection with HIV.

The disclosure also pertains, at least in part, to a pharmaceutical composition comprising a therapeutically effective amount of an aptamer according to the present invention, or a composition containing same and a second agent.

In a further embodiment, the therapeutically effective amount is effective to prevent infection with HIV.

In a further embodiment, the disclosure pertains to a packaged pharmaceutical composition. The packaged pharmaceutical composition includes a therapeutically effective amount of an aptamer according to the present invention, or a composition containing same, packaged in combination with a label or insert advising that the composition be administered in combination with a second agent. In a further embodiment, the therapeutically effective amount is effective to prevent infection with HIV.

In yet another further embodiment, the disclosure pertains to a packaged pharmaceutical composition, which includes a therapeutically effective amount of a second agent packaged in combination with a label or insert advising that the composition be administered in combination with an aptamer according to the present invention, or a composition containing same.

The term "label or insert" includes, but is not limited to all written, electronic, or spoken communication with the subject, or with any person substantially responsible for the care of the subject, regarding the administration of the compositions of the present disclosure. An insert may further include information regarding coadministration of the compositions of the present disclosure with other compounds or compositions, e.g., second agents. Additionally, an insert may include instructions regarding administration of the compositions of the present disclosure with (or without) food.

In yet another embodiment, the disclosure pertains to a packaged pharmaceutical composition, which includes a container holding a pharmaceutical composition comprising a therapeutically effective amount of an aptamer according to the present invention, or a composition containing same in combination with a label or insert advising that the composition be administered with (or without) food.

An aptamer according to the present invention, or a composition containing same may be supplied in a solution with an appropriate solvent or in a solvent-free form (e.g., lyophilized). In another aspect of the disclosure, the agents and buffers necessary for carrying out the methods of the disclosure may be packaged as a kit. The kit may be commercially used according to the methods described herein and may include instructions for use in a method of the disclosure. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components may optionally further comprise buffers.

Aptamers according to the present invention, or a composition containing same may also be administered in a variety of ways, e.g., parenterally, intraperitoneally, intraspinally, intracerebrally, and the like. Dispersions can be prepared in glycerol, liquid polyethylene glycols, and mixtures thereof and in oils. Under ordinary conditions of storage and use, these preparations may contain a preservative to prevent the growth of microorganisms.

To administer aptamers according to the present invention, or a composition containing same by other than parenteral administration, it may be necessary to coat the active agent with, or co-administer the active agent with, a material to prevent its inactivation. For example, an aptamer according to the present invention, or a composition containing same may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7, 27 (1984)). It should be noted that the term "pharmaceutical composition" includes the "pharmaceutical formulations" described above.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the compound of the disclosure) plus any additional desired ingredient from a previously sterile-filtered solution thereof.

Aptamers according to the present invention, or compositions containing same can be orally administered, for example, with an inert diluent or an assimilable edible carrier. Aptamers according to the present invention, or compositions containing same and other ingredients may also be enclosed in a hard or soft shell gelatin capsule, compressed into tablets, or incorporated directly into the subject's diet. For oral therapeutic administration, an aptamer according to the present invention, or a composition containing same may be incorporated with excipients and used in the form of ingestible tablets, buccal tablets, troches, capsules, elixirs, suspensions, syrups, wafers, and the like. The percentage of the aptamer according to the present invention, or a composition containing same in the compositions and preparations may, of course, be varied. The amount of aptamer according to the present invention, or a composition containing same in such therapeutically useful compositions is such that a suitable dosage will be obtained.

The present disclosure therefore includes pharmaceutical formulations comprising aptamers according to the present invention, or a composition containing same, in pharmaceutically acceptable vehicles for aerosol, oral and parenteral administration. Also, the present disclosure includes such compounds, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present disclosure, an aptamer according to the present invention, or a composition containing same may be administered orally or through inhalation as a solid, or may be administered intramuscularly or intravenously as a solution, suspension or emulsion. Alternatively, the agents or salts may also be administered by inhalation, intravenously or intramuscularly as a liposomal suspension.

Pharmaceutical compositions or formulations are also provided which are suitable for administration as an aerosol, by inhalation. These formulations comprise a solution or suspension of an aptamer according to the present invention, or a composition containing same, or a plurality of solid particles of the agent or salt. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of an aptamer according to the present invention, or a composition containing same, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble form of an aptamer according to the present invention, or a composition containing same, in a carrier which comprises water. A surfactant may be present which lowers the surface tension of the formulation sufficiently to result in the formation of droplets within the desired size range when subjected to nebulization.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, shellac, and the like.

Other compositions useful for attaining systemic delivery of an aptamer according to the present invention, or a composition containing same include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Aptamers according to the present invention, or compositions containing same can also be administered topically to a subject, e.g., by the direct laying on or spreading of a composition containing same on the epidermal or epithelial tissue of the subject, or transdermally via a "patch". Such compositions include, for example, lotions, creams, solutions, gels and solids. These topical compositions may comprise an effective amount, usually at least about 0.1 wt %, or even from about 1 wt % to about 5 wt %, of an aptamer according to the present invention, or a composition containing same. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents, and the like.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50; usually a larger therapeutic index is more efficacious. While compounds that exhibit toxic side effects may be used, care should be taken to design a delivery system that targets such agents to the site of affected tissue in order to minimize potential damage to unaffected cells and, thereby, reduce side effects.

It is understood that appropriate doses depend upon a number of factors within the ken of the ordinarily skilled physician, veterinarian, or researcher. The dose(s) of aptamer according to the present invention, or a composition containing same will vary, for example, depending upon the identity, size, and condition of the subject or sample being treated, further depending upon the route by which the composition is to be administered, if applicable, and the effect which the practitioner desires the aptamer according to the present invention, or a composition containing same to have upon the subject. Exemplary doses include milligram or microgram amounts of aptamer according to the present invention, or a composition containing same per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses depend upon the potency. Such appropriate doses may be determined using assays known in the art. When an aptamer according to the present invention, or a composition containing same is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, and any drug combination.

Parenteral compositions may be formulated in dosage unit form for ease of administration and uniformity of dosage. Dosage unit form as used herein refers to physically discrete units suited as unitary dosages for the subjects to be treated; each unit containing a predetermined quantity of an aptamer according to the present invention, or a composition containing same calculated to produce the desired therapeutic effect in association with the required pharmaceutical vehicle. The specifications for the dosage unit forms of the disclosure are dictated by and directly dependent on (a) the unique characteristics of the therapeutic agent and the particular therapeutic effect to be achieved, and (b) the limitations inherent in the art of compounding aptamers according to the present invention, or compositions containing same for the prevention of infection with HIV.

In accordance with certain aspects and embodiments of the present invention, there are provided methods of cell-specific delivery of antiviral siRNA to a subject in need thereof, said method comprising administering said antiviral siRNA together with an aptamer as described herein, wherein said antiviral siRNA and said aptamer are optionally linked by a suitable linker.

In accordance with certain aspects and embodiments of the present invention, there are provided methods of identifying HIV-1 susceptible cells, said method comprising:
(a) contacting test cells with an aptamer as described herein, and
(b) identifying those cells which bind to said aptamer as HIV susceptible.

In accordance with certain aspects and embodiments of the present invention, there are provided methods to block viral replication, said method comprising administering an aptamer-siRNA chimera as described herein to a subject in need thereof.

In accordance with certain aspects and embodiments of the present invention, there are provided methods of selectively delivering antiviral siRNAs to HIV-infected cells, said method comprising contacting said cells with an aptamer-siRNA chimera as described herein.

In accordance with certain aspects and embodiments of the present invention, there are provided kits comprising:
  (a) an aptamer as described herein, and
  (b) antiviral siRNA.

In some embodiments of the present invention, the aptamer included in the above-described kit is G-3 (SEQ ID NO: 1).

In accordance with certain aspects and embodiments of the present invention, there are provided in vitro complexes comprising an aptamer as described herein, and human CCR5.

In some embodiments of the present invention, the human CCR5 of the above-described in vitro complex is bound to a solid support. Exemplary solid supports include a protein chip.

In accordance with certain aspects and embodiments of the present invention, there are provided in vitro complexes comprising an HIV infected cell and an aptamer as described herein. In some embodiments, said in vitro complex may further comprise antiviral siRNA, wherein said aptamer and said antiviral siRNA are optionally linked by a suitable linker.

As readily recognized by those of skill in the art, suitable linkers contemplated for optional use herein may be covalent or non-covalent linkers. In embodiments, the linker is chemical linker including a reactive moiety. In embodiments, the linker forms part of a chemical conjugate as described herein. In embodiments, the suitable linker is a nucleotide linker (e.g., 2Us or 8Us). In embodiments, the suitable linker is a chemical linker, which contains a reactive group such as maleimide groups, sulfhydryl reactive groups, succinimidyl esters (often referred to as NHS esters) which react with amines, and the like.

The concept of nucleic acid-based therapeutics (ribozyme, decoy, antisense oligonucleotide, mRNA, aptamer, siRNA, microRNA) has been extensively exploited for the treatment of various human diseases (33). Although they could be employed as stand-alone inhibitors, the combinatorial use of various nucleic acids has shown more potential and advantages, including synergistic effects, prolonged suppression, and especially targeted therapy when a cell-type specific nucleic acid aptamer was adopted (7). In previous studies, investigators have demonstrated that the HIV-1 genome and host genes can be targeted in combination with various antiviral nucleic acids (ribozyme, siRNA, decoy, etc.) in a tailored manner, thereby providing more efficacies in blocking viral replication and preventing the emergence of resistant variants (8,34,35). By functionalizing the cell-specific aptamers with therapeutic agents, the cellular uptake can be enhanced, thereby improving the therapeutic efficacy.

It is also possible to capitalize on the exquisite specificity of an anti-gp120 aptamer to deliver anti-HIV siRNAs into HIV infected cells with the net result that the replication and spread of HIV is strongly inhibited by the combined action of the aptamer and the siRNAs against HIV-1 tat/rev or host dependency factors (HDFs). In this case, the aptamers can function both as targeted delivery reagents and antiviral agents. In the present study, anti-CCR5 RNA aptamers capable of specifically targeting HIV-1 susceptible cells (as delivery agent) and inhibiting HIV-1 infectivity (as antiviral agent) via block of the CCR5 required for HIV-1 to enter cells have been generated.

Live cell-based SELEX methodology relies on the differences between the target cell population (positive cells that express the target of interest) and the control cell population (negative cells that do not express the target protein) (36). By taking advantage of this difference, live cell-based SELEX is able to enrich sequences that selectively bind to the target receptor in its native conformation or original glycosylation pattern of the extracellular domains, and even internalize into the target cells. Considering the limited resource and the risk of changed conformation of purified CCR5 protein after purification, live cell-based SELEX methodology was used to generate cell-type specific RNA aptamers.

In order to minimize nonspecific binding with the non-targeted cells, a counter-selection step was performed with U373-Magi negative cells per cycle prior to positive selection. Subsequently, the unbound RNA pool was transferred to the targeted cells (U373-Magi-CCR5E cells) for positive selection. The cells used for selection should be healthy, with >95% cells alive. Dead cells nonspecifically allow nucleic acids from the hole into their membranes, thereby affecting the efficiency of the selection. A non-enzymatic cell disassociation solution is used here to detach a monolayer of cells.

After nine selection rounds, high throughput sequencing (HTS) technology and bioinformatics analysis were combined to facilitate the rapid identification of individual RNA aptamers and show the library evolution. In contrast to traditional cloning and sequencing approaches, one can obtain and process millions of sequence reads from each round, which provide comprehensive information, such as the basic sequence, total reads, frequency of each unique sequences, distribution of each nucleotide at random region, and the like, thereby aiding in a better understanding of the selection progression and the molecular evolution.

As shown in Table 2 and FIGS. 2A-2H, a significant increase in the frequencies of the top 1,000 unique sequences was observed since the 7th selection round, which suggested that library sequence diversity had dramatically converged. In other words, molecular enrichment is increased during the SELEX procedure; and some specific sequences have been successfully evolved. Consistent with the progression of SELEX assayed by qRT-PCR (see FIG. 1B), a maximal selection convergence and saturation in the molecular enrichment was achieved at the 7th or the 8th selection round. No further increase was observed in subsequent rounds. Furthermore, the percent frequency of each sequence group (see FIG. 2H) indicated that all the groups were progressively evolved from the round 5 to round 7 or 8. The results also demonstrate that after maximal molecular enrichment is reached, subsequently additional selection rounds do not further improve the enrichment. This may be explained in that an increase of one moderate sequence probably occupies the proportion of some better aptamers.

Six representative RNA aptamers from each group showed selective binding affinity and internalization to CCR5 expressing U373-Magi-CCR5E cells. One of the best candidates (G-3 aptamers) has been demonstrated to efficiently bind and internalize into CCR5 expressing T-lymphoblastoid cell line with ~110 nM of apparent $K_d$ values. Importantly, G-3 aptamer was also able to bind and be uptaken to primary peripheral blood mononuclear cells (PBMCs) that were isolated from different donors.

Through specific knockdown of CCR5 expression, a significant loss in binding affinity of G-3 aptamer in CCR5 siRNA treated cells was observed, therefore further validating that the selected G-3 aptamer bound directly to CCR5 protein. It was observed that the aptamer was mainly located within the cytoplasm after cellular internalization, suggesting that the CCR5 aptamer may be internalized by CCR5-mediated endocytosis. These results demonstrate that cell-type specific, internalizing aptamers against CCR5, which may be used a delivery vehicle for siRNA or other therapeutics as previously reported, have been successfully identified.

Human immunodeficiency virus (HIV) replicates primarily in T-lymphocytes and cells of the macrophage lineage. In addition to CD4 that is required for virus binding to the cell surface, coreceptors (CCR5, CXCR4) are required for viral fusion with the cell membrane (16,17,37). M-tropic HIV-1 stains (R5 viruses) use CCR5 for the coreceptor, and T-tropic strains (X4 viruses) use CXCR4. Successes in discovering new classes of CCR5 inhibitors targeted to the step of HIV-1 entry have been reported in recent years. For example, previous studies have demonstrated that the chemokine RANTES (regulated on activation, normal T cell expressed and secreted), a natural CCR5 ligand, and an $NH_2$-terminal modified form of RANTES (AOP-RANTES) protect cells from HIV infection by R5 viruses (31,38). This inhibition of virus infection may be explained by either occupancy of CCR5 and blocking of interaction with the CD4-gp120 complex, or receptor sequestration following internalization (39-41). A "prophylactic" HIV-1 experiment indicated that G-3 aptamer specifically neutralized R5 virus infection in primary PBMCs with a nanomolar $IC_{50}$ value, thereby suggested a selective HIV-1 inhibition. Therefore, CCR5 aptamers show potential as a therapeutic by itself for HIV-1 infection and not exclusively as a delivery vehicle.

In accordance with certain aspects and embodiments of the present invention, TNPO3 siRNA is used as a proof of principle to show the successful delivery (as well as specific gene silencing) in CCR5 expressing CEM cells and human PBMCs. Thus, the aptamer-siRNA sense single strand was co-transcribed, followed by annealing of the complementary siRNA antisense strand to complete the chimeric molecule. The resultant CCR5 aptamer-siRNA delivery systems specifically bind to the surface of the cells expressing CCR5 and are internalized, allowing functional processing of the siRNA into RISC, resulting in specific inhibition of HIV-1 replication in cell culture.

In summary, it has been demonstrated that the combinatorial use of live cell-based SELEX with HTS and bioinformatics analysis not only represents a powerful and rapid method for generating cell-type specific, internalizing aptamers that are able to recognize a particular target membrane protein under native condition, but also provides comprehensive information that could help to better understand the selection progression and improve the evolution efficiency. Additionally, the CCR5 aptamer-based siRNA delivery system serves as dual functional inhibitors and therefore provides better efficacy than either the aptamer or siRNA applied alone. Therefore, the cell-specific, internalizing CCR5 aptamers-functionalized agents offer great promise for cell-type- or tissue-specific delivery of various therapeutic drugs for targeted HIV-1 therapy. Notably, these targeted delivery approaches can be utilized in disease models beyond HIV-1 such as cancer.

Various aspects of the present disclosure are illustrated by the following non-limiting examples. The examples are for illustrative purposes and are not a limitation on any practice of the present disclosure. It will be understood that variations and modifications can be made without departing from the spirit and scope of the disclosure. One of ordinary skill in the art readily knows how to synthesize or commercially obtain the reagents and components described herein.

Those skilled in the art will recognize, or be able to ascertain using no more than routine experimentation, numerous equivalents to the specific procedures, embodiments, claims, and examples described herein. Such equivalents are considered to be within the scope of this disclosure and covered by the claims appended hereto. The contents of all references, issued patents, and published patent applications cited throughout this application are hereby incorporated by reference. The disclosure is further illustrated by the following examples, which should not be construed as further limiting.

EXAMPLES

Unless otherwise noted, all chemicals were purchased from Sigma-Aldrich, all restriction enzymes were obtained from New England BioLabs (NEB) and all cell culture products were purchased from GIBOC (Gibco BRL/Life Technologies, a division of Invitrogen). Sources for the other reagents were: DuraScribe T7 transcription Kit (EPICENTRE Biotechnologies); ThermoScript RT-PCR system (Invitrogen); Silencer siRNA Labeling Kit (Ambion); Hoechst 33342 (nuclear dye for live cells) (Molecular Probes, Invitrogen); M-MLV Reverse transcriptase and Random primers (Invitrogen); Bio-Spin 30 Columns (Bio-Rad); Lipofectamine 2000 (Invitrogen); Trans IT-TKO (Mirus). U373-Magi cells, U373-Magi-CCR5E cells, CEM-NKr cells, CEM-NKr-CCR5 cells, HIV-1$_{JR-FL}$ and HIV-1$_{BaL}$ virus were obtained from the AIDS Research and Reference Reagent Program (22-24).

Primers, DNA library and siRNAs were purchased from Integrated DNA Technologies (IDT, Coralville, Iowa, USA). 51-mer ssDNA oligo library for RNA Library:

Primers, DNA library and siRNAs were purchased from Integrated DNA Technologies (IDT, Coralville, IA, USA). 51-mer ssDNA oligo library for RNA Library:

(SEQ ID NO: 2)
5'-GGG AGG ACG ATG CGG-N20-CAG ACG ACT CGC CCG A-3' (51 nt).

Forward primer:

(SEQ ID NO: 3)
5'-TAA TAC GAC TCA CTA TAG GGA GGA CGA TGC GG-3' (32 mer);

Reverse primer:

(SEQ ID NO: 4)
5'-TCG GGC GAG TCG TCT G-3' (16 mer).

CCR5 siRNA sense:

(SEQ ID NO: 5)
5' P-CUC UGC UUC GGU GUC GAA A dTdT-3';

Antisense:

(SEQ ID NO: 6)
5' P-UUU CGA CAC CGA AGC AGA G dTdT-3'.

TNPO3 DsiRNA sense:

(SEQ ID NO: 7)
5'-CGA CAU UGC AGC UCG UGU ACC AG dGdC-3';

Antisense:

(SEQ ID NO: 8)
5'-GCC UGG UAC ACG AGC UGC AAU GUC GUU-3'.

Example 1

CCR5 (C-C chemokine receptor type 5), a 7 pass transmembrane receptor expressed by T-cells and macrophages, serves as a co-receptor for macrophage-tropic HIV-1. A loss of CCR5 is associated with resistance to HIV-1. It is investigated herein as to whether a combinatorial use of various antiviral nucleic acids (such as small interfering RNAs (siRNAs) and aptamers) could be more efficacious in blocking viral replication and preventing the emergence of resistant variants. By combining the "Live Cell-based SELEX" strategy with high throughput sequencing (HTS) technology and bioinformatics analysis, several 2'-Fluoro-pyrimidine modified RNA aptamers targeted to the human CCR5 have been successfully identified. One of the best candidates (G-3 aptamer) efficiently bound and was internalized into human CCR5 expressing cells. This G-3 aptamer specifically neutralized R5 virus infection in primary PBMCs with a nanomolar $IC_{50}$ value and was capable of shuttling functional siRNAs to CCR5 expressing cells. The data presented here suggest that CCR5 RNA aptamers can not only identify HIV-1 susceptible cells, but also selectively regulate both the inhibition of the CCR5 required for HIV-1 to enter cells and targeted anti-HIV siRNA delivery. Collectively, the cell-specific, internalizing CCR5 aptamers and aptamers-siRNA conjugates described herein offer great promise for cell-type- or tissue-specific delivery of various therapeutic drugs for targeted therapy.

Generation of Aptamer and Aptamer-siRNA Chimeras by In Vitro Transcription

Double-stranded DNA templates were directly generated by PCR, and the resulting PCR products were recovered using a QIAquick Gel purification Kit (Qiagen, Valencia, Calif.). Chimera sense strands were transcribed from its PCR-generated DNA templates using the DuraScription Kit (Epicentre, Madison, Wis.) in accordance with the manufacturer's instructions. In the transcription reaction mixture, the canonical cytidine triphosphate and uridine triphosphate were replaced with 2'-fluoro-cytidine triphosphate and 2'-fluoro-uridine triphosphate to produce RNA that is resistant to RNase A degradation. The reactions were incubated at 37° C. for 6 hours, and subsequently purified using Bio-Spin 30 Columns (Bio-Rad, Hercules, Calif.) after phenol extraction and ethanol precipitation. Fluorescent dye-labeled RNAs were generated using the Silencer siRNA labeling kit (Ambion, Austin, Tex.) in accordance with the manufacturer's instructions. The sense strands of the chimeras are underlined. The italic UU is the linker between the aptamer and siRNA portions. The assembly of these chimeric constructs was described previously (25) and a schematic is presented in FIGS. 5A-5B.

G-3 aptamer:

(SEQ ID NO: 9)
5'-GGG AGG ACG AUG CGG GCC UUC GUU UGU UUC GUC CAC AGA CGA CUC GCC CGA-3'

G-3-TNPO3 OVH chimera sense strand:

(SEQ ID NO: 10)
5'-GGG AGG ACG AUG CGG GCC UUC GUU UGU UUC GUC CAC AGA CGA CUC GCC CGA *UU* CAA AGC CGA CAU UGC AGC UCG UGU ACC-3';

Antisense:

(SEQ ID NO: 11)
5'-UAC ACG AGC UGC AAU GUC GGC UUU G-3'

G-3-TNPO3 Blunt chimera sense strand:

(SEQ ID NO: 12)
5'-GGG AGG ACG AUG CGG GCC UUC GUU UGU UUC GUC CAC AGA CGA CUC GCC CGA *UUUUUUUU* CGA CAU UGC AGC UCG UGU ACC AGG C-3';

Antisense:

(SEQ ID NO: 13)
5'-GCC UGG UAC ACG AGC UGC AAU GUC GGC-3'

G-3-Scrambled siRNA chimera sense strand:

(SEQ ID NO: 14)
5'-GGG AGG ACG AUG CGG GCC UUC GUU UGU UUC GUC CAC AGA CGA CUC GCC CGA *UU* ACG UGA GAC GUU CGG UGA AUU-3';

Antisense strand:

(SEQ ID NO: 15)
5'-UUC ACC GAA CGU CUC ACGUdTdT-3'

Example 2

Cell Lines and Cell Culture

All cells were cultured in a humidified 5% $CO_2$ incubator at 37° C. U373-Magi cells and U373-Magi-CCR5E cells were obtained through the AIDS Research and Reference Reagent Program. Both cell lines were adherent cell lines and split 1:10 or 1:5 once per week upon reaching confluence by washing with DPBS and detaching cells using Cell stripper (Cellgro, Mediatech Inc) in order to minimize the damage to the cellular surface receptors. Each cell line was carried for no more than 15 passages. U373-Magi were cultured in 90% DMEM supplemented with 10% fetal bovine serum, 0.2 mg/ml G418 and 0.1 mg/ml hygromycin B. U373-Magi-CCR5E cells were cultured in 90% DMEM supplemented with 10% fetal bovine serum, 0.2 mg/ml G418, 0.1 mg/ml hygromycin B and 1.0 μg/ml puromycin.

CCRF-CEM cells were purchased from ATCC and CEM-NKr cells and CEM-NKr-CCR5 cells were obtained through the AIDS Research and Reference Reagent Program. CEM cell lines were suspension cell lines and split 1:10 once per week upon reaching confluence. They were cultured in RPMI-1640 supplemented with 10% FBS.

PBMCs: Peripheral blood mononuclear samples were obtained from healthy donors from the City of Hope National Medical Center. PBMCs were isolated from whole blood by centrifugation through a Ficoll-Hypaque solution (Histopaque-1077, Sigma). CD8 cells (T-cytotoxic/suppressor cells) were depleted from the PBMCs by CD8 Dynabeads (Invitrogen, CA) according to the manufacturer's instructions. CD8+ T cell-depleted PBMCs were washed twice in PBS and resuspended in culture media (RPMI 1640 with 10% FBS, 1 (PenStrep and 100 U/ml interleukin-2). Cells were cultured in a humidified 5% $CO_2$ incubator at 37° C.

Example 3

Detect the Cell Surface Target Protein (CCR5) Expression by Flow Cytometry Analysis For cell-surface CCR5 protein staining, adherent cell lines (U373-Magi cells and U373-Magi-CCR5E cells) were washed with pre-warm PBS and detached with Cell stripper. Suspension cell lines (CEM-NKr cells, CEM-NKr-CCR5 cells, and PBMCs) were washed with pre-warmed PBS. After counting the cells' number, the desired number of cells was resuspended in 100 μL binding buffer and added APC mouse Anti-human CD195 antibody (BD Pharmingen). For example, 1 μL antibody was enough for $2\times10^5$ cells in 100 μL reaction system. After incubation for 30 min at room temperature in the dark, cells were washed twice with 500 μL of washing buffer, finally resuspended in 350 of DPBS and processed immediately for flow cytometry (Flow cytometry core, City of Hope, Calif.).

Example 4

Live Cell-Based SELEX

The starting DNA library contained 20 nt of random sequences and was synthesized by Integrated DNA Technologies (Coralville, Iowa, USA). The random region is flanked by constant regions, which include the T7 promoter (underlined) for in vitro transcription and a 3'-tag for reverse transcription-polymerase chain reaction (RT-PCR). 51-mer ssDNA oligo library for RNA Library is:

```
                                      (SEQ ID NO: 2)
5'-GGG AGG ACG ATG CGG-N20-CAG ACG ACT CGC CCG A-
3' (51 nt).
```

The 5' and 3' constant sequences are:

```
                                      (SEQ ID NO: 3)
5'-TAA TAC GAC TCA CTA TAG GGA GGA CGA TGC GG-3'
(32 mer)
and
                                      (SEQ ID NO: 4)
5'-TCG GGC GAG TCG TCT G-3' (16 mer), respectively.
```

The DNA random library (0.4 μM) was amplified by PCR using 3 μM each of 5'- and 3'-primers, along with 2 mM $MgCl_2$ and 200 μM of each dNTP. To preserve the abundance of the original DNA library, PCR was limited to 10 cycles. The PCR amplification protocol is as follows: 93° C. for 3 min, followed by 10 cycles of heating to 93° C. for 1 min, 63° C. for 1 min and 72° C. 1 min. A final extension step was performed for 7 min at 72° C.

After the PCR reactions (10 reactions, 100 μl per reaction), the amplified dsDNA pool was recovered using a QIAquick Gel purification Kit. The resulting dsDNA was converted to an RNA library using the DuraScription Kit (Epicentre, Madison, Wis., USA) according to the manufacturer's instructions. In the transcription reaction mixture, CTP and UTP were replaced with 2'-F-CTP and 2'-F-UTP to produce ribonuclease resistant RNA. The reactions were incubated at 37° C. for 6 h, and subsequently the template DNA was removed by Dnase I digestion. The transcribed RNA pool was purified in an 8% polyacrylamide/7 M urea gel. The purified RNA library was quantified by ultraviolet spectrophotometry.

SELEX was performed principally as described by Tuerk and Gold (26), applying the modified cell-based SELEX described by Thiel et al (27-30). Generally, in each round, the desired amount of RNA pools were refolded in 3 mL of refolding buffer, heated to 65° C. for 5 min and then slowly cooled to 37° C. Incubation was continued at 37° C. for 10 min. The refolding or washing buffer contained DPBS (pH 7.0~7.4) and $Ca^{2+}$ and $Mg^{2+}$, 1 mM $CaCl_2$, 2.7 mM KCl, 1.47 mM $KH_2PO_4$, 1 mM $MgCl_2$, 136.9 mM NaCl, 2.13 mM $Na_2HPO_4$. The binding buffer used during the selection was prepared by adding yeast tRNA to washing buffer to reduce non-specific binding. To avoid nonspecifically interaction between nucleic acids and the cell surface, the tRNA (100 μg/mL) as a competitor was first incubated with non-targeted cells or targeted cells at 37° C. for 25 min and then ready for selection step. Coulter-selection step was performed per cycle to minimize nonspecific binding with the non-targeted cells. Subsequently, the unbound RNA pool was transferred to the targeted cells for positive selection.

For the first cycle of selection, 24 hours before selection, U373-Magi negative cells and U373-Magi-CCR5E positive cells were seeded at equal density ($5*10^6$ cells per plate) on 150 mm tissue culture dish with 25 mL complete culture medium. On the day of selection, U373-Magi negative cells were washed three times with 15 mL pre-warmed washing buffer to remove dead cells and then added 15 mL pre-warmed binding buffer supplemented with 100 μg/mL yeast tRNAs. After 25 min incubation at 37° C., the buffer was removed and the refolded RNA pool (4 nmol 0-RNA pool in 15 mL refolding buffer) was added to the U373-Magi negative cells for 30 min at 37° C. The pre-cleared 0-RNA pool (supernatants with unbound sequences from negative cells plate) was ready for positive selection.

Meanwhile, as described above, U373-Magi-CCR5E positive cells were also washed and incubated with 15 mL pre-warmed binding buffer supplemented with 100 μg/mL yeast tRNAs. After 25 min incubation at 37° C., the buffer was removed and the pre-cleared 0-RNA pool was subsequently transferred to the U373-Magi-CCR5E positive cells for 30 min at 37° C. Following incubation of the pre-clear RNA pool, the U373-Magi-CCR5E positive cells were washed twice with 12 mL pre-warm washing buffer to remove unbound sequences and cell-surface RNAs with weak binding. Cell-surface bound RNA with strong binding affinity and internalized RNA sequences were recovered by TRIzol (Invitrogen) extraction by following the manufacturer's instructions.

The recovered RNA pool was reverse transcribed using the ThermoScript RT-PCR system (Invitrogen) and amplified for 15 cycles of PCR. The PCR amplification protocol is as follows: 95° C. for 5 min, followed by 15 cycles of heating to 95° C. for 1 min, 63° C. for 1 min and 72° C. 1 min. A final extension step was performed for 7 min at 72° C. After the amplified dsDNA template was purified a QIAquick Gel purification Kit, it was transcribed to new RNA pool as described above for the next round of selection. With the SELEX progress, the cells number, density, volume, RNA amount, washing times, tRNA competitor amount, and incubation time were progressively adjusted in order to increase the pressure of aptamer selection. The numbers of cells, plate size, medium volume, the amount of RNA pool and tRNA, washing condition, incubation time and selection conditions are summarized in Table 1.

TABLE 1

| SELEX rounds | Positive cells (plate size and medium volume) | Negative cells (plate size and medium volume) | RNA pool (incubation time) | RNA work Con. | Competitor tRNA | Washing |
|---|---|---|---|---|---|---|
| 1 | 3 * 10⁶ cells (15 cm, 15 mL) | 3 * 10⁶ cells (15 cm, 15 mL) | 4 nmol (30 min) | 333 nM | 0 | 2 × 12 mL |
| 2 | 3 * 10⁶ cells (15 cm, 15 mL) | 3 * 10⁶ cells (15 cm, 15 mL) | 4 nmol (25 min) | 333 nM | 2.5 nmol | 3 × 12 mL |
| 3 | 1.5 * 10⁶ cells (10 cm, 12 mL) | 3 * 10⁶ cells (10 cm, 12 mL) | 2.5 nmol (25 min) | 208 nM | 5 nmol | 4 × 12 mL |
| 4 | 1.5 * 10⁶ cells (10 cm, 12 mL) | 3 * 10⁶ cells (10 cm, 12 mL) | 2.5 nmol (20 min) | 208 nM | 15 nmol | 5 × 12 mL |
| 5 | 7.5 * 10⁵ cells (6 cm, 8 mL) | 2.25 * 10⁶ cells (10 cm, 8 mL) | 1.5 nmol (20 min) | 188 nM | 15 nmol | 6 × 8 mL |
| 6 | 7.5 * 10⁵ cells (6 cm, 8 mL) | 2.25 * 10⁶ cells (10 cm, 8 mL) | 1.5 nmol (15 min) | 188 nM | 20 nmol | 6 × 8 mL |
| 7 | 3 * 10⁵ cells (3.5 cm, 5 mL) | 1.5 * 10⁶ cells (6 cm, 5 mL) | 0.8 nmol (15 min) | 160 nM | 20 nmol | 7 × 5 mL |
| 8 | 3 * 10⁵ cells (3.5 cm, 5 mL) | 1.5 * 10⁶ cells (6 cm, 5 mL) | 0.8 nmol (10 min) | 160 nM | 40 nmol | 8 × 5 mL |
| 9 | 1.5 * 10⁵ cells (3.5 cm, 5 mL) | 1.2 * 10⁶ cells (6 cm, 5 mL) | 0.5 nmol (10 min) | 100 nM | 40 nmol | 9 × 5 mL |

Note:
1) To avoid nonspecific interaction between nucleic acids and the cell surface, the tRNA (100 μg/mL) as a competitor was first incubated with non-targeted cells or targeted cells at 37° C. for 25 min and then ready for selection step.
2) Counter-selection: RNA pool was incubated with U373-Magi negative cells at 37° C. for 30 min.

Example 5

Monitor the Progress of SELEX by Quantitative Real-Time PCR (qRT-PCR)

qRT-PCR methods were applied to monitor SELEX progress. Twenty-four hours before experiment, U373-Magi negative cells and U373-Magi-CCR5E positive cells were seeded at equal density (3×10⁴ cells per well) on 48-well plate with 250 μL complete culture medium. On the day of the experiment, both cells were washed three times with 250 μL pre-warmed washing buffer to remove dead cells and then incubated with 250 pre-warmed binding buffer supplemented with 100 μg/mL yeast tRNA at 37° C. for 15 min. After incubation, the buffer was removed and the refolded RNA pool (0.1 nmol RNA pool in 250 μL refolding buffer) supplemented with 1 nmol yeast tRNA was added to the U373-Magi negative cells or CCR5 positive cells for 15 min at 37° C. Following incubation of the RNA pool, the cells were washed six times with 250 μL washing buffer to remove unbound RNA and cell-surface RNAs with weak binding. Cell-surface bound RNA with strong binding affinity and internalized RNA sequences were recovered by TRIzol (Invitrogen) extraction by following the manufacturer's instructions. The recovered RNA pool was reverse transcribed using the ThermoScript RT-PCR system (Invitrogen). The resulting cDNA was further analyzed by quantitative RT-PCR using 2× iQ SyberGreen Mastermix (Bio-Rad) as described in the manufacturer's instructions and GAPDH expression was used for normalization of the qPCR data.

specific primer sets for the RNA pool at final concentrations of 400 nM. Primers were as follows:

```
RNA pool Forward primer:
                                        (SEQ ID NO: 16)
5'-TAA TAC GAC TCA CTA TAG GGA GGA CGA TGC
GG-3' (32 mer);

RNA pool Reverse primer:
                                        (SEQ ID NO: 17)
5'-TCG GGC GAG TCG TCT G -3' (16 mer).
```

```
GAPDH forward primer:
                                        (SEQ ID NO: 18)
5'-CAT TGA CCT CAA CTA CAT G-3';

GAPDH reverse primer:
                                        (SEQ ID NO: 19)
5'-TCT CCA TGG TGG TGA AGA C-3'.
```

Example 6

Illumina High-Throughput Sequencing and Data Analysis

After 9 rounds of SELEX, the RNA pools for selection rounds 5, 6, 7, 8 and 9 were chosen for Illumina high-throughput sequencing analysis. The sample preparation and sequencing processing were performed by City of Hope DNA sequencing core (City of Hope, Calif., USA). Briefly, 1.0 μg of RNA pool was first reverse-transcribed using RT primer:

```
                                        (SEQ ID NO: 20)
5' CAG ATT GAT GGT GCC TAC AGT CGG GCG UGT CGT
CTG 3',
``` then subjected to PCR amplification for 8 cycles, using the primers:

JH5

(SEQ ID NO: 21)
(5' AAT GAT ACG GCG ACC ACC GAC AGG TTC AGA GTT CGA TCG GGA GGA CGA TGC GG 3')
and RT/index primer (SEQ ID NO: 22)
(5' CAG ATT GAT GGT GCC TAC AGT CGG GCG UGT CGT CTG 3')

then followed by 6% TBE PAGE gel purification with size selection (for targeted smRNAs of 51 nt). The purified library was followed by a second round of PCR amplification for 4 cycles with primers PE-mi-index primer:

(SEQ ID NO: 23)
5' CAA GCA GAA GAC GGC ATA CGA GAT NNNNNN CAG ATT GAT GGT GCC TAC AG 3'
and (SEQ ID NO: 24)
R2 (5' AAT GAT ACG GCG ACC ACC GA 3')

then followed by 6% TBE PAGE gel purification with size selection (for targeted smRNAs of 51 nt). The purified library was followed by quantified using qPCR with a forward primer:

(SEQ ID NO: 25)
5' CAA GCA GAA GAC GGC ATA CG
and a reverse primer (SEQ ID NO: 26)
(5' AAT GAT ACG GCG ACC ACC GA 3').

The quantified denatured miRNA library was loaded in 1 mL of hybridization buffer to a final DNA concentration of 10 pM then used for single read flow cell cluster generation and 40 cycle (40 nt) sequencing performed using the Illumina HiSeq2000.

Reads processing and data analysis were conducted using the following processing principles. Bases after Ns in each read were considered low quality and were removed. The 3'-fixed oligo and 3'-Solexa adapter were identified and trimmed from each reads. The reads with 20-base after processing were considered as usable reads and retained for further analysis. Unique reads in each sample were counted. The most frequent 1,000 unique sequences were identified in each sample. The most frequent 1,000 unique sequence in round 9 were obtained and matched to the other four samples (top 1,000 unique reads) and their frequencies were recorded. The consensus sequence of round 9 was used to compare to the reads in each round. For alignment and grouping analysis, the top 40 sequences were divided into 6 groups according to their predicted secondary structures by MFold RNA and QuickFold RNA.

Example 7

Cell-Surface Binding of Experimental RNAs (Flow Cytometry Analysis)

Adherent cell lines (U373-Magi cells and U373-Magi-CCR5E cells) were washed with pre-warmed PBS and detached with Cell stripper. Suspension cell lines (CEM-NKr cells, CEM-NKr-CCR5 cells, and PBMCs) were washed twice with pre-warmed PBS. After counting the cells' number, the desired number of cells was resuspended in 100 µL binding buffer containing Cy3-labeled experimental RNA aptamers at different concentrations as shown. After incubation at room temperature for 30 min, cells were washed three times with 500 µL of pre-warmed binding buffer, and finally resuspended in 350 µL of DPBS for flow cytometry analysis (Flow cytometry core, City of Hope, Calif.). The dissociation constants were calculated using non-liner curve regression with a Graph Pad Prism 6.0.

Similarly, G-3-27-mer-TNPO3 OVH chimera was chosen for binding affinity test with PBMC-CD4+ cells, CEM-NKr-CCR5 positive cells, and CEM negative cells. The aptamer-sense strand and antisense strand of the chimera were labeled by Cy3 and Cy5 dye, respectively. And then they (200 nM) were annealed to form aptamer-siRNA chimera for flow cytometry analysis as described above.

Example 8

Internalization and Intercellular Localization Studies (Live-Cell Confocal Microscopy Analyses)

Adherent cell lines (U373-Magi cells and U373-Magi-CCR5E cells) were grown in 35-mm plate pre-treated with poly-lysine (Glass Bottom Dish, MatTek, Ashland, Mass., USA) with seeding at $3\times10^5$ cells in complete cell culture medium to allow about 70-80% confluence in 24 hours. On the day of the experiments, cells were washed with 2 mL of pre-warmed PBS, and incubated with 1.5 mL of pre-warmed, fresh complete growth medium for 30 min at 37° C. Cy3-labeled, refolded experimental RNAs at a 67 nM final concentration were added to media and incubated for live-cell confocal microscopy in a 5% $CO_2$ microscopy incubator at 37° C. The images were collected every 20 min using a Zeiss LSM 510 Meta Inverted 2 photon confocal microscopy system under water immersion at 40× magnification (Confocal microscopy core, City of Hope, Calif.). After 5-6 h of incubation and imaging, the cells were stained by treatment with 0.15 mg/ml Hoechst 33342 (nuclear dye for live cells, Molecular Probes, Invitrogen, CA, USA) according to the manufacturer's instructions. The images were collected as described previously.

For suspension cell lines (CEM-NKr cells, CEM-NKr-CCR5 cells, and PBMCs), on the day of experiments, cells were washed twice with pre-warmed PBS and seeded in the polylysine-coated 35-mm plate as described above with seeding at $1\times10^6$ cells in the pre-warmed RPMI-1640 medium supplemented with 10% FBS. Cells were incubated for 30-60 min in a humidified 5% $CO_2$ incubator at 37° C. for attaching on the dish surface. As described above, Cy3-labeled, refolded experimental RNAs at a 67 nM final concentration were added to media and images were collected using a Zeiss LSM 510 Meta Inverted two proton confocal microscopy system (Confocal microscopy core, City of Hope, Calif.).

Example 9

CCR5 Knockdown Experiment (qRT-PCR and Flow Cytometry Assay)

The CCR5 siRNA (sense: 5' P-CUC UGC UUC GGU GUC GAA A dTdT—3'(SEQ ID NO:27); Antisense: 5' P-UUU CGA CAC CGA AGC AGA G dTdT—3'(SEQ ID NO:28)) has been demonstrated previously to knockdown CCR5 expression. The CCR5 siRNA and control non-silencing siRNA NC-1 (IDT, Iowa, USA) were transfected to U373-Magi-CCR5E cells using commercial Lipofectamine 2000 (Invitrogen) according to the manufacturer's instructions.

To assess silencing at the mRNA level, after 48 hours of transfection, total RNA was isolated with STAT-60 (TEL-TEST, Friendswood, Tex., USA) according to the manufacturer's instructions. Residual DNA was digested using the DNA-free kit per the manufacturer's instructions (Ambion, Calif., USA). cDNA was produced using 2 µg of total RNA Moloney murine leukaemia virus reverse transcriptase (M-MLV RT) and random primers in a 15-µl reaction according to the manufacturer's instructions (Invitrogen, CA, USA). Expression of the CCR5 coding RNAs was analyzed by quantitative RT-PCR using 2× iQ SyberGreen Mastermix (BIO-RAD) and specific primer sets at a final concentration of 400 nM. Primers were as follows:

```
CCR5 forward primer:
                               (SEQ ID NO: 29)
5'-AAC ATG CTG GTC ATC CTC AT-3';

CCR5 reverse primer:
                               (SEQ ID NO: 30)
5'-AAT AGA GCC CTG TCA AGA GT-3'.
```

GAPDH expression was used for normalization of the qPCR data.

To assess silencing at the protein level, after 48 hours of transfection, cells were washed with 500 µL pre-warmed PBS and detached with Cell stripper. The cell-surface CCR5 protein staining was performed with APC-CD195 antibody as described above. Cells were immediately analyzed by flow cytometry (Flow cytometry core, City of Hope, Calif.).

Example 10

Protection of HIV-1 Infection in PBMCs (HIV-1 Challenges and p24 Antigen Assay)

PBMCs were freshly isolated from healthy donors and CD8 cells were depleted as described above. After culture for 3 days in the activated T-cell culture medium containing interleukin-2, the cell-surface CCR5 level of PBMCs was detected by flow cytometry as described previously. HIV-1 protection assay was performed in 24-well tissue culture plates. Duplicate night-point dilution series of experimental RNAs were prepared and refolded in refolding buffer. PBMCs were washed once with pre-warmed PBS, and 4×10$^5$ PBMCs were seeded to each well of assay plates. Subsequently, experimental RNAs with different concentrations were added. Plates were incubated for 4-6 hours at 37° C. in a humidified 5% CO$_2$ incubator. Various viruses (R5 strains: JR-FL, Bal, MOI=0.01; or X4 strains: IIIB, NL4-3, MOI=0.001) were added into each well. After 24 hours incubation, the cells were gently washed with pre-warmed PBS to eliminate free viruses and were incubated sequentially at 37° C. in a humidified 5% CO$_2$ incubator.

The culture supernatants were collected at different time points after infection (3, 5 and 7 days). The HIV-1 p24 antigen analyses were performed using a Coulter HIV-1 p24 antigen assay (Beckman Coulter, Fullerton, Calif.) in accordance with the manufacturer's instructions. The percentage inhibition of HIV-1 infection for each concentration of experimental RNAs was calculated to determine the anti-HIV-1 IC$_{50}$ value (50% inhibitory concentration) using non-liner curve regression with a Graph Pad Prism 6.0.

Example 11

TNPO3 Knockdown Experiment (qRT-PCR)

A total of 2×10$^5$ cells (CEM-NKr-CCR5, CEM-Nkr negative cells, Primary PBMCs) were directly incubated with G-3 aptamer and chimeras (400 nM). In parallel, 50 nM of experimental RNAs were transfected by a commercial transfection agent (Trans IT-TKO) according to the manufacturer's instructions. As a control, unrelated aptamer-siRNA chimera (anti-gp120 A-1 aptamer) and G-3 aptamer-scrambled siRNA chimera were used. After 48 hours of incubation, total RNA was isolated with STAT60 (TEL-TEST, Friendswood, Tex., USA) according to the manufacturer's instructions. Residual DNA was digested using the DNA-free kit per the manufacturer's instructions (Ambion, Calif., USA). cDNA was produced using 2 µg of total RNA. Reverse transcription was carried out using Moloney murine leukaemia virus reverse transcriptase (MMLV-RT) and random primers in a 15 µL reaction according to the manufacturer's instructions (Invitrogen, CA, USA). Expression of the TNPO3 coding RNAs was analyzed by quantitative RT-PCR using 2× iQ SyberGreen Mastermix (BIO-RAD) and specific primer sets at a final concentration of 400 nM. Gapdh expression was used for normalization of the qPCR data. Primers were as follows:

```
TNPO3 Forward primer:
                               (SEQ ID NO: 31)
5'- CCT GGA AGG GAT GTG TGC -3';

TNPO3 Reverse primer:
                               (SEQ ID NO: 32)
5'- AAA AAG GCA AAG AAG TCA CAT CA -3'.
```

Experiments were performed in triplicate.

Example 12

5'-RACE PCR Assay to Detect In Vivo RNAi Mediated Target mRNA Cleavage

Total RNA was isolated from CEM-NKr-CCR5 cells treated with different experimental chimeras as described above. Residual DNA was digested using the DNA-free kit per the manufacturer's instructions (Ambion). Subsequently, total RNAs (10 µg) were ligated to a GeneRacer adaptor (Invitrogen, 5'-CGA CUG GAG CAC GAG GAC ACU GAC AUG GAC UGA AGG AGU AGA AA-3' (SEQ ID NO:33)) without prior treatment. Ligated RNA was reverse transcribed using a gene specific primer 1 (TNPO3 GSP-Rev-1: 5'-CAG GTA ACA CTG TAA GGA TCT CCA GC-3'(SEQ ID NO:34)) To detect cleavage products, nested PCR was performed using primers complementary to the RNA adaptor:

```
5'-cDNA primer:
                               (SEQ ID NO: 35)
5'- GGA CAC TGA CAT GGA CTG AAG GAG TA -3';
``` gene-specific primers 2 and 3:

```
TNPO3 GSP-Rev-2:
                               (SEQ ID NO: 36)
5'- TAA AGA GGC ATG AGA GTC TGT GGG GA -3';
and
```

```
TNPO3 GSP-Rev-3:
                                            (SEQ ID NO: 37)
5' CCG GAT CTG TAA CAA CTG GTC TGA GA -3'.
```

Amplification products were resolved by agarose gel electrophoresis and visualized by ethidium bromide staining. The specific PCR products were recovered using a QIAquick Gel purification Kit and then were cloned into TOPO TA cloning vector pCR®4-TOPO vector (Invitrogen). Individual clones were identified by DNA sequencing.

Example 13

Interferon Assays by qRT-PCR

As described previously, total RNA was isolated from PBMCs treated with experimental RNAs (400 nM) using STAT-60. Expression of mRNAs encoding p56(CDKL2) and OAS1 were analyzed by quantitative RT-PCR using 2× iQ SyberGreen Mastermix (BIO-RAD) as described above and specific primer sets for these genes at final concentrations of 400 nM. Primers were as follows:

```
P56 (CDKL2) forward,
                                            (SEQ ID NO: 38)
5'- TCA AGT ATG GCA AGG CTG TG -3';

P56 (CDKL2) reverse,
                                            (SEQ ID NO: 39)
5'- GAG GCT CTG CTT CTG CAT CT -3';

OAS1 forward,
                                            (SEQ ID NO: 40)
5'- ACC GTC TTG GAA CTG GTC AC -3';

OAS1 reverse,
                                            (SEQ ID NO: 41)
5'- ATG TTC CTT GTT GGG TCA GC -3';
``` gapdh expression was used for normalization of the qPCR data. INF-α was used as a positive control.

Example 14

HIV-1 Challenges Assay

Human PBMCs were freshly isolated from healthy donors and CD8 cells were depleted as described above. After culture for 3 days in the activated T-cell culture medium containing interleukin-2, the cell-surface CCR5 level of PBMCs was detected by flow cytometry as described previously. PBMCs were washed once with pre-warmed PBS, and $4 \times 10^5$ PBMCs were seeded to each well of assay plates. Subsequently, experimental RNAs (800 nM work concentration) were added. Plates were incubated for 4-6 hours at 37° C. in a humidified 5% $CO_2$ incubator. HIV-1 R5 strains (JR-FL, MOI=0.01) were added into each well. After 24 hours incubation, the cells were gently washed with pre-warmed PBS to eliminate free viruses and were incubated sequentially at 37° C. in a humidified 5% $CO_2$ incubator. The culture supernatants were collected at different time points after infection (3, 5 and 7 days). The HIV-1 p24 antigen analyses were performed using a Coulter HIV-1 p24 antigen assay (Beckman Coulter, Fullerton, Calif.) in accordance with the manufacturer's instructions. The total RNA was isolated for qRT-PCR analysis.

Example 15

Live Cell-Based SELEX of CCR5 Aptamers

RNA aptamers, 2'-Fluoropyrimidine modified, were selected using the "Live cell-based SELEX" strategy (27-30) (see FIG. 1A). Cellular surface CCR5 expression in target U373-Magi-CCR5E cells was first verified using flow cytometric analysis. A counter-selection step was performed with U373-Magi negative cells per cycle prior to positive selection which encompassed the cells density, number and incubation times being reduced, and competitor tRNA and washing times were progressively increased in order to increase the stringency of aptamer selection. The detailed selection conditions are summarized in FIG. 1A-1B and Table 1.

Nine selection rounds containing positive selection and counter-selection were performed with cell-specific binding and internalization of the RNA pools at each selection monitored using quantitative RT-PCR (qRT-PCR). A significant enrichment was observed between the $7^{th}$ (7-RNA pool) to the $9^{th}$ round RNA pool (9-RNA pool) (see FIG. 1B). No further increase could be detected after the $8^{th}$ selection round, suggesting that maximal binding/internalization of the RNA pool may have been reached.

Example 16

Identification of CCR5 Aptamers Using High-Throughput Sequencing (HTS)

By using barcode based-Illumina deep sequencing technology, high throughput Sequencing (HTS) was performed for the RNA pools from selection round 5 to 9 with approximately 30~50 million total reads obtained from each sequenced round (see Table 2A). The raw reads were filtered based on the length of the RNA library constant region and the most frequent 1,000 unique sequences identified (see Table 2A and FIG. 2A). A significant increase in the frequencies of the top 1,000 unique sequences was observed after the $7^{th}$ selection round, suggesting a decrease in library sequence diversity and an increase in library sequence enrichment. Supporting this notion are the observations that after round 7 the molecular diversity was dramatically converged, thereby suggesting some specific sequences have been successfully enriched during the selection (see FIG. 2B). These observations are consistent with previous studies using SELEX (see FIG. 1B).

Table 2A presents a bioinformatics analysis of high throughput sequence data from selection rounds. The total reads and useful reads are defined as follows. The 3'-fixed oligo sequence and 3'-Solexa adapter were identified and trimmed from each read. The reads with 20-base (random domain) after processing were considered as usable reads and retained for further analysis. The most frequent 1,000 unique sequences were identified and listed here for the clarity. The molecular enrichment at each round was calculated by the formula:

total reads of top 1000 unique sequences at round X/round 5.

TABLE 2A

|  | Round 5 | Round 6 | Round 7 | Round 8 | Round 9 |
|---|---|---|---|---|---|
| Total Reads | 8,175,338 | 7,973,185 | 6,503,548 | 7,876,693 | 30,723,210 |
| Useful Reads | 5,003,576 | 4,043,982 | 5,650,155 | 7,994,328 | 16,273,964 |
| Total Reads of top 1000 unique sequences | ,553,154 | 1,877,699 | 8,721,730 | 5,831,299 | 15,473,124 |
| Molecular Enrichment (fold) | .00 | .72 | 2.05 | 0.19 | 9.96 |

Table 2B presents a bioinformatics analysis of RNA aptamers to identify related sequence and structure groups. After alignment of the top 40 sequences, six groups of RNA aptamers were identified. The representative RNA aptamers and the reads of each group are listed here. Only the random sequences of the aptamer core regions (5'-3') are indicated. Group 2, 4 and 5 (G-2, G-4 and G-5 aptames) shared a conserved sequence, which is comprised of 10 nucleotides UUCGUCUG(U/G)G (SEQ ID NO:42).

groups was observed from round 5 to round 7, where the maximal selection convergence or binding/internalization of the RNA pool has been achieved (see Table 2 and FIG. 1B). Importantly, a significant increase of group 1 sequence observed at round 9 comprised a population of other groups, implying further selection may adversely affect the enrichment of the candidate aptamers.

TABLE 2B

| Group | | 20-nt random RNA sequence | Reads of each group | | | | |
|---|---|---|---|---|---|---|---|
| | | | Round 5 | Round 6 | Round 7 | Round 8 | Round 9 |
| 1 | -1 | AUCGUCUAUUAGUCGCUGGC (SEQ ID NO: 43) | 44,560 | ,405,945 | ,385,441 | ,572,509 | ,228,896 |
| 2 | -2 | UCCUUGGCUUUUCGUCUGUG (SEQ ID NO: 44) | 47,271 | ,700,796 | ,191,611 | ,572,814 | ,151,265 |
| 3 | -3 | GCCUUCGUUUGUUUCGUCCA (SEQ ID NO: 45) | 09,975 | ,033,703 | ,150,589 | ,452,540 | ,427,892 |
| 4 | -4 | UCCCGGCUCGUUCGUCUGUG (SEQ ID NO: 46) | 29,752 | 95,110 | ,564,701 | ,568,638 | ,148,903 |
| 5 | -5 | UUCGUCAU UUUUCGUCUGGG (SEQ ID NO: 47) | 08,652 | ,282,740 | ,133,297 | ,591,731 | 01,763 |
| 6 | -6 | CCUUUCGUCUGUUUCUGCGC (SEQ ID NO: 48) | 9,760 | 58,855 | 33,840 | 59,454 | 4,378 |
| Others | | Orphan sequences | 0,151 | 2,315 | | | |
| | | Total Reads of all groups | ,430,121 | ,319,464 | 7,659,479 | 4,917,686 | 4,753,097 |

The distribution of each nucleotide (A, T, C, G) at the 20-nt random region within the RNA sequence of the top 1000 candidates from each round was identified (see FIGS. 2C-2G). The individual sequences were classified into six major groups (Group 1-6) based on the alignments of the top 1000 unique aptamer sequences (see Table 2B). One representative sequence from each group (G-1, G-2, G-3, G-4, G-5 and G-6) was listed for further characterization because of their relative abundance within their group. Theoretical secondary structures were predicted by using RNA folding algorithm Mfold. Group 2, 4 and 5 (G-2, G-4 and G-5 aptames) shared a conserved sequence, which is comprised of 10 nucleotides UUCGUCUG(U/G)G (SEQ ID NO:42). Furthermore, the percent frequency was calculated to determine the evolution of each sequence group from the round 5 to 9 (see FIG. 2H). A progressive evolution of all the

Example 17

CCR5 RNA Aptamers Bind and are Internalized into CCR5-Expressing Cells

To evaluate the binding affinity and internalization potential of these individual RNA aptamers, one representative sequence from each group (G-1, G-2, G-3, G-4, G-5 and G-6) was synthesized for further characterization. U373-Magi cells stably expressing the CCR5 protein and its parental U373-Magi (CCR5 negative) control cells were used to test for binding and internalization of the candidate aptamers. Cell-specific binding and internalization was firstly detected by using quantitative RT-PCR (qRT-PCR). These RNA aptamers showed selective binding/internalization to U373-Magi-CCR5E positive cells (see FIG. 3A). Next, these RNA aptamers were labeled with Cy3 dye and their binding and cellular uptake were determined. Flow cytometric analysis revealed that the aptamers specifically bound to the U373-Magi-CCR5E positive cells but did not bind to the control U373-Magi negative cells (see FIG. 3B).

To determine the ability of the candidate aptamers to selectively bind to different cells expressing human CCR5, the ability of the aptamers to bind human T-lymphoblastoid cell line (CEM-NKr-CCR5 cell) and primary peripheral blood mononuclear cells (PBMCs) isolated from different donors was determined. The top candidate aptamer, G-3, was selected for further analysis as it was able to bind CCR5 in the various CCR5 expressing cells and was refractory to binding the non-CCR5 expressing control cells (see FIG. 3C). The cell surface binding constant ($K_d$) of the G-3 aptamer was evaluated by flow cytometry assay. G-3 aptamer demonstrated good binding kinetics to CCR5 expressing U373-Magi-CCR5E and CEM-NKr-CCR5 cells (see FIG. 3D) with an apparent $K_d$ values of ~110 nM. In the CCR5 negative CEM cells, only very higher concentration (>800 nM) of G-3 caused non-specific cellular binding ($K_d$>3000 nM) (see FIG. 3D).

It was next evaluated whether or not the selected G-3 aptamer requires CCR5 expression to target CCR5 expressing cells. The specific knockdown of CCR5 using a previously validated CCR5 siRNA demonstrated a loss of CCR5 at both the mRNA and cell surface. The suppression of CCR5 using siRNAs resulted in a loss of the Cy3-labeled G-3 aptamer and control APC-labeled CCR5 antibody (APC-CD195) binding to the CCR5 expressing cells (see FIG. 3E).

In addition, to determine whether or not the G-3 aptamer internalized in target cells real-time live-cell Z-axis confocal microscopy was carried out. The G-3 aptamer appeared to be selectively internalized within the CCR5 expressing U373-Magi-CCR5E cells, CEM-NKr-CCR5 cells and primary PBMCs, but not the U373-Magi and CEM control cells (see FIGS. 3F and 3G) and appeared to be preferentially retained in the cytoplasm (see FIG. 3H).

Example 18

CCR5 Aptamer Suppresses HIV-1 Infectivity of R5-Tropic HIV-1 in Primary PBMCs

HIV-1 commonly uses CCR5 or CXCR4 as a coreceptors along with CD4 to enter target cells (16). A number of new experimental CCR5 receptor antagonists have been designed to interfere with the interaction between CCR5 and HIV-1 (18,31,32). A "prophylactic" HIV-1 experiment was therefore conducted to determine whether the CCR5 aptamer G-3 would also block HIV infectivity of R5 viruses in cell culture. In this assay, primary PBMCs were first incubated with G-3 aptamer for 4-6 hours followed by infection with various HIV-1 stains (R5 viruses: JR-FL and Bal; X4 viruses: TIM and NL4-3). The G-3 aptamer efficiently neutralized HIV-1 infectivity of R5 strains with about 170~350 nM of $IC_{50}$ (see FIGS. 4A-4D and Table 3). The G3-aptamer had no observable suppression of those cells infected with X4 strains. These data indicate that the selected CCR5 aptamer (G-3) inhibits HIV-1 p24 production and provides protection from HIV infection by R5 viruses.

Table 3 summarizes the results from an HIV-1 challenge assay. The $IC_{50}$ value of G-3 aptamer was indicated here. G-3 aptamers with different concentrations were incubated with primary PBMCs. After 4-6 hours incubation, various viruses (R5 strains: JR-FL, Bal; or X4 strains: IIIB, NL4-3) were added into each well. The culture supernatants were collected at different time points after infection for HIV-1 p24 antigen ELISA assay. G-3 aptamer neutralized HIV-1 infectivity of R5 strains (JR-FL and BaL), but not X4 strains (NL4-3 and IIIB).

TABLE 3

| Virus | | Day-3 post-treatment | Day-5 post-treatment | Day-7 post-treatment | $R^2$ |
|---|---|---|---|---|---|
| | | | $IC_{50}$ (nM) | | |
| R5 | JRFL | 219.7 ± 55.6 | 232.6 ± 38.3 | 170.4 ± 47.0 | >0.9 |
| R5 | Bal | 349.4 ± 77.24 | 354.3 ± 113.3 | >1000 | >0.9 |
| X4 | IIIB | >1000 | Not converged | Not converged | <0.2 |
| X4 | NL4-3 | Not converged | Not converged | Not converged | <0.5 |

Example 19

Design of CCR5 Aptamer-siRNA Chimera Delivery Systems that Bind and are Internalized by Cells Expressing CCR5

Anti-HIV siRNAs have previously been delivered specifically to HIV-1 infected cells using RNA aptamer against HIV-1 envelop gp120 protein. In accordance with the present invention, a similar approach was utilized for cell-specific targeting of TNPO3 siRNA into cells expressing CCR5. TNPO3 (Transportin-3) is a cellular factor that is involved in facilitating cytoplasmic—nuclear trafficking of the HIV-1 pre-integration complex and has previously been shown by an siRNA screen to block HIV-1 infection at the afferent stage. As shown in FIGS. 5A and 5B, two CCR5 aptamer-siRNA chimeras (G-3-TNPO3 27-mer OVH chimera and G-3-TNPO3 27-mer Blunt) were designed and prepared as previously described. Nucleotide linkers (2Us or 8Us) with different lengths were inserted between the aptamer portion and the TNPO3 DsiRNA portion to increase molecular flexibility for correct folding of the aptamer and for Dicer processing of DsiRNA. A 2-nt 3'-overhang was designed in the DsiRNA portion to facilitate Dicer binding and entry.

To determine whether the designed chimeras are able to specifically bind and be internalized by CCR5 expressing cells, a flow cytomerty assay and a live cell Z-axis confocal microscopy experiment, were performed. G-3-27-mer-TNPO3 OVH chimera was chosen for binding affinity test with PBMC-CD4+ cells, CEM-NKr-CCR5 positive cells, and CEM negative cells. The aptamer-sense strand and antisense strand of the chimera were labeled by Cy3 and Cy5 dye, respectively. Subsequently, sense and antisense RNAs were annealed to form aptamer-siRNA chimera containing either single color or dual color labeling. Flow cytometric results showed that G-3 aptamer (either non-labeled or Cy3-labeled) delivered ~70%-80% Cy5 labeled siRNA portion into CCR5 expressing PBMCs and CEM-NKr-CCR5 cells (see FIGS. 5C-5E). Similar with the parental G-3 aptamer, the Cy3-labeled aptamer-siRNA chimeras selectively bound and were internalized into cells expressing CCR5 after 5 h post-treatment (see FIG. 5F).

Example 20

CCR5 Aptamer-siRNA Chimeras Specifically Knockdown TNPO3 Expression Via RNAi Pathway and do not Trigger a Type I Interferon Response To establish that the siRNA component was functioning along with the aptamer, after internalization of the CCR5 aptamer-siRNA chimeras in CCR5 expressing cells, the relative levels of inhibition of TNPO3 expression were evaluated. Specially, CEM-NKr-CCR5 positive cells or CEM-NKr control cells were directly incubated with the aptamer-siRNA chimeras, G-3 aptamer, or a non-functional control aptamer-scrambled siRNA chimera. In parallel, cells were transfected with the experimental RNAs by using a commercial transfection agent (Trans IT-TKO). Silencing of TNPO3 was assessed by the degree of TNPO3 mRNA knockdown using qRT-PCR (see FIG. 6A). In the presence of transfection agent, TNPO3 gene silencing was observed in both CEM-NKr-CCR5 and CEM-NKr control cells after the treatment of G-3-TNPO3 siRNA chimeras. However, in the absence of transfection agent, the G-3-TNPO3 siRNA chimeras, but not the G-3-scrambled siRNA chimera or non-targeting aptamer (gp120 aptamer A-1)-TNPO3 siRNA conjugate, reduced TNPO3 mRNA levels. Importantly, the reduction was CCR5 positive cell specific, as control CEM-NKr negative cells treated with either of the G-3-TNPO3 siRNA chimeras exhibited no TNPO3 mRNA reduction. Similarly, the G-3 aptamer delivered TNPOs DsiRNA also resulted in a decrease in target mRNA levels 48 hours post-treatment, with efficiency comparable to a previous validated transfection agent (G5 dendrimer) (see FIG. 6B).

In order to validate that the siRNAs released from the chimeras were actually triggering RNAi, siRNA-directed mRNA cleavage was investigated using a modified 5'-RACE (Rapid amplification of cDNA ends) PCR assay. It has been established that Ago2 mediates cleavage between bases 10 and 11 relative to the 5' end of each siRNA. Thus the RACE PCR product sequence analyses of the target should reveal a 3' linker addition at the base positioned 11 nucleotides from the 5' end of the siRNA guide strand. PCR bands of the predicted lengths were detected in the total RNAs from CEM-NKr-CCR5 cells treated with the chimeras after two nested PCR reactions (see FIG. 6C). The individual clones were sequenced to verify the expected PCR products. Several various cleavage sites were found in the samples treated with the two chimeras. FIG. 6D indicates the Ago2 cleavage sires and proposed direction of Dicing. For the 27-mer OVH chimera, one major cleavage was observed, suggesting that Dicer preferentially enter the DsiRNA from the 3'-overhang of the sense strand. The short linker (2 Us) may limit the Dicer entry from the 5'-end of the sense strand. In the case of the 27-mer Blunt chimera, several different cleavage sites were generated, suggesting that Dicer might bi-directionally enter the DsiRNA to generate different 21-mer siRNA species. Different from the observation in the 27-mer OVH chimeras, the longer linker (8Us) of the 27-mer Blunt chimera may allow the Dicer entry from 5'-end of the sense strand. Taken together, these results provide strong evidence that the chimera-delivered siRNAs are processed intracellularly and trigger sequence-specific degradation of the TNPO3 target mRNA.

As a final test for nonspecific inhibitory activity, the aptamer mediated siRNA delivery system was monitored for induction of type I interferon response (IFN). The levels of two different type I IFN-stimulated gene expressions (mRNAs) were quantified by quantitative RT-PCR (FIG. 6E). IFN-α was used as a positive control to confirm up-regulation of p56 (CDKL2) and OAS1 gene expression. The results indicate that the treatment of PBMC-CD4+ cells with these chimeras did not activate the type I IFN pathway.

Example 21

CCR5 Aptamer-siRNA Chimeras Inhibit HIV-1 Infection in Primary Human PBMCs

It has been reported previously that as one of HIV-1 host dependency factors (HDFs), TNPO3 is a karyopherin required for viral integration, suggesting it is a potential therapeutic target. Therefore, the anti-HIV-1 activities of the CCR5 aptamer-mediated TNPO3 siRNA delivery system were assessed. HIV-1 challenge assay was performed as previously described. In the assay, the experimental RNAs were incubated with human PBMC-CD4+ cells. After 4-6 hours treatment, the cells were challenged by the R5 virus (JR-FL). The culture supernatants were collected at five days after treatment for HIV-1 p24 antigen ELISA assay. Results presented in FIG. 7A show that each of the aptamers and chimeras inhibit p24 production, but the strongest inhibition was observed with the G-3-TNPO3 OVH chimera treatment. This is likely due to the contribution of the siRNA component of the chimera in silencing TNPO3 expression in the treated cells.

To confirm that the siRNA component was functioning along with the aptamer, following internalization of the chimera in infected cells, the relative levels of inhibition of TNPO3 gene expression were also evaluated by qRT-PCR assay (see FIG. 7B). Specific down regulation of the TNPO3 mRNA was observed, a direct consequence of the CCR5 aptamer-mediated DsiRNA delivery. In contrast, treatment of these cells with the CCR5 aptamer alone or irrelative RNA had no apparent effect on TNPO3 levels. Collectively, these results provide further evidence that the aptamer delivered siRNA triggers RNAi, thereby resulting in dual inhibitory effect on HIV-1 replication.

TABLE 4

The IC50 value was calculated based on HIV-1 protection assay. Human PBMC-CD4+ cells or in vivo generated human CD4+ T cells were pre-treated with experimental RNAs before exposure to HIV-1 viruses.

|  | Virus | | Day-3 post-treatment | Day-5 post-treatment $IC_{50}$ (nM) | Day-7 post-treatment | $R^2$ |
|---|---|---|---|---|---|---|
| Primary PBMCs (G-3 aptamer) | R5 | JR-FL | 219.7 ± 55.6 | 232.6 ± 38.3 | 170.4 ± 47.0 | >0.9 |
|  | R5 | Bal | 349.4 ± 77.24 | 354.3 ± 113.3 | >1000 | >0.9 |
|  | X4 | IIIB | >1000 | Not converged | Not converged | <0.2 |
|  | X4 | NL4-3 | Not converged | Not converged | Not converged | <0.5 |
| Primary PBMCs (G-3-TNPO3 OVH Chimera) | R5 | JR-FL | 23.2 ± 6.2 | 142.6 ± 41.3 | 79.3 ± 21.6 | >0.9 |
| in vivo generated human CD4+ T cells | R5 | JR-FL | 47.98 ± 8.57 | 58.51 ± 11.22 | 17.09 ± 5.90 | >0.9 |
|  | R5 | Bal | 147.6 ± 45.69 | 245.5 ± 35.76 | 243.2 ± 46.16 | >0.9 |

TABLE 4-continued

The IC50 value was calculated based on HIV-1 protection assay. Human
PBMC-CD4+ cells or in vivo generated human CD4+ T cells
were pre-treated with experimental RNAs before exposure to HIV-1 viruses.

| | Virus | | Day-3 post-treatment | Day-5 post-treatment $IC_{50}$ (nM) | Day-7 post-treatment | $R^2$ |
|---|---|---|---|---|---|---|
| (G-3 aptamer) | X4 | NL4-3 | Not converged | Not converged | Not converged | — |

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

REFERENCES

1. Izzedine, H., Harris, M. and Perazella, M. A. (2009) The nephrotoxic effects of HAART. *Nat Rev Nephrol*, 5, 563-573.
2. Robinson-Papp, J., Elliott, K. J. and Simpson, D. M. (2009) HIV-related neurocognitive impairment in the HAART era. *Curr HIV/AIDS Rep*, 6, 146-152.
3. Richman, D. D., Margolis, D. M., Delaney, M., Greene, W. C., Hazuda, D. and Pomerantz, R. J. (2009) The challenge of finding a cure for HIV infection. *Science*, 323, 1304-1307.
4. Joshi, P. J., Fisher, T. S. and Prasad, V. R. (2003) Anti-HIV inhibitors based on nucleic acids: emergence of aptamers as potent antivirals. *Curr Drug Targets Infect Disord*, 3, 383-400.
5. Scherer, L., Rossi, J. J. and Weinberg, M. S. (2007) Progress and prospects: RNA-based therapies for treatment of HIV infection. *Gene Ther*, 14, 1057-1064.
6. Zhang, Z., Blank, M. and Schluesener, H. J. (2004) Nucleic acid aptamers in human viral disease. *Arch Immunol Ther Exp (Warsz)*, 52, 307-315.
7. Sundaram, P., Kurniawan, H., Byrne, M. E. and Wower, J. (2013) Therapeutic RNA aptamers in clinical trials. *Eur J Pharm Sci*, 48, 259-271.
8. Li, X., Zhao, Q. and Qiu, L. (2013) Smart ligand: aptamer-mediated targeted delivery of chemotherapeutic drugs and siRNA for cancer therapy. *J Control Release*, 171, 152-162.
9. Nimjee, S. M., Rusconi, C. P. and Sullenger, B. A. (2005) Aptamers: an emerging class of therapeutics. *Annu Rev Med*, 56, 555-583.
10. Thiel, K. W. and Giangrande, P. H. (2009) Therapeutic applications of DNA and RNA aptamers. *Oligonucleotides*, 19, 209-222.
11. Shum, K. T., Zhou, J. and Rossi, J. J. (2013) Aptamer-based therapeutics: new approaches to combat human viral diseases. *Pharmaceuticals*, 6, 1507-1542.
12. Held, D. M., Kissel, J. D., Patterson, J. T., Nickens, D. G. and Burke, D. H. (2006) HIV-1 inactivation by nucleic acid aptamers. *Front Biosci*, 11, 89-112.
13. Zhou, J. and Rossi, J. J. (2011) Cell-specific aptamer-mediated targeted drug delivery. *Oligonucleotides*, 21, 1-10.
14. Mallikaratchy, P., Liu, H., Huang, Y. F., Wang, H., Lopez-Colon, D. and Tan, W. (2009) Using aptamers evolved from cell-SELEX to engineer a molecular delivery platform. *Chem Commun (Camb)*, 3056-3058.
15. Zhou, J. and Rossi, J. J. (2012) Therapeutic Potential of Aptamer-siRNA Conjugates for Treatment of HIV-1. *BioDrugs: clinical immunotherapeutics, biopharmaceuticals and gene therapy*, 26, 393-400.
16. Neff, C. P., Zhou, J., Remling, L., Kuruvilla, J., Zhang, J., Li, H., Smith, D. D., Swiderski, P., Rossi, J. J. and Akkina, R. (2011) An aptamer-siRNA chimera suppresses HIV-1 viral loads and protects from helper CD4(+) T cell decline in humanized mice. *Sci Transl Med*, 3, 66ra66.
17. Zhou, J., Neff, C. P., Swiderski, P., Li, H., Smith, D. D., Aboellail, T., Remling-Mulder, L., Akkina, R. and Rossi, J. J. (2013) Functional In Vivo Delivery of Multiplexed Anti-HIV-1 siRNAs via a Chemically Synthesized Aptamer With a Sticky Bridge. *Mol Ther*, 21, 192-200.
18. Zhou, J., Swiderski, P., Li, H., Zhang, J., Neff, C. P., Akkina, R. and Rossi, J. J. (2009) Selection, characterization and application of new RNA HIV gp 120 aptamers for facile delivery of Dicer substrate siRNAs into HIV infected cells. *Nucleic Acids Res*.
19. Berger, E. A., Murphy, P. M. and Farber, J. M. (1999) Chemokine receptors as HIV-1 coreceptors: roles in viral entry, tropism, and disease. *Annual review of immunology*, 17, 657-700.
20. Pelchen-Matthews, A., Signoret, N., Klasse, P. J., Fraile-Ramos, A. and Marsh, M. (1999) Chemokine receptor trafficking and viral replication. *Immunological reviews*, 168, 33-49.
21. Ugolini, S., Mondor, I. and Sattentau, Q. J. (1999) HIV-1 attachment: another look. *Trends Microbiol*, 7, 144-149.
22. Meanwell, N. A. and Kadow, J. F. (2003) Inhibitors of the entry of HIV into host cells. *Curr Opin Drug Discov Devel*, 6, 451-461.
23. Guo, K. T., Paul, A., Schichor, C., Ziemer, G. and Wendel, H. P. (2008) CELL-SELEX: Novel Perspectives of Aptamer-Based Therapeutics. *Int J Mot Sci*, 9, 668-678.
24. Fang, X. and Tan, W. (2009) Aptamers Generated from Cell-SELEX for Molecular Medicine: A Chemical Biology Approach. *Acc Chem Res*.
25. Cerchia, L. and de Franciscis, V. (2010) Targeting cancer cells with nucleic acid aptamers. *Trends Biotechnol*, 28, 517-525.
26. Vodicka, M. A., Goh, W. C., Wu, L. I., Rogel, M. E., Bartz, S. R., Schweickart, V. L., Raport, C. J. and Emerman, M. (1997) Indicator cell lines for detection of primary strains of human and simian immunodeficiency viruses. *Virology*, 233, 193-198.
27. Howell, D. N., Andreotti, P. E., Dawson, J. R. and Cresswell, P. (1985) Natural killing target antigens as inducers of interferon: studies with an immunoselected, natural killing-resistant human T lymphoblastoid cell line. *Journal of immunology*, 134, 971-976.
28. Lyerly, H. K., Reed, D. L., Matthews, T. J., Langlois, A. J., Ahearne, P. A., Petteway, S. R., Jr. and Weinhold, K. J. (1987) Anti-GP 120 antibodies from HIV seropositive individuals mediate broadly reactive anti-HIV ADCC. *AIDS research and human retroviruses*, 3, 409-422.
29. Tuerk, C. and Gold, L. (1990) Systematic evolution of ligands by exponential enrichment: RNA ligands to bacteriophage T4 DNA polymerase. *Science*, 249, 505-510.
30. Thiel, K. W., Hernandez, L. I., Dassie, J. P., Thiel, W. H., Liu, X., Stockdale, K. R., Rothman, A. M., Hernandez, F. J., McNamara, J. O., 2nd and Giangrande, P. H. (2012) Delivery of chemo-sensitizing siRNAs to HER2+-breast cancer cells using RNA aptamers. *Nucleic Acids Res*, 40, 6319-6337.
31. Cerchia, L., Duconge, F., Pestourie, C., Boulay, J., Aissouni, Y., Gombert, K., Tavitian, B., de Franciscis, V. and Libri, D. (2005) Neutralizing aptamers from whole-cell SELEX inhibit the RET receptor tyrosine kinase. *PLoS Biol*, 3, e123.
32. Cerchia, L., Esposito, C. L., Jacobs, A. H., Tavitian, B. and de Franciscis, V. (2009) Differential SELEX in human glioma cell lines. *PloS one*, 4, e7971.
33. Thiel, W. H., Bair, T., Peek, A. S., Liu, X., Dassie, J., Stockdale, K. R., Behlke, M. A., Miller, F. J., Jr. and Giangrande, P. H. (2012) Rapid identification of cell-specific, internalizing RNA aptamers with bioinformatics analyses of a cell-based aptamer selection. *PloS one*, 7, e43836.
34. Signoret, N., Pelchen-Matthews, A., Mack, M., Proudfoot, A. E. and Marsh, M. (2000) Endocytosis and recycling of the HIV coreceptor CCR5. *The Journal of cell biology*, 151, 1281-1294.
35. Vila-Coro, A. J., Mellado, M., Martin de Ana, A., Lucas, P., del Real, G., Martinez, A. C. and Rodriguez-Frade, J. M. (2000) HIV-1 infection through the CCR5 receptor is blocked by receptor dimerization. *Proceedings of the National Academy of Sciences of the United States of America*, 97, 3388-3393.
36. Stull, R. A. and Szoka, F. C., Jr. (1995) Antigene, ribozyme and aptamer nucleic acid drugs: progress and prospects. *Pharm Res*, 12, 465-483.
37. Zhou, J. and Rossi, J. J. (2011) Aptamer-targeted RNAi for HIV-1 therapy. *Methods Mol Biol*, 721, 355-371.
38. Zhou, J. and Rossi, J. J. (2011) Progress in RNAi-based antiviral therapeutics. *Methods Mol Biol*, 721, 67-75.
39. Cerchia, L., Giangrande, P. H., McNamara, J. O. and de Franciscis, V. (2009) Cell-specific aptamers for targeted therapies. *Methods Mol Biol*, 535, 59-78.
40. Murphy, P. M., Baggiolini, M., Charo, I. F., Hebert, C. A., Horuk, R., Matsushima, K., Miller, L. H., Oppenheim, J. J. and Power, C. A. (2000) International union of pharmacology. XXII. Nomenclature for chemokine receptors. *Pharmacological reviews*, 52, 145-176.
41. Sabbe, R., Picchio, G. R., Pastore, C., Chaloin, O., Hartley, O., Offord, R. and Mosier, D. E. (2001) Donor- and ligand-dependent differences in C-C chemokine receptor 5 reexpression. *Journal of virology*, 75, 661-671.
42. Mack, M., Luckow, B., Nelson, P. J., Cihak, J., Simmons, G., Clapham, P. R., Signoret, N., Marsh, M., Stangassinger, M., Borlat, F. et al. (1998) Aminooxypentane-RANTES induces CCR5 internalization but inhibits recycling: a novel inhibitory mechanism of HIV infectivity. *The Journal of experimental medicine*, 187, 1215-1224.
43. Mariani, R., Wong, S., Mulder, L. C., Wilkinson, D. A., Reinhart, A. L., LaRosa, G., Nibbs, R., O'Brien, T. R., Michael, N. L., Connor, R. I. et al. (1999) CCR2-64I polymorphism is not associated with altered CCR5 expression or coreceptor function. *Journal of virology*, 73, 2450-2459.
44. Vila-Coro, A. J., Mellado, M., Martin de Ana, A., Martinez, A. C. and Rodriguez-Frade, J. M. (1999) Characterization of RANTES- and aminooxypentane-RANTES-triggered desensitization signals reveals differences in recruitment of the G protein-coupled receptor complex. *Journal of immunology*, 163, 3037-3044.

Informal Sequence Listing:

(SEQ ID NO: 1)
5'-GGG AGG ACG AUG CGG GCC UUC GUU UGU UUC GUC CAC AGA CGA CUC GCC CGA-3'

(SEQ ID NO: 2)
5'-GGG AGG ACG ATG CGG - N20- CAG ACG ACT CGC CCG A-3' (51 nt)

(SEQ ID NO: 3)
5'-TAA TAC GAC TCA CTA TAG GGA GGA CGA TGC GG-3' (32 mer)

(SEQ ID NO: 4)
5'-TCG GGC GAG TCG TCT G-3' (16 mer)

(SEQ ID NO: 5)
5' P-CUC UGC UUC GGU GUC GAA A dTdT-3'

(SEQ ID NO: 6)
5' P-UUU CGA CAC CGA AGC AGA G dTdT-3'

(SEQ ID NO: 7)
5'-CGA CAU UGC AGC UCG UGU ACC AG dGdC-3'

(SEQ ID NO: 8)
5'-GCC UGG UAC ACG AGC UGC AAU GUC GUU-3'

(SEQ ID NO: 9)
5'-GGG AGG ACG AUG CGG GCC UUC GUU UGU UUC GUC CAC AGA CGA CUC GCC CGA-3'

(SEQ ID NO: 10)
5'-GGG AGG ACG AUG CGG GCC UUC GUU UGU UUC GUC CAC AGA CGA CUC GCC CGA UU CAA AGC CGA CAU UGC AGC UCG UGU ACC-3'

(SEQ ID NO: 11)
5'-UAC ACG AGC UGC AAU GUC GGC UUU G-3'

(SEQ ID NO: 12)
5'-GGG AGG ACG AUG CGG GCC UUC GUU UGU UUC GUC CAC AGA CGA CUC GCC CGA UUUUUUUU CGA CAU UGC AGC UCG UGU ACC AGG C-3'

(SEQ ID NO: 13)
5'-GCC UGG UAC ACG AGC UGC AAU GUC GGC-3'

(SEQ ID NO: 14)
5'-GGG AGG ACG AUG CGG GCC UUC GUU UGU UUC GUC CAC AGA CGA CUC GCC CGA UU ACG UGA GAC GUU CGG UGA AUU-3'

(SEQ ID NO: 15)
5'-UUC ACC GAA CGU CUC ACG UdTdT-3'

(SEQ ID NO: 16)
5'-TAA TAC GAC TCA CTA TAG GGA GGA CGA TGC GG-3' (32 mer)

(SEQ ID NO: 17)
5'-TCG GGC GAG TCG TCT G-3' (16 mer)

(SEQ ID NO: 18)
5'-CAT TGA CCT CAA CTA CAT G-3'

(SEQ ID NO: 19)
5'-TCT CCA TGG TGG TGA AGA C-3'

(SEQ ID NO: 20)
5' CAG ATT GAT GGT GCC TAC AGT CGG GCG UGT CGT CTG 3'

(SEQ ID NO: 21)
5' AAT GAT ACG GCG ACC ACC GAC AGG TTC AGA GTT CGA TCG GGA GGA CGA TGC GG 3')

(SEQ ID NO: 22)
5' CAG ATT GAT GGT GCC TAC AGT CGG GCG UGT CGT CTG 3')

(SEQ ID NO: 23)
5' CAA GCA GAA GAC GGC ATA CGA GAT NNNNNN CAG ATT GAT GGT GCC TAC AG 3'

(SEQ ID NO: 24)
5' AAT GAT ACG GCG ACC ACC GA 3'

(SEQ ID NO: 25)
5' CAA GCA GAA GAC GGC ATA CG (SEQ ID NO: 26)
5' AAT GAT ACG GCG ACC ACC GA 3'

(SEQ ID NO: 27)
5' P-CUC UGC UUC GGU GUC GAA A dTdT -3'

(SEQ ID NO: 28)
5' P-UUU CGA CAC CGA AGC AGA G dTdT -3'

(SEQ ID NO: 29)
5'-AAC ATG CTG GTC ATC CTC AT-3'

(SEQ ID NO: 30)
5'-AAT AGA GCC CTG TCA AGA GT-3'

(SEQ ID NO: 31)
5'-CCT GGA AGG GAT GTG TGC-3'

(SEQ ID NO: 32)
5'-AAA AAG GCA AAG AAG TCA CAT CA-3'

(SEQ ID NO: 33)
5'-CGA CUG GAG CAC GAG GAC ACU GAC AUG GAC UGA AGG AGU AGA AA-3'

(SEQ ID NO: 34)
5'-CAG GTA ACA CTG TAA GGA TCT CCA GC-3'

(SEQ ID NO: 35)
5'-GGA CAC TGA CAT GGA CTG AAG GAG TA-3'

(SEQ ID NO: 36)
5'-TAA AGA GGC ATG AGA GTC TGT GGG GA-3'

(SEQ ID NO: 37)
5' CCG GAT CTG TAA CAA CTG GTC TGA GA-3'

(SEQ ID NO: 38)
5'-TCA AGT ATG GCA AGG CTG TG-3'

(SEQ ID NO: 39)
5'-GAG GCT CTG CTT CTG CAT CT-3'

(SEQ ID NO: 40)
5'-ACC GTC TTG GAA CTG GTC AC-3'

(SEQ ID NO: 41)
5'-ATG TTC CTT GTT GGG TCA GC-3'

(SEQ ID NO: 42)
5'-UUCGUCUG(U/G)G-3'

(SEQ ID NO: 43)
5'-AUCGUCUAUUAGUCGCUGGC-3'

(SEQ ID NO: 44)
5'-UCCUUGGCUUUUCGUCUGUG-3'

(SEQ ID NO: 45)
5'-GCCUUCGUUUGUUUCGUCCA-3'

(SEQ ID NO: 46)
5'-UCCCGGCUCGUUCGUCUGUG-3'

(SEQ ID NO: 47)
5'-UUCGUCAU UUUUCGUCUGGG-3'

(SEQ ID NO: 48)
5'-CCUUUCGUCUGUUUCUGCGC-3'

EMBODIMENTS

Embodiment 1

A 2'-fluoropyrimidine modified RNA aptamer which selectively binds to human CCR5.

Embodiment 2

The aptamer of embodiment 1 wherein said aptamer selectively binds and internalizes into human CCR5-expressing cells.

Embodiment 3

The aptamer of embodiment 1 wherein said aptamer has at least 80% sequence identity with G-3:

(SEQ ID NO: 1)
5'-GGG AGG ACG AUG CGG GCC UUC GUU UGU UUC GUC CAC AGA CGA CUC GCC CGA-3'.

Embodiment 4

The aptamer of embodiment 1 wherein said aptamer has substantially the same sequence as G-3 (SEQ ID NO: 1).

Embodiment 5

A chimeric construct comprising an aptamer according to embodiment 1 and antiviral siRNA, optionally linked by a suitable linker.

Embodiment 6

A dual inhibitory drug for the selective delivery of antiviral siRNA to HIV-infected cells, said drug comprising an aptamer according to embodiment 1 and an antiviral siRNA, optionally linked by a suitable linker.

Embodiment 7

A method of neutralizing R5 virus infection in primary PBMCs, said method comprising contacting said PBMCs with an aptamer according to embodiment 1.

Embodiment 8

A method of neutralizing R5 virus infection in primary PBMCs, said method comprising contacting said PBMCs with a dual inhibitory drug according to embodiment 6.

Embodiment 9

A method of inhibiting the ability of CCR5 to facilitate entry of HIV into target cells, said method comprising contacting said target cell with an aptamer according to embodiment 1.

Embodiment 10

A method of inhibiting the ability of CCR5 to facilitate entry of HIV into target cells, said method comprising contacting said target cell with a dual inhibitory drug according to embodiment 6.

Embodiment 11

A method of treating a subject infected with HIV, said method comprising administering to said subject an effective amount of a dual inhibitory drug according to embodiment 6.

Embodiment 12

A method of cell-specific delivery of antiviral siRNA to a subject in need thereof, said method comprising administering said antiviral siRNA together with an aptamer according to embodiment 1, wherein said antiviral siRNA and said aptamer are optionally linked by a suitable linker.

Embodiment 13

A method of identifying HIV-1 susceptible cells, said method comprising: (a) contacting test cells with an aptamer according to embodiment 1 and (b) identifying those cells which bind to said aptamer as HIV susceptible.

Embodiment 14

A method to block viral replication, said method comprising administering an aptamer-siRNA chimera of embodiment 5 to a subject in need thereof.

Embodiment 15

A method of selectively delivering antiviral siRNAs to HIV-infected cells, said method comprising contacting said cells with an aptamer-siRNA chimera according to embodiment 5.

Embodiment 16

A kit comprising:
(a) an aptamer according to embodiment 1, and
(b) antiviral siRNA.

Embodiment 17

The kit of embodiment 16 wherein said aptamer is G-3 (SEQ ID NO: 1).

Embodiment 18

An in vitro complex comprising an aptamer according to embodiment 1 and human CCR5.

Embodiment 19

The in vitro complex of embodiment 18 wherein the human CCR5 is bound to a solid support.

Embodiment 20

The in vitro complex according to embodiment 18 wherein said solid support is a protein chip.

Embodiment 21

An in vitro complex comprising an HIV infected cell and an aptamer according to embodiment 1.

Embodiment 22

The in vitro complex according to embodiment 21, further comprising antiviral siRNA, wherein said aptamer and said antiviral siRNA are optionally linked by a suitable linker.

Embodiment 23

A cell-type specific aptamer-stick-nanodisc delivery system for targeted drug delivery comprising an RNA aptamer according to embodiment 1 and a lipid molecule attached to a complementary 17-base GC-rich bridge.

What is claimed is:

1. A chimeric construct comprising an aptamer and an antiviral therapeutic moiety, optionally linked by a suitable linker, wherein said aptamer has at least 80% sequence identity with G-3:

(SEQ ID NO: 1)
5'-GGG AGG ACG AUG CGG GCC UUC GUU UGU UUC GUC CAC AGA CGA CUC GCC CGA-3'.

2. The chimeric construct of claim 1, wherein said antiviral therapeutic moiety is an antiviral nucleic acid.

3. The chimeric construct of claim 2, wherein said antiviral nucleic acid is an antiviral RNA.

4. The chimeric construct of claim 1, wherein said aptamer is a 2'-fluoropyrimidine modified aptamer.

5. The chimeric construct of claim 1, wherein said antiviral therapeutic moiety is an antisense nucleic acid.

6. The chimeric construct of claim 1, wherein said antiviral therapeutic moiety is an RNA decoy or miRNA.

7. The chimeric construct of claim 1, wherein said antiviral therapeutic moiety comprises a lipid-based nanodisc.

8. A dual inhibitory drug for the selective delivery of a therapeutic moiety to HIV-infected cells, said drug comprising an aptamer and a therapeutic moiety, optionally linked by a suitable linker, wherein said aptamer has at least 80% sequence identity with G-3:

(SEQ ID NO: 1)
5'-GGG AGG ACG AUG CGG GCC UUC GUU UGU UUC GUC CAC AGA CGA CUC GCC CGA-3'.

9. The dual inhibitory drug of claim 8, wherein said therapeutic moiety is an antiviral nucleic acid.

10. The dual inhibitory drug of claim 9, wherein said antiviral nucleic acid is an antiviral RNA.

11. The dual inhibitory drug of claim 8, wherein said aptamer is a 2'-fluoropyrimidine modified aptamer.

12. The dual inhibitory drug of claim 11, wherein said therapeutic moiety is an antiviral siRNA.

13. A method of treating a subject infected with HIV, said method comprising administering to said subject an effective amount of a dual inhibitory drug for the selective delivery of a therapeutic moiety to HIV-infected cells, said drug comprising an aptamer and a therapeutic moiety, optionally linked by a suitable linker, wherein said aptamer selectively binds to human CCR5 and having at least 80% sequence identity with G-3:

```
                                             (SEQ ID NO: 1)
5'-GGG AGG ACG AUG CGG GCC UUC GUU UGU UUC GUC CAC
AGA CGA CUC GCC CGA-3'.
```

14. A method of cell-specific delivery of a therapeutic moiety to a subject in need thereof, said method comprising administering an antiviral therapeutic moiety together with an aptamer, wherein said antiviral therapeutic moiety and said aptamer are optionally linked by a suitable linker, wherein said aptamer selectively binds to human CCR5 and having at least 80% sequence identity with G-3:

```
                                             (SEQ ID NO: 1)
5'-GGG AGG ACG AUG CGG GCC UUC GUU UGU UUC GUC CAC
AGA CGA CUC GCC CGA-3'.
```

15. The method of claim 13 or 14, wherein said antiviral therapeutic moiety is an antiviral nucleic acid.

16. The method of claim 15, herein said antiviral nucleic acid is an antiviral RNA.

17. The method of claim 13, wherein said aptamer is a 2'-fluoropyrimidine modified aptamer.

18. The method of claim 14, wherein said aptamer is a 2'-fluoropyrimidine modified aptamer.

* * * * *